US010251377B2

(12) United States Patent
Clube

(10) Patent No.: US 10,251,377 B2
(45) Date of Patent: Apr. 9, 2019

(54) TRANSGENIC NON-HUMAN VERTEBRATE FOR THE EXPRESSION OF CLASS-SWITCHED, FULLY HUMAN, ANTIBODIES

(71) Applicant: Kymab Limited

(72) Inventor: Jasper Clube, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 14/498,685

(22) Filed: Sep. 26, 2014

(65) Prior Publication Data

US 2015/0082466 A1 Mar. 19, 2015

Related U.S. Application Data

(63) Continuation of application No. PCT/GB2013/050683, filed on Mar. 18, 2013, which is a continuation-in-part of application No. 13/433,084, filed on Mar. 28, 2012, and a continuation-in-part of application No. 13/434,361, filed on Mar. 29, 2012, now Pat. No. 9,253,965.

(30) Foreign Application Priority Data

May 4, 2012 (GB) .................................. 1207814.3
May 17, 2012 (GB) .................................. 1208708.6
Sep. 20, 2012 (GB) .................................. 1216795.3

(51) Int. Cl.
| | |
|---|---|
| *A01K 67/027* | (2006.01) |
| *C12N 15/06* | (2006.01) |
| *C12N 15/87* | (2006.01) |
| *A61K 39/395* | (2006.01) |
| *C07H 21/04* | (2006.01) |
| *C07K 16/46* | (2006.01) |
| *C12N 15/85* | (2006.01) |
| *C07K 16/00* | (2006.01) |

(52) U.S. Cl.
CPC .......... *A01K 67/0278* (2013.01); *C07K 16/00* (2013.01); *C07K 16/461* (2013.01); *C07K 16/462* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 2317/92* (2013.01)

(58) Field of Classification Search
CPC ............ A01K 67/0278; A01K 2207/15; A01K 2217/15; A01K 2217/072; A01K 2227/105; C12N 15/8509; C07H 21/04; C07K 16/462
USPC .................. 800/18; 424/133.1; 435/328, 463; 536/23.5, 24.1
See application file for complete search history.

(56) References Cited

U.S. PATENT DOCUMENTS

| | | | |
|---|---|---|---|
| 4,720,449 A | 1/1988 | Borror et al. | |
| 5,169,939 A | 12/1992 | Gefter et al. | ............... 530/387.3 |
| 5,545,806 A | 8/1996 | Lonberg et al. | |
| 5,545,807 A | 8/1996 | Surani et al. | ..................... 800/2 |
| 5,565,321 A | 10/1996 | Spriggs et al. | |
| 5,633,425 A | 5/1997 | Lonberg et al. | |
| 5,770,429 A | 6/1998 | Lonberg et al. | |
| 5,789,215 A | 8/1998 | Berns et al. | ............... 435/172.3 |
| 5,939,598 A | 8/1999 | Kucherlapati et al. | ......... 800/25 |
| 5,948,600 A | 9/1999 | Roschger et al. | |
| 6,114,598 A | 9/2000 | Kucherlapati et al. | |
| 6,130,364 A | 10/2000 | Jakobovits et al. | |
| 6,162,963 A | 12/2000 | Kucherlapati et al. | ......... 800/18 |
| 6,319,906 B1 | 11/2001 | Bennett et al. | |
| 6,395,487 B1 | 5/2002 | Bradley et al. | |
| 6,461,818 B1 | 10/2002 | Bradley et al. | |

(Continued)

FOREIGN PATENT DOCUMENTS

| | | | |
|---|---|---|---|
| CA | 2 307 503 A1 | 11/2001 | ............. A61K 39/42 |
| CA | 2747534 | 6/2010 | |

(Continued)

OTHER PUBLICATIONS

Ahmed, "Sanofi-aventis and Regeneron Extend Therapeutic Antibody Agreement," *PharmaDeals Review*, vol. 2009, Issue No. 11, p. 115, Nov. 2009.
Andrew J. Murphy, Declaration of Andrew J. Murphy, dated Oct. 6, 2014, including Slide Presentation dated Nov. 3, 2009, at Wellcome Trust Advanced Course: Genetic Manipulation of ES Cells, in Hirixton, ITK, entitled "BAC-based Modifications of the Mouse Genome: The Big and the.Backward," cited in an IDS in U.S. Appl. No. 14/192,051 of MacDonald et al., 62 pages.
Arnaout R., et al., "High-Resolution Description of Antibody Heavy-Chain Repertoires in Humans," *PLOS One*, vol. 6, Issue No. 8, pp. e22365-1-e22365-8, 2011.
Atlas Genetics Oncology, Atlas of Genetics and Cytogenetics in Oncology and Hematology: VPREB1, [online] [retrieved on May 25, 2015] Retrieved from the Internet <http://atlasgeneticsoncology.org/Genes/GC_VPREB1.html>, 5 pages.

(Continued)

*Primary Examiner* — Shin Lin Chen
(74) *Attorney, Agent, or Firm* — Nutter McClennen & Fish LLP

(57) ABSTRACT

The present invention relates to humanisation of antibodies in vivo. The invention provides non-human vertebrates, cells, populations and methods useful for humanising chimaeric antibodies in vivo. Using the present invention it is possible straightforwardly and rapidly to obtain antigen-specific antibodies that are fully human (ie, comprising human variable and constant regions) and have undergone recombination, junctional diversification, affinity maturation and isotype switching in vivo in a non-human vertebrate system. Furthermore, such antibodies are humanised (eg, totally human)—and selected—totally in vivo, and as such the present invention harnesses in vivo filtering for expressibility, affinity and biophysical characteristics in the context of the desired human variable and constant region pairings. This is avoids problems of down-grading antibody characteristics when humanising the constant region of chimaeric antibodies in vitro.

30 Claims, 9 Drawing Sheets

(56) References Cited

U.S. PATENT DOCUMENTS

| | | | |
|---|---|---|---|
| 6,596,541 B2 | 7/2003 | Murphy et al. | 435/463 |
| 6,657,103 B1 | 12/2003 | Kucherlapati et al. | |
| 6,673,986 B1 | 1/2004 | Kucherlapati et al. | 800/18 |
| 6,713,610 B1 | 3/2004 | Kucherlapati et al. | 530/388.23 |
| 6,833,268 B1 | 12/2004 | Green et al. | 435/320.1 |
| 6,914,128 B1 | 7/2005 | Salfeld et al. | 530/387.3 |
| 6,992,235 B2 | 1/2006 | Bode et al. | |
| 6,998,514 B2 | 2/2006 | Brüggemann | 800/18 |
| 7,105,348 B2 | 9/2006 | Murphy et al. | |
| 7,119,248 B1 | 10/2006 | Rajewsky et al. | 800/6 |
| 7,205,140 B2 | 4/2007 | Gottschalk et al. | |
| 7,205,148 B2 | 4/2007 | Economides et al. | 435/462 |
| 7,294,754 B2 | 11/2007 | Poueymirou et al. | |
| 7,435,871 B2 | 10/2008 | Green et al. | 800/18 |
| 7,501,552 B2 | 3/2009 | Lonberg et al. | 800/6 |
| 7,605,237 B2 | 10/2009 | Stevens et al. | |
| 7,605,238 B2 | 10/2009 | Korman et al. | |
| 7,910,798 B2 | 3/2011 | Tanamachi et al. | 800/18 |
| 7,932,431 B2 | 4/2011 | Bruggemann | |
| 8,158,419 B2 | 4/2012 | Lonberg et al. | 435/328 |
| 8,502,018 B2 | 8/2013 | Murphy et al. | 800/18 |
| 8,592,644 B2 | 11/2013 | Harriman et al. | |
| 8,642,835 B2 | 2/2014 | MacDonald et al. | |
| 8,697,940 B2 | 4/2014 | MacDonald et al. | |
| 8,754,287 B2 | 6/2014 | MacDonald et al. | |
| 8,791,323 B2 | 7/2014 | Murphy et al. | |
| 8,877,901 B2 | 11/2014 | Govindan | |
| 9,253,965 B2 | 2/2016 | Lang et al. | |
| 9,434,782 B2 | 9/2016 | Bradley et al. | |
| 9,445,581 B2 | 9/2016 | Bradley et al. | |
| 9,447,177 B2 | 9/2016 | Bradley et al. | |
| 9,504,236 B2 | 11/2016 | Bradley et al. | |
| 9,505,827 B2 | 11/2016 | Bradley et al. | |
| 2002/0088016 A1 | 7/2002 | Bruggemann | 800/18 |
| 2002/0183275 A1* | 12/2002 | Murphy | |
| 2003/0108925 A1 | 6/2003 | Dix et al. | 435/6 |
| 2003/0217373 A1 | 11/2003 | Green et al. | 800/6 |
| 2004/0128703 A1 | 7/2004 | Shizuya | |
| 2004/0231012 A1 | 11/2004 | Bruggemann | |
| 2005/0048621 A1 | 3/2005 | Grasso et al. | 435/69.1 |
| 2006/0015949 A1 | 1/2006 | Lonberg et al. | |
| 2006/0015957 A1 | 1/2006 | Lonberg et al. | |
| 2006/0021074 A1 | 1/2006 | Kellermann et al. | 800/18 |
| 2006/0199204 A1 | 9/2006 | Dix et al. | 800/16 |
| 2007/0280945 A1 | 12/2007 | Stevens et al. | 424/145.1 |
| 2008/0098490 A1 | 4/2008 | Jakobovits et al. | |
| 2009/0083870 A1 | 3/2009 | Horn et al. | 800/13 |
| 2009/0083879 A1 | 3/2009 | Dhugga | |
| 2009/0093059 A1 | 4/2009 | Baszczynski et al. | |
| 2009/0196112 A1 | 8/2009 | Cho | 365/200 |
| 2009/0209036 A1 | 8/2009 | Reynaud et al. | 435/455 |
| 2009/0307787 A1 | 12/2009 | Grosveld et al. | |
| 2010/0011450 A1 | 1/2010 | Garcia et al. | |
| 2010/0069614 A1 | 3/2010 | Houtzager et al. | 530/387.1 |
| 2010/0146647 A1 | 6/2010 | Logtenberg et al. | 800/4 |
| 2010/0196367 A1 | 8/2010 | Day | 424/130.1 |
| 2010/0330676 A1 | 12/2010 | Horowitz et al. | |
| 2011/0119779 A1 | 5/2011 | Shizuya et al. | |
| 2011/0138489 A1 | 6/2011 | Tanamachi et al. | |
| 2011/0145937 A1† | 6/2011 | MacDonald | |
| 2011/0195454 A1 | 8/2011 | McWhirter et al. | |
| 2011/0236378 A1 | 9/2011 | Green et al. | 424/133.1 |
| 2011/0283376 A1 | 11/2011 | Murphy et al. | |
| 2012/0070861 A1 | 3/2012 | Macdonald et al. | 435/91.1 |
| 2012/0073004 A1 | 3/2012 | MacDonald et al. | |
| 2012/0096572 A1 | 4/2012 | MacDonald et al. | |
| 2012/0167237 A1 | 6/2012 | Bradley et al. | 800/9 |
| 2012/0195910 A1 | 8/2012 | Wu et al. | |
| 2012/0204278 A1 | 8/2012 | Bradley et al. | 800/18 |
| 2012/0233715 A1 | 9/2012 | Kuroiwa et al. | 800/3 |
| 2012/0322108 A1 | 12/2012 | Macdonald et al. | 435/69.6 |
| 2013/0039850 A1 | 2/2013 | Lonberg et al. | 424/1.49 |
| 2013/0096287 A1 | 4/2013 | MacDonald et al. | |
| 2013/0102031 A1 | 4/2013 | King et al. | 435/69.6 |
| 2013/0160153 A1 | 6/2013 | MacDonald et al. | |
| 2013/0198879 A1 | 8/2013 | McWhirter et al. | |
| 2013/0212719 A1 | 8/2013 | MacDonald et al. | |
| 2013/0247235 A1 | 9/2013 | McWhirter et al. | |
| 2013/0254911 A1 | 9/2013 | MacDonald et al. | |
| 2013/0263293 A1 | 10/2013 | Bradley et al. | |
| 2013/0323790 A1 | 12/2013 | MacDonald et al. | |
| 2013/0323791 A1 | 12/2013 | MacDonald et al. | |
| 2013/0326647 A1 | 12/2013 | MacDonald et al. | |
| 2013/0333057 A1 | 12/2013 | MacDonald et al. | |
| 2014/0017228 A1 | 1/2014 | MacDonald et al. | |
| 2014/0041067 A1 | 2/2014 | Bradley et al. | |
| 2014/0120582 A1 | 5/2014 | Bradley et al. | |
| 2014/0130193 A1 | 5/2014 | MacDonald et al. | |
| 2014/0130194 A1 | 5/2014 | MacDonald et al. | |
| 2014/0137275 A1 | 5/2014 | MacDonald et al. | |
| 2014/0150125 A1 | 5/2014 | Bradley et al. | |
| 2014/0150126 A1 | 5/2014 | Bradley et al. | |
| 2014/0182003 A1 | 6/2014 | Bradley et al. | |
| 2014/0201854 A1 | 7/2014 | Bradley et al. | |
| 2014/0201856 A1 | 7/2014 | Bradley et al. | |
| 2014/0212416 A1 | 7/2014 | Friedrich et al. | |
| 2014/0213773 A1 | 7/2014 | MacDonald et al. | |
| 2014/0283150 A1 | 9/2014 | Bradley et al. | |
| 2014/0323327 A1 | 10/2014 | Bradley et al. | |
| 2014/0325690 A1 | 10/2014 | Bradley et al. | |
| 2014/0331339 A1 | 11/2014 | Bradley et al. | |
| 2014/0331343 A1 | 11/2014 | Bradley et al. | |
| 2014/0331344 A1 | 11/2014 | Friedrich et al. | |
| 2014/0359797 A1 | 12/2014 | Bradley et al. | |
| 2015/0033369 A1 | 1/2015 | Bradley et al. | |
| 2015/0033372 A1 | 1/2015 | Bradley et al. | |
| 2015/0037337 A1 | 2/2015 | Friedrich et al. | |
| 2015/0040250 A1 | 2/2015 | Bradley et al. | |
| 2015/0113669 A1 | 4/2015 | Bradley et al. | |
| 2015/0133641 A1 | 5/2015 | Germaschewski et al. | |
| 2015/0196015 A1 | 7/2015 | MacDonald et al. | |
| 2015/0334998 A1 | 11/2015 | Bradley et al. | |
| 2016/0044900 A1 | 2/2016 | Bradley et al. | |
| 2016/0150768 A1 | 6/2016 | Bradley et al. | |
| 2016/0219846 A1 | 8/2016 | Liang | |
| 2016/0249592 A1 | 9/2016 | Bradley et al. | |
| 2016/0345551 A1 | 12/2016 | Bradley et al. | |
| 2016/0345552 A1 | 12/2016 | Bradley et al. | |
| 2016/0353719 A1 | 12/2016 | Friedrich et al. | |
| 2017/0051045 A1 | 2/2017 | Bradley et al. | |
| 2017/0071174 A1 | 3/2017 | Bradley et al. | |
| 2017/0081423 A1 | 3/2017 | Bradley et al. | |
| 2017/0094956 A1 | 4/2017 | Bradley et al. | |
| 2017/0096498 A1 | 4/2017 | Bradley et al. | |
| 2017/0099815 A1 | 4/2017 | Bradley et al. | |
| 2017/0099816 A1 | 4/2017 | Bradley et al. | |
| 2017/0099817 A1 | 4/2017 | Bradley et al. | |
| 2017/0101482 A1 | 4/2017 | Bradley et al. | |
| 2017/0101483 A1 | 4/2017 | Bradley et al. | |
| 2017/0105396 A1 | 4/2017 | Bradley et al. | |
| 2017/0135327 A1 | 5/2017 | Lee | |
| 2017/0320936 A1 | 11/2017 | Bradley et al. | |
| 2017/0354131 A1 | 12/2017 | Bradley et al. | |
| 2018/0030121 A1 | 2/2018 | Bradley et al. | |

FOREIGN PATENT DOCUMENTS

| | | | |
|---|---|---|---|
| DE | 10251018 A1 | 5/2004 | |
| EP | 1780272 A1 | 5/2007 | C12N 15/00 |
| EP | 0937140 B1 | 9/2007 | |
| EP | 2517557 A2 | 10/2012 | |
| EP | 2550363 | 10/2012 | C12N 15/85 |
| EP | 2480676 B1 | 4/2016 | |
| GB | 2398784 A | 9/2004 | A01K 67/027 |
| GB | 2403475 A | 1/2005 | |
| KR | 1020050042792 A | 5/2005 | A01K 67/027 |
| WO | WO-9004036 A1 | 4/1990 | |
| WO | WO-9100906 A1 | 1/1991 | |
| WO | WO 1991/10741 | 7/1991 | C12P 21/06 |
| WO | WO-9312227 A1 | 6/1993 | |
| WO | WO-9402602 A1 | 2/1994 | |
| WO | WO-9404667 A1 | 3/1994 | |
| WO | WO-9425585 A1 | 11/1994 | |
| WO | WO-9630498 A1 | 10/1996 | |

(56) References Cited

FOREIGN PATENT DOCUMENTS

| | | | |
|---|---|---|---|
| WO | WO 1998/24884 | 6/1998 | ............... C12N 5/00 |
| WO | WO-9824893 A2 | 6/1998 | |
| WO | WO-9945962 A1 | 9/1999 | |
| WO | WO-0026373 A1 | 5/2000 | |
| WO | WO 2002/08409 A2 | 1/2002 | ............ C12N 15/00 |
| WO | WO-0236789 A2 | 5/2002 | |
| WO | WO 2002/043478 | 6/2002 | .......... A01K 67/027 |
| WO | WO 02/053596 A2 | 7/2002 | ............. C07K 16/28 |
| WO | 02/066630 A1 † | 8/2002 | |
| WO | WO 2002/059263 | 8/2002 | |
| WO | WO-02066630 A1 | 8/2002 | |
| WO | WO 2002/070648 A2 | 9/2002 | |
| WO | WO 2003/006639 A1 | 1/2003 | ............... C12N 5/10 |
| WO | WO 2003/047336 A2 | 6/2003 | |
| WO | WO 2003/061363 A2 | 7/2003 | |
| WO | WO 2004/050838 A2 | 6/2004 | |
| WO | WO 2005/003364 A1 | 1/2005 | ............. C12N 15/90 |
| WO | WO-2005004592 A2 | 1/2005 | |
| WO | WO 2005/019463 A1 | 3/2005 | ............. C12N 15/85 |
| WO | WO-2005058815 A2 | 6/2005 | |
| WO | WO-2005092926 A2 | 10/2005 | |
| WO | WO-2006008548 A2 | 1/2006 | |
| WO | WO 2006/044492 | 4/2006 | ............. C12N 15/52 |
| WO | WO-2006055704 A2 | 5/2006 | |
| WO | WO-2006068953 A2 | 6/2006 | |
| WO | WO 2006/122442 A1 | 11/2006 | ............... C12N 9/22 |
| WO | WO 2007/096779 A2 | 8/2007 | |
| WO | WO-2007085837 A1 | 8/2007 | |
| WO | WO-2007117410 A2 | 10/2007 | |
| WO | WO-2007143168 A2 | 12/2007 | |
| WO | WO-2008022391 A1 | 2/2008 | |
| WO | WO 2008/054606 A2 | 5/2008 | ............. C07K 16/00 |
| WO | WO 2008/070367 A2 | 6/2008 | ............. C12N 15/09 |
| WO | WO-2008076379 A2 | 6/2008 | |
| WO | WO-2008081197 A1 | 7/2008 | |
| WO | WO 2008/094178 A2 | 8/2008 | ............... C12Q 1/68 |
| WO | WO 2008/103474 A1 | 8/2008 | ............. C12N 15/13 |
| WO | WO 2008/118970 A2 | 10/2008 | ............. A61K 48/00 |
| WO | WO 2008/122886 A2 | 10/2008 | ............. C12N 15/85 |
| WO | WO 2008/151081 A1 | 12/2008 | ............. C12N 15/13 |
| WO | WO-2009013620 A2 | 1/2009 | |
| WO | WO 2009/018411 A1 | 2/2009 | ............. C07K 16/28 |
| WO | WO 2009/023540 A1 | 2/2009 | ............ A61K 39/395 |
| WO | WO-2009076464 A2 | 6/2009 | |
| WO | WO 2009/080254 A1 | 7/2009 | ............. C07K 16/46 |
| WO | WO 2009/094178 A2 | 7/2009 | ............. C09B 67/08 |
| WO | WO-2009097006 A2 | 8/2009 | |
| WO | WO-2009118524 A2 | 10/2009 | |
| WO | WO-2009129247 A2 | 10/2009 | |
| WO | WO-2009143472 A2 | 11/2009 | |
| WO | WO 2009/157771 A2 | 12/2009 | .......... A01K 67/027 |
| WO | 2010/039900 A2 † | 4/2010 | |
| WO | WO 2010/039900 A2 | 4/2010 | ............. C12N 15/13 |
| WO | WO 2010/070263 A1 | 6/2010 | ............. C12N 15/85 |
| WO | WO-2010077854 A1 | 7/2010 | |
| WO | WO 2010/097385 A1 | 9/2010 | ............. C07K 16/24 |
| WO | WO-2010109165 A2 | 9/2010 | |
| WO | WO 2010/113039 A1 | 10/2010 | ............... C12N 5/00 |
| WO | WO 2011/004192 A1 | 1/2011 | .......... A01K 67/027 |
| WO | WO 2011/008093 A1 | 1/2011 | ............. C07K 16/00 |
| WO | WO-2011014469 A1 | 2/2011 | |
| WO | WO 2011/056864 A1 | 5/2011 | ............. C12P 21/06 |
| WO | WO-2011062206 A1 | 5/2011 | |
| WO | WO-2011062207 A1 | 5/2011 | |
| WO | WO-2011071957 A1 | 6/2011 | |
| WO | WO-2011072204 A1 | 6/2011 | |
| WO | WO 2011/097603 A1 | 8/2011 | ............. C12N 15/85 |
| WO | WO-2011146121 A1 | 11/2011 | |
| WO | WO 2011/158009 A1 | 12/2011 | .......... A01K 67/027 |
| WO | WO 2011/163311 A1 | 12/2011 | ............. C12N 15/85 |
| WO | WO 2011/163314 A1 | 12/2011 | ............. C12N 15/85 |
| WO | WO 2012/018764 A1 | 2/2012 | ............. C12N 15/85 |
| WO | WO 2012/023053 A2 | 2/2012 | |
| WO | WO-2012064682 A1 | 5/2012 | |
| WO | WO 2012/141798 A1 | 10/2012 | ............. C12N 15/85 |
| WO | WO 2012/148873 A2 | 11/2012 | .......... A01K 67/027 |
| WO | WO 2013/022782 A1 | 2/2013 | ............. C12N 15/85 |
| WO | WO 2013/041844 A2 | 3/2013 | ............. C12N 15/85 |
| WO | WO 2013/041845 A2 | 3/2013 | ............. C12N 15/85 |
| WO | WO-2013041846 A2 | 3/2013 | |
| WO | WO 2013/059230 A1 | 4/2013 | ............. C12N 15/85 |
| WO | WO-2013045916 A1 | 4/2013 | |
| WO | WO 2013/061098 A2 | 5/2013 | ............. C12N 15/85 |
| WO | WO-2013061078 A1 | 5/2013 | |
| WO | WO 2013/096142 | 6/2013 | .......... A01K 67/027 |
| WO | WO-2013079953 A1 | 6/2013 | |
| WO | WO 2013/116609 A1 | 8/2013 | .......... A01K 67/027 |
| WO | WO-2013134263 A1 | 9/2013 | |
| WO | WO-2013144567 A1 | 10/2013 | |
| WO | WO-2013166236 A1 | 11/2013 | |
| WO | WO-2013171505 A2 | 11/2013 | |
| WO | WO-2013176772 A1 | 11/2013 | |
| WO | WO-2014093622 A2 | 6/2014 | |
| WO | WO-2015049517 A2 | 4/2015 | |

OTHER PUBLICATIONS

Baker A.M., et al., "Adaptation of TCR Expression Vectors for the Construction of Mouse-Human Chimeric MBP-Specific TCR Transgenes," *Journal of Neuroscience Research*, vol. 45 Issue No. 4, pp. 487-491, 1996.

Beerli, R. et al., "Mining Human Antibody Repertoires," *MAbs*, vol. 2, Issue No. 4, pp. 365-378, Jul./Aug. 2010.

Bhattacharya P., et al., "Switch Region Identity Plays an Important Role in Ig Class Switch Recombination," *Journal of Immunology*, vol. 184, Issue No. 11, pp. 6242-6248, 2010.

Blankenstein T. et al., "Immunoglobulin VH Region Genes of the Mouse are Organized in Overlapping Clusters," *European Journal of Immunology*, vol. 17, Issue No. 9, pp. 1351-1357, 1987.

Bode J., et al., "The Transgeneticist'S Toolbox: Novel Methods for the Targeted Modification of Eukaryotic Genomes," *Biological Chemistry*, vol. 381, Issue Nos. 9-10, pp. 801-813, 2000.

Bogen B., et al., "A Rearranged λ2 Light Gene Chain Retards but does not Exclude χ and λ1 Expression," European Journal of Immunology, vol. 21, Issue No. 10, pp. 2391-2395, 1991.

Bransteitter R., et al., "Activation-Induced Cytidine Deaminase Deaminates Deoxycytidine on Single-Stranded DNA but Requires the Action of RNase," *Proceedings of the National Academy of Sciences*, vol. 100, Issue No., pp. 4102-4107, 2003.

Brezinschek H.P., et al., "Analysis of the Human VH Gene Repertoire," *Journal of Clinical Investigation*, vol. 99, Issue No. 10, pp. 2488-2501, 1997.

Brüggemann M., et al., "Human Monoclonal Antibodies from Translocus Mice," *Molecular Biology of B Cells*, Chapter 34, pp. 547-561, 2003.

Brüggemann M., et al., "The Immunogenicity of Chimeric Antibodies," *The Journal of Experimental Medicine*, vol. 170, Issue No. 6, pp. 2153-2157, 1989.

Brüggemann M., et al., "Strategies for Expressing Human Antibody Repertoires in Transgenic Mice," *Immunology Today*, vol. 17, Issue No. 8, pp. 391-397, 1996.

Butler J., et al., "Immunoglobulin Diversity, B-Cell and Antibody Repertoire Development in Large Farm Animals," *Revue scientifique et technique (International Office of Epizootics)*, vol. 17, Issue No. 7, pp. 43-70, 1998.

Casrouge, A., et al., "Size Estimate of the αβ TCR Repertoire of Naïve Mouse Splenocytes," *Journal of Immunology*, vol. 164, Issue No. 11, pp. 5782-5787, 2000.

Chan, A. et al., "Therapeutic Antibodies for Autoimmunity and Inflammation," *Nature Reviews Immunology*, vol. 10, Issue No. 5, pp. 301-316, 2010.

Chen, Y. et al., "PiggyBac Transposon-Mediated, Reversible Gene Transfer in Human Embryonic Stem Cells," *Stem Cells and Development*, vol. 19, Issue No. 6, pp. 763-771, Sep. 2009.

Clark M., "IgG Effector Mechanisms," *Chemical Immunology*, vol. 65, pp. 88-110, 1997.

Corbett S., et al., "Sequence of the Human Immunoglobulin Diversity (D) Segment Locus: a Systematic Analysis Provides no Evi-

(56) References Cited

OTHER PUBLICATIONS dence for the Use of DIR Segments, Inverted D Segments, "minor" D Segments or D-D Recombination," *Journal of Molecular Biology*, vol. 270, Issue No. 4, pp. 587-597, 1997.

Crouch, E. et al., "Regulation of AID expression in the immune response," *Journal of Experimental Medicine*, vol. 204, Issue No. 5, pp. 1145-1156, Apr. 2007.

Davies N., et al., "Creation of Mice Expressing Human Antibody Light Chains by Introduction of a Yeast Artificial Chromosome Containing the Core Region of the Human Immunoglobulin 1 Locus," *Nature Biotechnology*, vol. 11, Issue No. 8, pp. 911-914, 1993.

De Bono B., et al., "VH Gene Segments in the Mouse and Human Genomes," *Journal of Molecular Biology*, vol. 342, Issue No, 1, pp. 131-143, 2004.

Deng C., et al., "Reexamination of Gene Targeting Frequency as a Function of the Extent of Homology Between the Targeting Vector and the Target Locus," *Molecular and Cellular Biology*, vol. 12, Issue No. 8, pp. 3365-3371, 1992.

Ebert, A. et al., "The Distal V(H) Gene Cluster of the IgH Locus Contains Distinct Regulatory Elements with Pax5 Transcription Factor-Dependent Activity in Pro-B Cells," *Immunity*, vol. 34 Issue No. 2, pp. 175-187, 2011.

Feng Y., et al., "Site-Specific Chromosomal Integration in Mammalian Cells: Highly Efficient Cre Recombinase-Mediated Cassette Exchange," *Journal of Molecular Biology*, vol. 292, Issue No. 4, pp. 779-785, 1999.

Fleischer B., et al., "Reactivity of Mouse T-Cell Hybridomas Expressing Human Vbeta Gene Segments With Staphylococcal and Streptococcal Superantigens," *Infection and Immunity*, vol. 64, vol. 3, pp. 987-994, 1996.

Friedrich, G., Declaration of Glenn Friedrich, 4 pages, dated Mar. 3, 2016.

Fujieda S., et al., "Multiple Types of Chimeric Germ-Line Ig Heavy Chain Transcripts in Human B Cells: Evidence for Trans-Splicing of Human Ig RNA," *Journal of Immunology*, vol. 157, Issue No. 8, pp. 3450-3459, 1996.

Gallo M., "The Human Immunoglobulin Loci Introduced into Mice: V (D) and J Gene Segment Usage Similar to that of Adult Humans," European Journal of Immunology, vol. 30, Issue No. 2, pp. 534-540, 2000.

Gama Sosa M, et al., "Animal Transgenesis: An Overview," *Brain Structure and Function*, vol. 214, Issue Nos. 2-3, pp. 91-109, 2010.

Gavilondo J., "Antibody Engineering at the Millennium," *BioTechniques*, vol. 29, Issue No. 1, pp. 128-145, 2000.

Genbank, Accession No. AC111740, "Rattus norvegicus clone CH230-30N12, * Sequencing in Progress *, 6 unordered pieces", 42 pages, Nov. 2002. [XP55054806 [online] [retrieved on Feb. 28, 2013]. Retrieved from the Internet: <http:>.</http:>.].

Genbank, Accession No. KF698731.1, 1 page, accessed Nov. 18, 2013.

Genbank, Accession No. x97051.1 S64822, DNA Sequence of the Human Immunoglobulin D Segment Locus, 26 pages, Mar. 3, 2015.

Genbank, Accession No. NT 114985, "Mus Musculus Strain 129S1/SvImJ Chromosome 12 Genomic Sca Locus Group 129S1/SVIMJ_MMCHR12_CTG1," 1 page, Dec. 27, 2013.

Giraldo P., et al., "Size Matters: Use of Yacs, Bacs and Pacs in Transgenic Animals," *Transgenic Research*, vol. 10, Issue No. 2, pp. 83-103, 2001.

Giusti A., et al., "Hypermutation is Observed only in Antibody H Chain V Region Transgenes that have Recombined with Endogenous Immunoglobulin H DNA: Implications for the Location of Cis-Acting Elements Required for Somatic Mutation," *The Journal of Experimental Medicine*, vol. 177, Issue No. 3, pp. 797-809, 1993.

Glanville J., et al., "Naive Antibody Gene-Segment Frequencies are Heritable and Unaltered by Chronic Lymphocyte Ablation," *Proceedings of the National Academy of Sciences U.S.A*, vol. 108, Issue No. 50, pp. 20066-20071, 2011.

Goldman, I. et al., "Transgenic animals in medicine: Integration and expression of foreign genes, theoretical and applied aspects," *Medical Science Monitor*, vol. 10, Issue No. 11, pp. RA274-RA285, 2004.

Green L., et al., "Antigen-Specific Human Monoclonal Antibodies from Mice Engineered with Human Lg Heavy and Light Chain YACs," *Nature Genetics*, vol. 7, Issue No. 1, pp. 13-21, 1994.

Green L., et al., "Regulation of B Cell Development by Variable Gene Complexity in Mice Reconstituted with Human Immunoglobulin Yeast Artificial Chromosomes," *The Journal of Experimental Medicine*, vol. 188, Issue No. 3, pp. 483-495, 1998.

Guirouilh-Barbat J. et al., "Is homologous recombination really an error-free process?," *Frontiers in Genetics*, vol. 5, Issue No. 175, 15 pages, Jun. 2014.

Harding F., et al., "Class Switching in Human Immunoglobulin Transgenic Mice," *Annals of the New York Academy of Sciences*, vol. 764, pp. 536-546, 1995.

Hewitt, S. et al., "Association Between the Igk and Igh immunoglobulin loci mediated by the 3' Igk enhancer induces 'decontraction' of the Igh locus in pre-B cells," *Nature Immunology*, vol. 9 Issue No. 4, pp. 396-404, 2008.

Houdebine, L., "The methods to generate transgenic animals and to control transgene expression," *Journal of Biotechnology*, vol. 98, Issue Nos. 2-3, pp. 145-160, 2002.

Houdebine, L., "Transgenic Animal Models in Biomedical Research," Chapter 10, *Methods in Molecular Biology*, vol. 360, pp. 163-202, 2007.

Houldsworth J., et al., "Comparative Genomic Hybridization: An Overview," *The American Journal of Pathology*, vol. 145, Issue No. 6, pp. 1253-1260, 1994.

Huber V., et al., "Distinct Contributions of Vaccine-Induced Immunoglobulin G1 (IgG1) and IgG2a Antibodies to Protective Immunity Against Influenza," *Clinical and Vaccine Immunology*, vol. 13, Issue No. 9, pp. 981-990, 2006.

Jakobovits A., "Production of Fully Human Antibodies by Transgenic Mice," *Current Opinion in Biotechnology*, vol. 6, Issue No. 5, pp. 561-566, 1995.

Jakobovits A., "The Long-Awaited Magic Bullets: Therapeutic Human Monoclonal Antibodies from Transgenic Mice," *Expert Opinion Investigational Drugs*, vol. 7, Issue No. 4, pp. 607-614, 1998.

Janeway, Jr., C. et al., "The Rearrangement of Antigen-Receptor Gene Segments Controls Lymphocyte Development," *In Immunobiology*, 5th Edition, 13 pages, Aug. 2015 [retrieved from the Internet: <http: />].

Janeway et al., "Structural Variation in Immunoglobulin Constant Regions," Immuobioloay: *The Immune System in Health and Disease*, 5th Edition, 5 pages, 2001.

Jessen K., et al., "Molecular Analysis of Metastasis in a Polyomavirus Middle T Mouse Model: the Role of Osteopontin," *Breast Cancer Research*, vol. 6, Issue No. 3, pp. R157-R169, 2004.

Johnston C., et al., "Complete Sequence Assembly and Characterization of the C57BL/6 Mouse Lg Heavy Chain V Region," *The Journal of Immunology*, vol. 176, Issue No. 7, pp. 4221-4234, 2006.

Karu A., et al., "Recombinant Antibody Technolgy," *ILAR Journal* / National Research Council, Institute of Laboratory Animal Resources, vol. 37, Issue No. 3, pp. 132-141, 1995.

Kaushik A., et al., "Novel Insight into Antibody Diversification from Cattle," *Veterinary Immunology and Immunopathology*, vol. 87, Issue Nos. 3-4, pp. 347-350, 2002.

Kenter A., et al., "Three-Dimensional Architecture of the IgH Locus Facilitates Class Switch Recombination," *Annals of the New York Academy of Sciences*, vol. 1267, pp. 86-94, 2012.

Kondo, S. et al., "Highly Improved Gene Targeting by Germline-Specific Cas9 Expression in *Drosophila*," *Genetics*, vol. 195, pp. 715-721, Nov. 2013.

Kondo, S. et al., "Highly Improved Gene Targeting by Germline-Specific Cas9 Expression in *Drosophila*," *Genetics*, vol. 195, pp. 715-721, Nov. 2013 (Abstract—1 page.).

Kouskoff V., et al., "Cassette Vectors Directing Expression of T Cell Receptor Genes in Transgenic Mice," *Journal of Immunological Methods*, vol. 180, Issue No. 2, pp. 273-280, 1995.

(56) References Cited

OTHER PUBLICATIONS

Kuraoka M., et al., "Aid expression during B-cell development: searching for answers," *Immunologic Research*, vol. 49, Issue Nos. 1-3, pp. 3-13, 2011.
Laffleur, B. et al., Chapter 9, "Production of Human or Humanized Antibodies in Mice," *Methods in Molecular Biology*, vol. 901, pp. 149-159, 2012.
Lee E., et al., "Complete Humanization of the Mouse Immunoglobulin Loci Enables Efficient Therapeutic Antibody Discovery," *Nature Biotechnology*, vol. 32, Issue No. 4, pp. 356-363, 2014.
Lee, E. et al., Chapter 8, "The Application of Transgenic Mice for Therapeutic Antibody Discovery," *Methods in Molecular Biology*, vol. 901, pp. 137-148, 2012.
LeFranc, M. et al., "The Immunoglobulin Facts Book," Academic Press, ISBN:978-0-08-057447, 428 pages, May 2001.
LeFranc M., et al., "Nomenclature of the Human Immunoglobulin Heavy (IGH) Genes," *Experimental and Clinical Immunogenetics*, vol. 18, Issue No. 2, pp. 100-116, 2001.
LeFranc, M., "Nomenclature of the Human Immunoglobulin Kappa (IGK) Genes," *Experimental and Clinical Immunogenetics*, vol. 18, Issue No. 3, pp. 161-174, 2001.
LeFranc M., "Nomenclature of the Human Immunoglobulin Lambda (IGL) Genes," *Experimental and Clinical Immunogenetics*, vol. 18, Issue No. 4, pp. 242-254, 2001.
Li, H. et al., "Genetic diversity of the human immunoglobulin heavy chain V(H) region," *Immunological Reviews*, vol. 190, pp. 53-68, 2002.
Little M., et al., "Generation of a Large Complex Antibody Library from Multiple Donors," *Journal of Immunological Methods*, vol. 231, Issue Nos. 1-2, pp. 3-9, 1999.
Lonberg, N., "Fully human antibodies from transgenic mouse and phage display platforms," *Current Opinion in Immunology*, vol. 20, Issue No. 4, pp. 450-459, 2008.
Ma B., et al., "Human Antibody Expression in Transgenic Rats: Comparison of Chimeric IgH Loci with Human VH, D and JH but Bearing Different Rat C-Gene Regions," *Journal of Immunological Methods*, vol. Nos. 400-401, pp. 78-86, 2013.
MacDonald L., et al., "Velocigene Technology Extended to Humanization of Several Megabases of Complex Gene Loci," (Abstract—21) 1st International MUGEN Conference on Animal Models for Human Immunological Disease, Athens Greece, 1 page, Sep. 10-13, 2006.
MacDonald, L. et al., Poster: "VelociGene® Technology Extended to Humanization of Several Megabases of Complex," Exhibit IJR-47 to Jeffrey Rourke Declaration, 1 page, 2006.
MacDonald, L. et al., Expanded Poster: "VelociGene® Technology Extended to Humanization of Several Megabases of Complex," Exhibit IJR-49 to Jeffrey Rourke Declaration, 6 pages, 2006.
MacDonald, Lynn E., "Curriculum Vitae of Lynn E. MacDonald, Ph.D.," 3 pages.
MacDonald, Lynn E., Declaration of Lynn E. MacDonald with Exhibits, dated Feb. 3, 2015, relating to International Application No. PCT/US02/04500, 13 pages (Published as WO02/066630 A1).
Magadán, S. et al., "Production of Antigen-Specific Human Monoclonal Antibodies: Comparison of Mice Carrying IgH/kappa or IgH/kappa/lambda Transloci," *Bio Techniques*, vol. 33, Issue No. 3, pp. 680, 682, 684 passim, Sep. 2002.
Martinez-Jean, C. et al., "Nomenclature and Overview of the Mouse (*Mus musculus* and *Mus.* sp.) Immunoglobulin Kappa (IGK) Genes," *Experimental and Clinical Immunogenetics*, vol. 18, pp. 255-279, 2001.
Matthews V., et al., "A Locus Affecting Immunoglobulin Isotype Selection (Igis1) Maps to the MHC Region in C57BL, BALB/c and NOD Mice," *Immunology and Cell Biology*, vol. 79, Issue No. 6, pp. 576-582, 2001.
McMurry M., et al., "Enhancer Control of Local Accessibility to V(D)J Recombinase," *Molecular and Cellular Biology*, vol. 17, Issue No. 8, pp. 4553-4561, 1997.

Monaco A., et al., "YACs, BACs, PACs and MACs: Artificial Chromosomes as Research Tools," *Trends in Biotechnology*, vol. 12, Issue No. 7, pp. 280-286, 1994.
Müller U., "Ten Years of Gene Targeting: Targeted Mouse Mutants, from Vector Design to Phenotype Analysis," *Mechanisms of Development*, vol. 82, Issue Nos. 1-2, pp. 3-21, 1999.
Muyrers J., et al., "Rapid Modification of Bacterial Artificial Chromosomes by ET-Recombination," *Nucleic Acids Research*, vol. 27, Issue No. 6, pp. 1555-1557, 1999.
Narayanan K., et al., "Efficient and Precise Engineering of a 200 kb Beta-Globin Human/Bacterial Artificial Chromosome in *E. Coli* DH10B using an Inducible Homologous Recombination System," *Gene Therapy*, vol. 6, Issue No. 3, pp. 442-447, 1999.
Neuberger M.S., et al., "Isotype Exclusion and Transgene Down-Regulation in Immunoglobulin-Lambda Transgenic Mice," *Nature*, vol. 338, Issue No. 6213, pp. 350-352, 1989.
Parng C.L., et al., "Gene Conversion Contributes to LG Light Chain Diversity in Cattle," *Journal of Immunology*, vol. 157, Issue No. 12, pp. 5478-5486, 1996.
Qi N., et al., "A New Transgenic Rat Model of Hepatic Steatosis and the Metabolic Syndrome," *Hypertension*, vol. 45, Issue No. 5, pp. 1004-1011, 2005.
Ramïrez-Solis R., et al., "Chromosome Engineering in Mice," *Nature*, vol. 378, Issue No. 6558, pp. 720-724, 1995.
Ramsden D., et al., "Conservation of Sequence in Recombination Signal Sequence Spacers," *Nucleic Acids Research*, vol. 22, Issue No. 10, pp. 1785-1796, 1994.
Regeneron Pharmaceuticals, Inc., "AstraZeneca Licenses Regeneron's VelocImmune® Technology for Discovering Human Monoclonal Antibodies—AstraZeneca Is First Licensee of Novel VelocImmune Technology License Fees Total up to $120 Million Over Six Years," 2 pages, Feb. 5, 2007.
Regeneron Pharmaceuticals, Inc., "Astellas Licenses Regeneron's Velocimmune® Technology for Discovering Human Monoclonal Antibodies," 2 pages, Mar. 30, 2007.
Regeneron Pharmaceuticals, Inc., "Regeneron Initiates Major Global Collaboration with Sanofi-aventis to Develop and Commercialize Fully-Human Therapeutic Antibodies," 2 pages, Nov. 29, 2007.
Rourke, J., "Declaration of Jeffrey Rourke, Registered Patent Attorney for Regeneron Pharmaceuticals, Inc.—In the matter of Patent Acceptance 2011266843 in the Name of Kymab Limited and in the matter of Opposition thereto by Regeneron Pharmaceuticals, Inc.," 5 pages, dated Jan. 29, 2016.
Ren S., et al., "Targeted Insertion Results in a Rhombomere 2-Specific Hoxa2 Knockdown and Ectopic Activation of Hoxa1 Expression," *Developmental Dynamics*, vol. 225, Issue No. 3, pp. 305-315, 2002.
Ristevski S., et al., "Making Better Transgenic Models: Conditional, Temporal, and Spatial Approaches," *Molecular Biotechnology*, vol. 29, Issue No. 2, pp. 153-163, 2005.
Rosner K., et al., "Third Complementarity-Determining Region of Mutated VH Immunoglobulin Genes Contains Shorter V, D, J, P, and N Components than Non-Mutated Genes," *Immunology*, vol. 103, Issue No. 2, pp. 179-187, 2001.
Rusk., et al., "Making Mice at High Speed," *Nature Methods*, vol. 4, Issue No. 3, pp. 196-197, 2007.
Scapini P., et al., "Myeloid Cells, BAFF, and IFN-Gamma Establish an Inflammatory Loop that Exacerbates Autoimmunity in Lyn-Deficient Mice," *The Journal of Experimental Medicine*, vol. 207, Issue No. 8, pp. 1757-1773, 2010.
Seidl K., et al., "An Expressed Neo(r) Cassette Provides Required Functions of the 1gamma2b Exon for Class Switching," *International Immunology*, vol. 10, Issue No. 11, pp. 1683-1692, 1998.
Seidl K., et al., "Position-Dependent Inhibition of Class-Switch Recombination by PGK-Neor Cassettes Inserted into the Immunoglobulin Heavy Chain Constant Region Locus," *Proceedings of the National Academy of Sciences of the U.S.A.*, vol. 96, Issue No. 6, pp. 3000-3005, 1999.
Sekiguchi J. et al., "The Mechanism of V(D)J Recombination," *Molecular Biology of B Cells*, Chapter 5, pp. 61-82, 2004.
Shi Y., et al., "The Mapping of Transgenes by Fluorescence in Situ Hybridization on G-Banded Mouse Chromosomes," *Mammalian Genome*, vol. 5, Issue No. 6, pp. 337-341, 1994.

(56) References Cited

OTHER PUBLICATIONS

Shih H., "Discovery Process for Antibody-Based Therapeutics, Chapter 2," *Development of Antibody-Based Therapeutics*, pp. 9-32, 2012.
Sigmund C., "Viewpoint: Are Studies in Genetically Altered Mice Out of Control?", *Arteriosclerosis, Thrombosis and Vascular Biology*, vol. 20, Issue No. 6, pp. 1425-1429, 2000.
Smith K., "Gene Transfer in Higher Animals: Theoretical Considerations and Key Concepts," *Journal of Biotechnology*, vol. 99, Issue No. 1, pp. 1-22, 2002.
Soukharev S., et al., "Segmental Genomic Replacement in Embryonic Stem Cells by Double Lox Targeting," *Nucleic Acids Research*, vol. 27, Issue No. 18, pp. e21-1-e21-8, 1999.
Spanopoulou E., et al., "Functional Immunoglobulin Transgenes Guide Ordered B-Cell Differentiation in Rag-1-Deficient Mice," *Genes and Development*, vol. 8, Issue No. 9, pp. 1030-1042, 1994.
Stavnezer J., et al., "Mechanism and Regulation of Class Switch Recombination," *Annual Review of Immunology*, vol. 26, pp. 261-292, 2008.
Stevens, et al., "Velocimmune: Humanization of Immunoglobulin Loci Using Velocigene Technology," (Abstract—4) Presented at 1st International MUGEN Conference on Animal Models for Human Immunological Disease, Athens, Greece, 1 page, Sep. 10-13, 2006.
Stevens, S. et al., Poster: "VelocImmune$^{TM}$: Humanization of immunoglobulin loci using VelociGene® technology," Exhibit IJR-46 to Jeffrey Rourke Declaration, 1 page, 2006.
Stevens, S. et al., Expanded Poster: "VelocImmune$^{TM}$: Humanization of immunoglobulin loci using VelociGene® technology," Exhibit IJR-48 to Jeffrey Rourke Declaration, 1 page, 2006.
Takeda S., et al., "Construction of Chimaeric Processed Immunoglobulin Genes Containing Mouse Variable and Human Constant Region Sequences," *Nature*, vol. 314, Issue No. 6010, pp. 452-454, 1985.
Tan L., et al., "A Human-Mouse Chimeric Immunoglobulin Gene with a Human Variable Region is Expressed in Mouse Myeloma Cells," *Journal of Immunology*, vol. 135, Issue No. 5, pp. 3564-3567, 1985.
Taylor L., et al., "Human Immunoglobulin Transgenes Undergo Rearrangement, Somatic Mutation and Class Switching in Mice that Lack Endogenous IgM," *International Immunology*, vol. 6, Issue No. 4, pp. 579-591, 1994.
The Jackson Laboratory, " Breeding Strategies for Maintaining Colonies of Laboratory Mice," *A Jackson Laboratory Resource Manual*, pp. 1-29, 2007.
Thykjaer T., et al., "Gene Targeting Approaches Using Positive-Negative Selection and Large Flanking Regions," *Plant Molecular Biology*, vol. 35, Issue No. 4, pp. 523-530, 1997.
Tonegawa S., "Somatic Generation of Antibody Diversity," *Nature*, vol. 302, Issue No. 5909, pp. 575-581, 1983.
Tuaillon, N. et al., "Human immunoglobulin heavy-chain minilocus recombination in transgenic mice: Gene-segment use in μ and γ transcripts," *Proceedings of the National Academy of Sciences USA*, vol. 90, pp. 3720-3724, Apr. 1993.
Tucker P., et al., "Mouse IgA Heavy Chain Gene Sequence: Implications for Evolution of Immunoglobulin Hinge Axons," *Proceedings of the National Academy of Sciences of the U.S.A.*, vol. 78, Issue No. 12, pp. 7684-7688, 1981.
Van Snick J., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, vol. 26, Issue No. 9, pp. 1085-1090, 1983.
Venken, et al., "P [acman]: A BAC transgenic platform for targeted insertion of large DNA fragments in *Drosophlia melanogaster,"* Science, vol. 314, Issue No. 5806, pp. 1747-1751, Dec. 2006.
Vollmer J., et al., "Antigen Contacts by Ni-Reactive TCR: Typical αβ Chain Cooperation Versus Alpha Chain-Dominated Specificity," *International Immunology*, vol. 12, Issue No. 12, pp. 1723-1731, 2000.

Wagner S., et al., "Antibodies Generated from Human Immunoglobulin Miniloci in Transgenic Mice," *Nucleic Acids Research*, vol. 22, Issue No. 8, pp. 1389-1393, 1994.
Wasserman, R. et al., "The Pattern of Joining ($J_H$) Gene Usage in the Human IgH Chain Is Established Predominantly at the B Precursor Cell Stage[1]," *The Journal of Immunology*, vol. 149, pp. 511-516, Jul. 1992.
Waterhouse P., et al., "Combinatorial Infection and In Vivo Recombination: a Strategy for Making Large Phage Antibody Repertoires," *Nucleic Acids Research*, vol. 21, Issue No. 9, pp. 2265-2266, 1993.
Weichhold, G. et al., "Megabase inversions in the human genome as physiological events," *Nature*, vol. 347, Issue No. 6288, pp. 90-92, Sep. 1990.
Weichhold, G. et al., "The Human Immunoglobulin Kappa Locus Consists of Two Copies That Are Organized in Opposite Polarity," *Genomics*, vol. 16 (2), pp. 503-511, 1993.
Weiner, L., "Fully Human Therapeutic Monoclonal Antibodies," *Journal of Immunology*, vol. 29, Issue No. 1, pp. 1-9, Jan./Feb. 2006.
Wilke K., et al., "Diagnosis of Haploidy and Triploidy Based on Measurement of Gene Copy Number by Real-Time PCR," *Human Mutation*, vol. 16, Issue No. 5, pp. 431-436, 2000.
Wuerffel R., et al., "S-S Synapsis During Class Switch Recombination is Promoted by Distantly Located Transcriptional Elements and Activation-Induced Deaminase," *Immunity*, vol. 27, Issue No. 5, pp. 711-722, 2007.
Xu Y., et al., "Deletion of the Ig Kappa Light Chain Intronic Enhancer/Matrix Attachment Region Impairs but does not Abolish V Kappa J Kkappa Rearrangement," *Immunity*, vol. 4, Issue No. 4, pp. 377-385, 1996.
Yamada, M. et al., "Preferential Utilization of Specific Immunoglobulin Heavy Chain Diversity and Joining Segments in Adult Human Peripheral Blood B Lymphocytes," *Journal of Experimental Medicine*, vol. 173, pp. 395-407, Feb. 1991.
Yang X., et al., "Homologous Recombination Based Modification in *Escherichia coli* and Germline Transmission in Transgenic Mice of a Bacterial Artificial Chromosome," *Nature Biotechnology*, vol. 15, Issue No. 9, pp. 859-865, 1997.
Yu, Y. et al., "Engineering Chromosomal Rearrangements in Mice," *Nature Reviews Genetics*, vol. 2, Issue No. 10, pp. 780-790, 2001.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, vol. 334, Issue No. 4, pp. 733-749, 2003.
Zhang Y., et al., "A New Logic for DNA Engineering Using Recombination in *Escherichia coli,"* Nature Genetics, vol. 20, Issue No. 2, pp. 123-128, 1998.
Zheng, J. et al., "Immunoglobulin Gene Transcripts Have Distinct $V_H DJ_H$ Recombination Characteristics in Human Epithelial Cancer Cells," *Journal of Biological Chemistry*, vol. 284, Issue No. 20, pp. 13610-13619, May 2009.
Zou, X. et al., "Removal of the BiP-retention domain in Cμ permits surface deposition and developmental progression without L-chain," *Molecular Immunology*, vol. 45, Issue No. 13, pp. 3573-3579, 2008.
NCBI Blast, Accession No. Y55HBK1W114, 2 pages, accessed Aug. 6, 2014.
Chinese Patent Office, First Office Action for Chinese Application No. 201180039668.1, 6 pages, dated Jan. 3, 2014.
Chinese Patent Office, First Office Action for Chinese Application No. 201180039668.1, 6 pages, dated Jan. 3, 2014 (English Translation).
Chinese Patent Office, Search Report, Chinese Application No. 201180039668.1, 2 pages, dated Jan. 3, 2014.
Chinese Patent Office, Search Report, Chinese Patent Application No. 201180039668.1, 1 pages, dated Jan. 3, 2014 (English Translation).
Avery, Sean, Third-Party Pre-Issuance Submission Under 37 CFR Section 1.290 in U.S. Appl. No. 14/517,755, 16 pages, dated Jun. 26, 2015.
European Patent Office, Examiners Report on Allowability for Application No. PCT/GB2010/51122, 1 page, dated Jun. 13, 2013.

(56) References Cited

OTHER PUBLICATIONS

European Patent Office, Laurent Deleu, Authorized Officer, International Search Report and Written Opinion of the International Searching Authority for Application No. PCT/GB2010/051122, 9 pages, dated Sep. 29, 2010.
European Patent Office, Laurent Deleu, Authorized Officer, International Preliminary Report on Patentability for Application No. PCT/GB2010/051122, 33 pages, dated Nov. 2, 2011.
European Patent Office, Laurent Deleu, Authorized Officer, International Search Report and Written Opinion of the International Searching Authority for Application No. PCT/GB2011/050019, 12 pages, dated May 16, 2011.
European Patent Office, Invitation to Pay Additional Fees and, Where Applicable, Protest Fee, Application No. PCT/GB2012/052296, 9 pages, dated Jan. 24, 2013.
European Patent Office, International Search Report and Written Opinion for Application No. PCT/GB2012/052296, 30 pages, dated May 17, 2013.
European Patent Office, Alessandro Brero, Authorized Officer, International Search Report and Written Opinion of the International Searching Authority for Application No. PCT/GB2012/052297, 24 pages, dated Jun. 19, 2013.
European Patent Office, Allessandro Brero, Authorized Officer, International Search Report and Written Opinion for Application No. PCT/GB2012/052298, 21 pages, dated Jun. 13, 2013.
European Patent Office, International Search Report and Written Opinion of the International Searching Authority for PCT/GB2012/052956, 14 pages, dated Mar. 1, 2013.
European Patent Office, International Search Report and Written Opinion of the International Searching Authority for Application No. PCT/GB2012/052960, 19 pages, dated Apr. 29, 2013.
European Patent Office, Gaby Brouns, Authorized Officer, International Search Report and Written Opinion for the International Searching Authority for Application No. PCT/GB2013/050682, 16 pages, dated Sep. 25, 2013.
European Patent Office, International Search Report and Written Opinion of the International Searching Authority for Application No. PCT/GB2013/050683, 11 pages, dated Jul. 9, 2013.
European Patent Office, International Search Report and Written Opinion for Application No. PCT/GB2013/051280, 19 pages, dated Nov. 15, 2013.
European Patent Office, Statement of Fact and Arguments in Support of Opposition against EP2421357, pertaining to Application No. 10734546.4, 41 pages, dated Jan. 23, 2013.
European Patent Office, Statement of Fact and Arguments in Support of Opposition pertaining to Application No. 10734546.4, 41 pages, dated Oct. 22, 2013.
European Patent Office, Opposition against EP2421357 Animal Models and Therapeutic Molecules in the name of Kymab Limited pertaining to Application No. 10734546.4, 44 pages, dated Oct. 23, 2013.
European Patent Office, Extended European Search Report for Application No. EP12171791.2, 5 pages, dated Jun. 18, 2013.
European Patent Office, Extended European Search Report for Application No. 12171793.8, 8 pages, dated Jun. 21, 2013.
European Patent Office, Laurent Deleu, Authorized Officer, Extended European Search for Application No. EP12194970, 9 pages, dated Jan. 23, 2013.
European Patent Office, Communication pursuant to Article 94(3) EPC for Application No. 12194970.5, 6 pages, dated Sep. 23, 2013.
European Patent Office, Extended European Search Report for Application No. 12194977.0, 8 pages, dated Jul. 17, 2013.
European Patent Office, Laurent Deleu, Authorized Officer, European Search Report for Application No. 12194977.0, 4 pages, dated Jul. 5, 2013.
European Patent Office, Laurent Deleu, Authorized Officer, Extended European Search Report for Application No. 12195041.4, 8 pages, dated Nov. 18, 2013.
European Patent Office, Gaby Brouns, Authorized Officer, Examination Report for Application No. EP 12795841.1, 5 pages, dated Feb. 12, 2016.
European Patent Office, Gaby Brouns, Authorized Officer, Examination Report for Application No. EP 13711119.1, 6 pages, dated Dec. 17, 2015.
European Patent Office, Laurent Deleu, Authorized Officer, Extended European Search Report for Application No. EP14170196, 8 pages, dated Oct. 8, 2014.
European Patent Office, Extended European Search Report for Application No. EP14176740.0, 7 pages, dated Oct. 15, 2014.
European Patent Office, Laurent Deleu, Authorized Officer, Communication pursuant to Article 94(3) EPC for Application No. 14176740.0, 5 pages, dated Oct. 23, 2015.
European Patent Office, Extended European Search Report for Application No. 14196645.7, 12 pages, dated Jun. 26, 2015.
European Patent Office, Extended European Search Report for Application No. 15188522.5, 15 pages, dated Feb. 2, 2016.
France Intellectual Property Office, International Search Report for Application No. 1359518, 3 pages, dated Aug. 20, 2014.
Grund, Martin, European Patent Attorney, Grund Intellectual Property Group, Third-Party Observations according to Article 115 EPC regarding 11705964.2, dated 8 pages, Oct. 9, 2013.
Grund, Martin, European Patent Attorney, Grund Intellectual Property Group, Third-Party Observations according to Article 115 EPC regarding 11705964.2, 4 pages, dated Apr. 30, 2014.
Grund, Martin, European Patent Attorney, Grund Intellectual Property Group, Third-Party Observations according to Article 115 EPC regarding 11705964.2, 5 pages, dated Feb. 26, 2015.
Grund, Martin, European Patent Attorney, Grund Intellectual Property Group, Third-Party Observations according to Article 115 EPC regarding 12171791.2, 6 pagres, dated Aug. 4, 2014.
Grund, Martin, European Patent Attorney, Grund Intellectual Property Group, Third-Party Observations according to Article 115 EPC regarding 12171791.2, 9 pages, dated Feb. 26, 2014.
Grund, Martin, European Patent Attorney, Grund Intellectual Property Group, Third-Party Observations according to Article 115 EPC regarding 12171791.2, 7 pages, dated Dec. 19, 2014.
Grund, Martin, European Patent Attorney, Grund Intellectual Property Group, Third-Party Observations according to Article 115 EPC regarding 12171793.8, 7 pages, dated Jun. 25, 2014.
Grund, Martin, European Patent Attorney, Grund Intellectual Property Group, Third-Party Observations according to Article 115 EPC regarding 12194970.5, 9 pages, dated Mar. 5, 2014.
Grund, Martin, European Patent Attorney, Grund Intellectual Property Group, Third-Party Observations according to Article 115 EPC regarding 12194970.5, 5 pages, dated Aug. 12, 2014.
Grund, Martin, European Patent Attorney, Grund Intellectual Property Group, Third-Party Observations according to Article 115 EPC regarding 12194970.5, 6 pages, dated Nov. 15, 2013.
Grund, Martin, European Patent Attorney, Grund Intellectual Property Group, Third-Party Observations according to Article 115 EPC regarding 12194970.5, 6 pages, dated Apr. 25, 2014.
Grund, Martin, European Patent Attorney, Grund Intellectual Property Group, Third-Party Observations according to Article 115 EPC regarding EP12194977.0, 4 pages, dated Mar. 26, 2014.
Grund, Martin, European Patent Attorney, Grund Intellectual Property Group, Third-Party Observations according to Article115 EPC regarding 12194977.0, 5 pages, dated May 12, 2015.
Grund, Martin, European Patent Attorney, Grund Intellectual Property Group, Third-Party Observations according to Article 115 EPC regarding EP12195041.4, 5 pages, dated Jul. 30, 2014.
Grund, Martin, European Patent Attorney, Grund Intellectual Property Group, Third-Party Observations according to Article 115 EPC regarding 12762377.5, 7 pages, dated May 22, 2015.
Grund, Martin, European Patent Attorney, Grund Intellectual Property Group, Third-Party Observations according to Article 115 EPC regarding 12762377.5, 8 pages, dated Feb. 12, 2016.
Grund, Martin, European Patent Attorney, Grund Intellectual Property Group, Third-Party Observations according to Article 115 EPC regarding 12772122.3, 5 pages, dated Mar. 12, 2015.

(56) References Cited

OTHER PUBLICATIONS

Grund, Martin, European Patent Attorney, Grund Intellectual Property Group, Third-Party Observations according to Article 115 EPC regarding 12795606.8, 6 pages, dated Feb. 26, 2014.
Grund, Martin, European Patent Attorney, Grund Intellectual Property Group, Third-Party Observations according to Article 115 EPC regarding 12795606.8, 4 pages, dated Mar. 26, 2015.
Grund, Martin, European Patent Attorney, Grund Intellectual Property Group, Third-Party Observations according to Article 115 EPC regarding 13711119.1, 7 pages, dated Dec. 9, 2015.
Grund, Martin, European Patent Attorney Grund Intellectual Property Group, Third-Party Observations according to Article 115 EPC regarding 14176740.0, 13 pages, dated Aug. 10, 2015.
Grund, Martin, European Patent Attorney Grund Intellectual Property Group, Third-Party Observation for Application No. PCT/GB2012/052297, 3 pages, dated Jan. 17, 2014.
Grund, Martin, European Patent Attorney Grund Intellectual Property Group, Third-Party Observation for Application No. PCT/GB2012/052298, 4 pages, dated Jan. 17, 2014.
Grund, Martin, European Patent Attorney Grund Intellectual Property Group, Third Party Observation for Application No. PCT/GB2012/052960, 3 pages, dated Apr. 2, 2014.
Grund, Martin, European Patent Attorney Grund Intellectual Property Group, Third-Party Observation for Application No. PCT/GB2012/052380, 4 pages, dated Jan. 24, 2014.
Grund, Martin, European Patent Attorney Grund Intellectual Property Group, Third-Party Observation for Application No. PCT/GB2013/050682, 3 pages, dated Jul. 28, 2014.
Grund, Martin, European Patent Attorney Grund Intellectual Property Group, Third-Party Observation for Application No. PCT/GB2013/050683, 2 pages, dated Jul. 28, 2014.
Grund, Martin, European Patent Attorney Grund Intellectual Property Group, Third-Party Observation for Application No. PCT/US2012/026416, 2 pages, dated Jun. 6, 2013.
Jarrell, Brenda Herschbachi, Third-Party Pre-Issuance Submission Under 37 CFR Section 1.290 in U.S. Appl. No. 14/052,259, 7 pages, dated Aug. 6, 2014.
Lyon, Charles E., Attorney for Applicant, Third Party Pre-Issuance Submission Under 37 CFR 1.290 in U.S. Appl. No. 13/846,672, 32 pages, dated Mar. 17, 2015.
Lyon, Charles E., Attorney for Applicant, Third Party Pre-Issuance Submission Under 37 CFR 1.290 in U.S. Appl. No. 13/875,892, 49 pages, dated May 5, 2015.
Lyon, Charles E., Attorney for Applicant, Third Party Pre-Issuance Submission Under 37 CFR 1.290 in U.S. Appl. No. 13/886,511, 18 pages, dated May 5, 2015.
Lyon Charles, E. Attorney for Applicant, Third Party Pre-Issuance Submission Under 37 CFR 1.290 in U.S. Appl. No. 14/040,405, 18 pages, dated Jan. 16, 2015.
Lyon, Charles E., Attorney for Applicant, Third Party Pre-Issuance Submission Under 37 CFR 1.290 in U.S. Appl. No. 14/040,427, 20 pages, dated Jan. 16, 2015.
Lyon, Charles E., Attorney for Applicant, Third Party Pre-Issuance Submission Under 37 CFR 1.290 in U.S. Appl. No. 14/056,434, 6 pages, dated Dec. 15, 2014.
Lyon, Charles E., Attorney for Applicant, Third-Party Pre-Issuance Submission Under 37 CFR 1.290 in U.S. Appl. No. 14/056,700, 6 pages, dated Nov. 28, 2014.
Lyon, Charles E., Attorney for Applicant, Third-Party Pre-Issuance Submission Under 37 CFR 1.290 in U.S. Appl. No. 14/056,707, 10 pages, dated Nov. 28, 2014.
Lyon, Charles E., Attorney for Applicant, Third Party Pre-Issuance Submission Under 37 CFR 1.290 in U.S. Appl. No. 14/137,902, 9 pages, dated Nov. 13, 2014, 9 pages.
Lyon, Charles E., Attorney for Applicant, Third Party Pre-Issuance Submission Under 37 CFR 1.290 in U.S. Appl. No. 14/080,630, 8 pages, dated Oct. 31, 2014.
Lyon, Charles E., Attorney for Applicant, Third Party Pre-Issuance Submission Under 37 CFR 1.290 in U.S. Appl. No. 14/220,080, 28 pages, dated Jul. 28, 2015.
Lyon, Charles E., Attorney for Applicant, Third Party Pre-Issuance Submission Under 37 CFR 1.290 in U.S. Appl. No. 14/220,095, 19 pages, dated Aug. 4, 2015.
Lyon, Charles E., Attorney for Applicant, Third Party Pre-Issuance Submission Under 37 CFR 1.290 in U.S. Appl. No. 14/220,099, 43 pages, dated Apr. 29, 2015.
Lyon, Charles E., Attorney for Applicant, Third Party Pre-Issuance Submission Under 37 CFR 1.290 in U.S. Appl. No. 14/226,698, 53 pages, dated Jun. 3, 2015.
Lyon, Charles E., Attorney for Applicant, Third Party Pre-Issuance Submission Under 37 CFR 1.290 in U.S. Appl. No. 14/226,706, 53 pages, dated Jul. 28, 2015.
Lyon, Charles E., Attorney for Applicant, Third Party Pre-Issuance Submission Under 37 CFR 1.290 in U.S. Appl. No. 14/263,158, 16 pages, dated Apr. 29, 2015.
Lyon, Charles E., Attorney for Applicant, Third Party Pre-Issuance Submission Under 37 CFR 1.290 in U.S. Appl. No. 14/263,176, 16 pages, dated Apr. 29, 2015.
Lyon, Charles E., Attorney for Applicant, Third Party Pre-Issuance Submission Under 37 CFR 1.290 in U.S. Appl. No. 14/497,054, 81 pages, dated Oct. 21, 2015.
Lyon, Charles E., Attorney for Applicant, Third Party Pre-Issuance Submission Under 37 CFR 1.290 in U.S. Appl. No. 14/516,461, 27 pages, dated Aug. 4, 2015.
New Zealand Patent Office, Simon Maguire, Authorized Officer, Further Examination Report for Patent No. 623756, 3 pages, dated Sep. 9, 2015.
Pobursky, Kevin J, Attorney for Applicant, Third-Party Pre-Issuance Submission Under 37 CFR 1.290 in U.S. Appl. No. 13/433,084, 15 pages, dated Apr. 1, 2014.
Pobursky, Kevin J, Attorney for Applicant, Third-Party Pre-Issuance Submission Under 37 CFR 1.290 in U.S. Appl. No. 13/434,361, 15 pages, dated Apr. 1, 2014.
Pobursky, Kevin J, Attorney for Applicant, Third-Party Pre-Issuance Submission Under 37 CFR 1.290 in U.S. Appl. No. 13/740,727, 25 pages, dated May 27, 2014.
Pobursky, Kevin J, Attorney for Applicant, Third-Party Pre-Issuance Submission Under 37 37 CFR 1.290 in U.S. Appl. No. 13/843,528, 14 pages, dated Mar. 18, 2014.
Steven, Robert, Olswang, LLP, Kymab Limited Statement of Facts and Evidence in Opposition to EP2550363, 22 pages, dated Sep. 10, 2015.
United Kingdom Intellectual Property Office, Dr. Rowena Dinham, International Search Report for Application No. GB1116122.1, 1 page, dated Feb. 2, 2012.
United Kingdom Intellectual Property Office, Corrected International Search Report and Opinion for Application No. GB1122047.2, 5 pages, dated Apr. 20, 2012.
United Kingdom Intellectual Property Office, Combined Search and Examination Report under Sections 17 and 18(3) for Application No. GB1317410.7, 8 pages, dated Nov. 21, 2013.
United Kingdom Intellectual Property Office, Combined Search and Examination Report under Sections 17 and 18(3) for Application No. GB1317447.9, 7 pages, dated Jan. 14, 2014.
Urquhart-Dykes & Lord LLP, Third-Party Observation for Application No. EP20140772198, 8 pages, dated Dec. 14, 2015.
USPTO, Excerpts from U.S. Appl. No. 14/682,859, filed Apr. 9, 2015, including Applicant-initiated Interview Summary; Amendments to the Claims and Information Disclosure Statement, 14 pages.
Williams, Kathleen M., Attorney for Applicant, Third-Party Pre-Issuance Submission Under 37 CFR 1.290 in U.S. Appl. No. 14/600,829, 18 pages, dated Apr. 1, 2016.
Williams, Kathleen M., Attorney for Applicant, Third-Party Pre-Issuance Submission Under 37 CFR 1.290 in U.S. Appl. No. 14/679,949, 18 pages, dated Apr. 1, 2016.
Andrew Murphy, "VelocImmune: Immunoglobulin Variable Region Humanized Mice", Recombinant Antibodies for Immunotherapy. $1^{st}$ ed. Cambridge: Cambridge University Press, pp. 100-108, 2009.
Briney, et al., "Human Peripheral Blood Antibodies with Long HCDR3s are Established Primarily at Original Recombination Using a Limited Subset of Germline Genes," Public Library of Science ONE, vol. 7, No. 5, 13 pages, May 2012.

(56) References Cited

OTHER PUBLICATIONS

Brüggemann, et al., "Human Antibody Production in Transgenic Mice: Expression from 100 kb of the Human IgH Locus," European Journal of Immunology, vol. 21, No. 5, pp. 1323-1326, May 1991.
Feeney, "Genetic and Epigenetic Control of V Gene Rearrangement Frequency," V(D)J Recombination, Advances in Experimental Medicine and Biology, vol. 650, pp. 73-81, 2009.
Green, "Antibody Engineering via Genetic Engineering of the Mouse: Xenomouse Strains are a Vehicle for the Facile Generation of Therapeutic Human Monoclonal Antibodies," Journal of Immunological Methods, vol. 231, Nos. 1-2, pp. 11-23, Dec. 1999.
Huang, et al., "Structural Basis of Tyrosine Sulfation and VH-Gene Usage in Antibodies that Recognize the HIV Type 1 Coreceptor-Binding Site on gp120," Proceedings of the National Academy of Science USA, vol. 101, No. 9, pp. 2706-2711, Mar. 2004.
Jakobovits, et al, "From Xenomouse Technology to Panitumumab, the First Fully Human Antibody Product From Transgenic Mice," Nature Biotechnology, vol. 25, No. 10, pp. 1134-1143, Oct. 2007.
Jung, et al., "Mechanism and Control of V(D)J Recombination at the Immunoglobulin Heavy Chain Locus," Annual Review of Immunology, vol. 24, pp. 541-570, Apr. 2006.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, vol. 85, No. 17, pp. 8467-8476, Sep. 2011.
Mendez, et al.,"Functional Transplant of Megabase Human Immunoglobulin Loci Recapitulates Human Antibody Response in Mice," Nature Genetics, vol. 15, pp. 146-156, Feb. 1997.
Nadel, et al., "Sequence of the Spacer in the Recombination Signal Sequence Affects V(D)J Rearrangement Frequency and Correlates with Nonrandom Vκ Usage In Vivo," Journal of Experimental Medicine, vol. 187, No. 9, pp. 1495-1503, May 1998.
Nicholson, et al., "Antibody Repertoires of Four-and Five-Feature Translocus Mice Carrying Human Immunoglobulin Heavy Chain and Kappa and Lamba Light Chain Yeast Artificial Chromosomes," The Journal of Immunology, vol. 163, No. 12, pp. 6898-6906, Dec. 1999.
Schroder, et al., "Preferential Utilization of Conserved Immunoglobulin Heavy Chain Variable Gene Segments During Human Fetal Life," Proceedings of the National Academy of Sciences (USA), vol. 87, pp. 6146-6150, Aug. 1990.
Yu, et al., Differential Usage of VH Gene Segments Is Mediated by cis Elements, The Journal of Immunology, vol. 161, No. 7, pp. 3444-3454, Oct. 1998.
Adams, D., et al., "A Genome-Wide, End-Sequenced 129Sv BAC Library Resource for Targeting Vector Construction," Genomics, vol. 86, No. 6, pp. 753-758, Dec. 2005.
Askew, R., et al., "Site-Directed Point Mutations in Embryonic Stem Cells: a Gene-Targeting Tag-and-Exchange Strategy," Molecular and Cellular Biology, vol. 13, No. 7, pp. 4115-4124, Jul. 1993.
Auerbach, et al., "Establishment and Chimera Analysis of 129/ SvEv- and C57BL/6-Derived Mouse Embryonic Stem Cell Lines," Biotechniques, vol. 29: No. 5, pp. 1024-1032, Nov. 2000.
Baker et al., "Homologous Recombination between Transferred and Chromosomal Immunoglobulin Kappa Genes," Molecular and Cellular Biology, vol. 8, No. 10, pp. 4041-4047, Oct. 1988.
Barreto et al., "AID From Bony Fish Catalyzes Class Switch Recombination," Journal of Experimental Medicine, vol. 202, No. 6, pp. 1-6, Sep. 2005.
Bates et al., "Chromosomal Position of a VH Gene Segment Determines Its Activation and Inactivation as a Substrate for V(D)J Recombination," The Journal of Experimental Medicine, vol. 204, No. 13, pp. 3247-3256, Dec. 2007.
Beard, et al., "Efficient Method to Generate Single-Copy Transgenic Mice by Site-Specific Integration in Embryonic Stem Cells," Genesis, vol. 44, No. 1, pp. 23-28, Jan. 2006.
Beck et al., "Nucleotide Sequence and Exact Localization of the Neomycin Phosphotransferase Gene from Transposon Tn5," Gene, vol. 19, No. 3, pp. 327-336, Oct. 1982.
Berg et al., "Inverted repeats of Tn5 are Transposable Elements," Proceedings of the National Academy of Sciences (USA), Genetics, vol. 79, No. 8, pp. 2632-2635, Apr. 1982.
Bethke et al., "Segmental Genomic Replacement by Cre-Mediated Recombination: Genotoxic Stress Activation of the P53 Promoter in Single-Copy Transformants," Nucleic Acids Research, vol. 25, No. 14, pp. 2828-2834, Jul. 1997.
Billiard, et al., "Ongoing Dll4-Notch Signaling is Required for T-Cell Homeostasis in the Adult Thymus," European Journal of Immunology, Aug. 4, 2011, vol. 41, No. 8, pp. 2207-2216, Aug. 2011.
Bolland et al., "Antisense Intergenic Transcription Precedes Igh D-to-J Recombination and is Controlled by the Intronic Enhancer Eμ," Molecular and Cellular Biology, vol. 27, No. 15, pp. 5523-5533, Aug. 2007.
Bonin et al., "Isolation, Microinjection, and Transfer of Mouse Blastocysts" Methods in Molecular Biology, vol. 158, Gene Knockout Protocols, pp. 121-134.
Bottaro et al., "Deletion of the IgH Intronic Enhancer and Associated Matrix-Attachment Regions Decreases, But Does Not Abolish, Class Switching at the μ Locus," International Immunology, vol. 10, No. 6, pp. 799-806, Jun. 1998.
Bradley et al., "Formation of Germ-Line Chimaeras From Embryo-Derived Teratocarcinoma Cell Lines," Nature, vol. 309, No. 5965, pp. 255-256, May 1984.
Breden et al., "Comparison of Antibody Repertoires Produced by HIV-1 Infection, Other Chronic and Acute Infections, and Systemic Autoimmune Disease," PLoS One., vol. 6, No. 3, pp. 1-11, Mar. 2011.
Brocker et al., "Evolutionary Divergence and Functions of the ADAM and ADAMTS Gene Families" Human Genomics, vol. 4, No. 2, pp. 43-55, Oct. 2009.
Brüggemann, "Human Antibody Expression in Transgenic Mice," Archivum Immunologiae et Therapiae Experimentalis, vol. 49, No. 3, pp. 203-208, 2001.
Brüggemann et al., "Immunoglobulin Heavy Chain Locus of the Rat: Striking Homology to Mouse Antibody Genes," Proceedings of the National Academy of Sciences (USA), Immunology, vol. 83, No. 16, pp. 6075-6079, Aug. 1986.
Brüggemann et al., "A Repertoire of Monoclonal Antibodies with Human Heavy Chains from Transgenic Mice," Proceedings of the National Academy of Sciences (USA), Immunology, vol. 86, No. 17, pp. 6709-6713, Sep. 1989.
Buehr et al., "Capture of Authentic Embryonic Stem Cells from Rat Blastocysts," Cell, vol. 135, No. 7, pp. 1287-1298, Dec. 2008.
Cadinanos et al., "Generation of an Inducible and Optimized PiggyBac Transposon System," Nucleic Acids Research, vol. 35, No. 12, Jun. 2007.
Carstea, et al., "Germline Competence of Mouse ES and iPS Cell Lines: Chimera Technologies and Genetic Background," World Journal of Stem Cells, vol. 1, No. 1, pp. 22-29, Dec. 2009.
Chen et al., "B Cell Development in Mice that Lack One or Both Immunoglobulin Kappa Light Chain Genes," The EMBO Journal, vol. 12, No. 3, pp. 821-830, Mar. 1993.
Chen et al., "Immunoglobulin Heavy Chain Gene Replacement: A Mechanism of Receptor Editing" Immunity, vol. 3, No. 6, pp. 747-755, Dec. 1995.
Cho, "Testicular and Epididymal Adams: Expression and Function During Fertilization," Nature Reviews Urology, vol. 9, No. 10, pp. 550-560, Oct. 2012.
Choi et al., "Characterization and Comparative Genomic Analysis of Intronless Adams with Testicular Gene Expression," Genomics, vol. 83, No. 4, pp. 636-646, Aug. 2003.
Clark et al., "Trends in Antibody Sequence Changes During the Somatic Hypermutation Process," The Journal of Immunology, vol. 177, No. 1, pp. 333-340, Jul. 2006.
Clark et al., "A Future for Transgenic Livestock," Nature Reviews Genetics, vol. 4, No. 10, pp. 825-833, Oct. 2003.
Colbere Garapin et al., "A New Dominant Hybrid Selective Marker for Higher Eukaryotic Cells" Journal of Molecular Biology, vol. 150, No. 1, pp. 1-14, Jul. 1981.
Collins, et al., "A Mouse for All Reasons," Cell, vol. 128, No. 1, pp. 9-13, Jan. 2007.

(56) References Cited

OTHER PUBLICATIONS

Combriato, et al., "Regulation of Human Igλ Light Chain Gene Expression by NF-κB1," Journal of Immunology, vol. 168, No. 3, pp. 1259-1266, Feb. 2002.
Conrath, et al., "Camel Single-Domain Antibodies as Modular Building Units in Bispecific and Bivalent Antibody Constructs," The Journal of Biological Chemistry, vol. 276, No. 10, pp. 7346-7350, Mar. 2001.
Copeland et al., "Recombineering: A Powerful New Tool for Mouse Functional Genomic," Nature Reviews Genetics, vol. 2, No. 10, pp. 769-869, Oct. 2001.
Corti et al., "A Neutralizing Antibody Selected from Plasma Cells That Binds to Group 1 and Group 2 Influenza A Hemagglutinins" Science, vol. 333, No. 6044, pp. 850-856, Aug. 2011.
Cuesta et al., "Multivalent Antibodies: When Design Surpasses Evolution," Trends Biotechnology, vol. 28, No. 7, pp. 355-362, Jul. 2010.
De Saint Vincent et al., "Homologous Recombination in Mammalian Cells Mediates Formation of a Functional Gene From Two Overlapping Gene Fragments," Proceedings of the National Academy of Sciences, (USA) vol. 80, No. 7, pp. 2002-2006, Apr. 1983.
DeChiara et al., "VelociMouse: Fully ES Cell-Derived F0-Generation Mice Obtained from the Injection of ES Cells into Eight-Cell-Stage Embryos," Gene Knockout Protocols: Second Edition, vol. 530, pp. 311-324, 2009.
DeChiara et al., "Producing Fully ES Cell-Derived Mice From Eight-Cell Stage Embryo Injections," Methods in Enzymology, vol. 476, Chapter 16, pp. 285-294, Jan. 2010.
Denome et al., "Patterns of Polyadenylation Site Selection in Gene Constructs Containing Multiple Polyadenylation Signals," Molecular and Cellular Biology, vol. 8, No. 11, pp. 4829-4839, Nov. 1988.
Diez-Roux et al., "A High-Resolution Anatomical Atlas of the Transcriptome in the Mouse Embryo," PLoS Biology, vol. 9, No. 1, pp. 1-13, Jan. 2011.
Ding, et al., "Generation of High-Affinity Fully Human Anti-Interleukin-8 Antibodies from its cDNA by Two-Hybrid Screening and Affinity Maturation in Yeast," Protein Science, vol. 19, No. 10, pp. 1957-1966, Oct. 2010.
DiNoia et al., "Molecular Mechanisms of Antibody Somatic Hypermutation," Annual Review of Biochemistry, vol. 76, No. 1, pp. 1-22, 2007.
Doetschman et al., "Establishment of Hamster Blastocyst-Derived Embryonic Stem (ES) Cells," Developmental Biology, vol. 127, No. 1, pp. 224-227, May 1988.
Doetschman, et al., "Targeted Mutation of the Hprt Gene in Mouse Embryonic Stem Cells," Proceedings of the National Academy of Sciences (USA), vol. 85, No. 22, pp. 8583-8587, Nov. 1988.
Doyle, et al., "The Construction of Transgenic and Gene Knockout/Knockin Mouse Models of Human Disease," Transgenic Research, vol. 21, No. 2, pp. 327-349, Apr. 2012.
1000 Genomes Project Consortium, "A Map of Human Genome Variation From Population-Scale Sequencing," Nature, vol. 467, No. 7319, pp. 1061-1074, Oct. 2012.
Durdik et al., "Isotype Switching by a Microinjected μ Immunoglobulin Heavy Chain Gene in Transgenic Mice," Proceedings of the National Academy of Sciences (USA), Immunology, vol. 86, No. 7, pp. 2346-2350, Apr. 1989.
Edwards, et al, "The ADAM Metalloproteinases," Molecular Aspects of Medicine, vol. 29, No. 5, pp. 258-289, Oct. 2008.
Eisener-Dorman, et al., "Cautionary insights on knockout mouse studies: The gene or not the gene?" Brain, Behavior, and Immunity, vol. 23, No. 3, pp. 318-324, Sep. 2009.
Ekiert et al., "A Highly Conserved Neutralizing Epitope on Group 2 Influenza A Viruses," Science, vol. 333, No. 6044, pp. 843-850, Aug. 2011 2011.
Evans, "Fertilin B and Other Adams as Integrin Ligands: Insights Into Cell Adhesion and Fertilization," BioEssays vol. 23, No. 7, pp. 628-639, Jul. 2001.
Featherstone et al., "The Mouse Immunoglobulin Heavy Chain V-D Intergenic Sequence Contains Insulators That May Regulate Ordered V(D)J Recombination," The Journal of Biological Chemistry, vol. 285, No. 13, pp. 9327-9338, Mar. 2010.
Fell et al., "Homologous Recombination in Hybridoma Cells: Heavy Chain Chimeric Antibody Produced by Gene Targeting," Proceedings of the National Academy of Sciences (USA), vol. 86, No. 21, pp. 8507-8511, Nov. 1989.
Feschotte et al., "DNA Transposons and the Evolution of Eukaryotic Genomes.," Annual Review of Genetics, vol. 41, pp. 331-368, 2007.
Folger et al., "Patterns of Integration of DNA Microinjected into Cultured Mammalian Cells: Evidence for Homologous Recombination Between Injected Plasmid DNA Molecules," Molecular and Cellular Biology, vol. 2, No. 11, pp. 1372-1387, Nov. 1982.
Forconi et al., "The Normal IGHV1-69-Derived B-Cell Repertoire Contains Stereotypic Patterns Characteristic of Unmutated CLL," vol. 115, No. 1, pp. 71-77, Jan. 2010.
Fukita et al., "Somatic Hypermutation in the Heavy Chain Locus Correlates with Transcription," Immunity, vol. 9, No. 1, pp. 106-114, Jul. 1998.
Gefter et al., "Expression of a VHC kappa chimaeric protein in mouse myeloma cells," Nature, vol. 309, No. 5966, pp. 364-367, May 1984 (Abstract only).
Gerdes et al., "Physical Map of the Mouse λ Light Chain and Related Loci," Immunogenetics, vol. 54, No. 1, pp. 62-65, Apr. 2002.
Gerstein, et al., "Isotype Switching of an Immunoglobulin Heavy Chain Transgene Occurs by DNA Recombination Between Different Chromosomes," Cell, vol. 63, No. 3, pp. 537-548, Nov. 1990.
Geurts et al., "Knockout Rats via Embryo Microinjection of Zinc-Finger Nucleases," Science, vol. 325, No. 5939, p. 433, Jul. 2009.
Giallourakis, et al. "Elements Between the Igh Variable (V) and Diversity (D) Clusters Influence Antisense Transcription and Lineage-Specific V(D)J Recombination," Proceedings of the National Academy of Sciences (USA), vol. 107, No. 51, pp. 22207-22212, Dec. 2010.
Gluzman, "SV40-Transformed Simian Cells Support the Replication of Early SV40 Mutants," Cell, vol. 23, No. 1, pp. 175-182, Jan. 1981.
Goodhart, et al., "Rearrangement and Expression of Rabbit Immunoglobulin Kappa Light Chain Gene in Transgenic Mice," Proceedings of the National Academy of Sciences (USA), vol. 84, No. 12, pp. 4229-4233, Jun. 1987.
Gorman et al., "The IgK enhancer influences the ratio of IgK Versus Igλ B lymphocytes" Immunity, vol. 5, No. 3, pp. 241-252, Sep. 1996.
Gorny et al., "Human Anti-V3 HIV-1 Monoclonal Antibodies Encoded by the VH5-51/VL Lambda Genes Define a Conserved Antigenic Structure," PLoS One, vol. 6, No. 12, pp. 1-10, Dec. 2011.
Goyenechea et al., "Cells Strongly Expressing Ig(Kappa) Transgenes Show Clonal Recruitment of Hypermutation: a Role for Both MAR and the Enhancers," The EMBO Journal, vol. 16, No. 13, pp. 3987-3994, Jul. 1997.
Gu et al., "Independent Control of Immunoglobulin Switch Recombination at Individual Switch Regions Evidenced Through Cre-Loxp-Mediated Gene Targeting," Cell, vol. 73, No. 6, pp. 1155-1164, Jun. 1993
Guerrero et al., "The Bleomycin Resistance Gene of Transposon Tn5 is an Excellent Marker for Transformation of Corynebacteria," Applied Microbiology Biotechnology, vol. 36, No. 6, pp. 759-762, Mar. 1992.
Guntaka, "Transcription Termination and Polyadenylation in Retroviruses" Microbiological Reviews, vol. 57, No. 3, pp. 511-521, Sep. 1993.
Han et al., "Comprehensive Analysis of Reproductive Adams: Relationship of ADAM4 and ADAM6 with an ADAM Complex Required for Fertilization in Mice," Biology of Reproduction, vol. 80, No. 5, pp. 1001-1008, Jan. 2009.
Hasty et al., "Target Frequency and Integration Pattern for Insertion and Replacement Vectors in Embryonic Stem Cells," Molecular and Cellular Biology, vol. 11, No. 9, pp. 4509-4517, Sep. 1991.

(56) References Cited

OTHER PUBLICATIONS

Hagiwara, "Transgenic Expression of Vpreb-3 Under the Control of the Immunoglobulin Heavy Chain Enhancer and SV40 Promoter," Kobe Journal of Medical Sciences, vol. 42, No. 1, pp. 43-59, Feb. 1996 (English Abstract).
Hendricks, et al., "Organization of the Variable Region of the Immunoglobulin Heavy-Chain Gene Locus of the Rat," Immunogenetics, vol. 62, No. 7, pp. 479-486, Jul. 2010.
Houvila et al., "Shedding Light on ADAM Metalloproteinases," Trends in Biochemical Sciences, vol. 30, No. 7, pp. 413-422, Jul. 2005.
Hudziak et al., "Establishment of Mammalian Cell Lines Containing Multiple Nonsense Mutations and Functional Suppressor tRNA Genes," Cell, vol. 31, No. 1, pp. 137-146, Nov. 1982.
Iglesias-Ussel, et al, "Forced Expression of AID Facilitates the Isolation of Class Switch Variants From Hybridoma Cells," Journal of Immunological Methods, vol. 316, No. 1-2, pp. 59-66, Oct. 2006.
Ivics et al., "The Expanding Universe of Transposon Technologies for Gene and Cell Engineering," Mobile DNA, vol. 1, No. 1, pp. 1-25, Dec. 2010.
Ivics et al., "The Sleeping Beauty Transposable Element: Evolution, Regulation and Genetic Applications," Current Issues in Molecular Biology, vol. 6, No. 1, pp. 43-55, Jan. 2004.
Izsvak et al., "Sleeping Beauty Transposition: Biology and Applications for Molecular Therapy," Molecular Therapy, vol. 9, No. 2, pp. 147-156, Feb. 2004.
Jacob et al., "Gene Targeting in the Rat: Advances and Opportunities," Trends in Genetics, vol. 26, No. 12, pp. 510-518, Dec. 2010.
Janssens, et al., "Generation of Heavy-Chain-Only Antibodies in Mice," Proceedings of the National Academy of Sciences (USA), vol. 103, No. 41, pp. 15130-15135, Oct. 2006.
Jendreyko, et al., "Intradiabodies, Bispecific, Tetravalent Antibodies for the Simultaneous Functional Knockout of Two Cell Surface Receptors," The Journal of Biological Chemistry, vol. 278, No. 48, pp. 47812-47819, Nov. 2003.
Kaminski, et al., "Antibody Class Switching Differs Among SJL, C57BL/6 and 129 Mice," International Immunology, vol. 19, No. 4, pp. 545-556, Apr. 2007.
Kellerman, et al, "Developing the Xenomouse Technology for Evaluating Immunogenicity," AntibOZ 2 Conference, Australia, 2004.
Kim et al., "CHO Cells in Biotechnology for Production of Recombinant Proteins: Current State and Further Potential" Applied Microbiology Biotechnology, vol. 93, No. 3, pp. 917-930, Feb. 2012.
Kim, et al., "Expression and Relationship of Male Reproductive Adams in Mouse," Biology of Reproduction, vol. 74, No. 4, pp. 744-750, Apr. 2006.
Kingzette et al., "Trans-Chromosomal Recombination Within the Ig Heavy Chain Switch Region in B Lymphocytes," Proceedings of the National Academy of Sciences, vol. 95, pp. 11840-11845, Sep. 1998.
Kitamura et al., "A B Cell-Deficient Mouse by Targeted Disruption of the Membrane Exon of the Immunoglobulin Chain Gene," Nature, vol. 350, No. 6317, pp. 423-426, Apr. 1991.
Kling, "News in Brief," Nature Biotechnology, vol. 25, No. 6, p. 613, Jun. 2007.
Kohrer et al., "Import of Amber and Ochre Suppressor tRNAs into Mammalian Cells: A General Approach to Site-Specific Insertion of Amino Acid Analogues Into Proteins," Proceedings of the National Academy of Sciences (USA), vol. 98, No. 25, pp. 214310-14315, Dec. 2001.
Kostenuik, et al., "Denosumab, a Fully Human Monoclonal Antibody to RANKL, Inhibits Bone Resorption and Increases BMD in Knock-In Mice that Express Chimeric (Murine/Human) RANKL," Journal of Bone and Mineral Research, vol. 4, No. 2, pp. 182-195, Feb. 2009.
Kotzamaris et al., "Recombining Overlapping Bacs Into a Single Larger BAC," BMC Biotechnology, vol. 4, No. 1, pp. 1-10, Jan. 2004.

Krause, "Epitope-Specific Human Influenza Antibody Repertoires Diversify by B Cell Intraclonal Sequence Divergence and Interclonal Convergence," The Journal of Immunology, vol. 187, No. 7, pp. 3704-3711, Aug. 2011.
Kruif et al., "Human Immunoglobulin Repertoires Against Tetanus Toxoid Contain a Large and Diverse Fraction of High-Affinity Promiscuous Vh Genes," Journal of Molecular Biology, vol. 387, pp. 548-558, Feb. 2009.
Krutskikh et al., "Epididymal Protein Rnase10 Is Required for Post-Testicular Sperm Maturation and Male Fertility," The FASEB Journal, vol. 26, No. 10, pp. 4198-4209, Oct. 2012.
Kucherlapati et al., "Homologous Recombination Between Plasmids in Mammalian Cells Can be Enhanced by Treatment of Input DNA," Proceedings of the National Academy of Sciences (USA), Genetics, vol. 81, pp. 3135-3157, May 1984.
Kuroiwa et al., "Sequential Targeting of the Genes Encoding Immunoglobulin and Prion Protein in Cattle," Nature Genetics, vol. 36, No. 7, pp. 775-780, Jul. 2004.
Laventie, et al., "Heavy Chain-Only Antibodies and Tetravalent Bispecific Antibody Neutralizing *Staphylococcus aureus* Leukotoxins," Proceedings of the National Academy of Sciences (USA), vol. 108, No. 39, pp. 16404-16409, Sep. 2011.
Lee et al, "Human C5ar Knock-In Mice Facilitate the Production and Assessment of Anti-Inflammatory Monoclonal Antibodies," Nature Biotechnology, vol. 24, No. 10, pp. 1279-1284, Oct. 2006.
Li et al., "Transgenic Mice With a Diverse Human T Cell Antigen Receptor Repertoire," Nature Medicine, vol. 16, No. 9, pp. 1029-1035, Sep. 2010.
Li et al., "The Minimum Internal and External Sequence Requirements for Transposition of the Eukaryotic Transformation Vector PiggyBac," Molecular Genetics and Genomics, vol. 266, No. 2, pp. 190-198, Oct. 2001.
Li et al., "Crafting Rat Genomes With Zinc Fingers," Nature Biotechnology, vol. 29, No. 1, pp. 39-41, Jan. 2011.
Li et al., "Germline Competent Embryonic Stem Cells Derived from Rat Blastocysts," Cell, vol. 135, No. 7, pp. 1299-1310, Dec. 2008.
Liao et al., "Generation of Induced Pluripotent Stem Cell Lines from Adult Rat Cells," Cell Stem Cell Brief Report, vol. 4, pp. 11-15, Jan. 2009.
Luciw et al., "Location and Function of Retroviral and SV40 Sequences that Enhance Biochemical Transformation after Microinjection of DNA," Cell, vol. 33, No. 3, pp. 705-176, Jul. 1983.
Luo et al., "Chromosomal Transposition of a Tc1/Mariner-Like Element in Mouse Embryonic Stem Cells," Proceedings of the National Academy of Sciences (USA), Genetics, vol. 95, No. 18, pp. 10769-10773, Sep. 1998.
Lonberg, "Human Antibodies from Transgenic Animals," Nature Biotechnology, vol. 23, No. 9, pp. 1117-1125, Sep. 2005.
Loveslati, et al., "A Study of Gm Allotypes and Immunoglobulin Heavy Gamma IGHG Genes in Berbers, Arabs and Sub-Saharan Africans From Jerba Island, Tunisia" Blackwell Science Ltd., European Journal of Immunogenetics, vol. 28, No. 5, pp. 531-538, Oct. 2001.
Luby, et al., "The Mu Switch Region Tandem Repeats Are Important, But Not Required, for Antibody Class Switch Recombination," The Journal of Experimental Medicine, vol. 193, No. 2, pp. 159-168, Jan. 2001.
Macdonald, et al., "Precise and In Situ Genetic Humanization of 6 Mb of Mouse Immunoglobulin Genes," Proceedings of the National Academy of Sciences (USA), vol. 111, No. 14, 5147-5152, Apr. 2014.
Mack et al., "A Small Bispecific Antibody Construct Expressed as a Functional Single-Chain Molecule with High Tumor Cell Cytotoxicity," Proceedings of the National Academy of Sciences (USA), Immunology, vol. 92, pp. 7021-7025, Jul. 1995.
Makris et al., "Mutational Analysis of Insertion Sequence 50 (IS50) and Transposon 5 (Tn5) Ends," Proceedings of the National Academy of Sciences (USA), Genetics, vol. 85, No. 7, pp. 2224-2228, Apr. 1988.
Mallender et al., "Construction, Expression, and Activity of a Bivalent Bispecific Single-Chain Antibody," The Journal of Biological Chemistry, vol. 269, No. 1, pp. 199-206, Jan. 1994.

(56) References Cited

OTHER PUBLICATIONS

Manis, et al., "Mechanism and Control of Class-Switch Recombination," Trends in Immunology, vol. 23, Issue 1, pp. 31-39, Jan. 2002.

Marcello et al., "Lack of Tyrosylprotein Sulfotransferase-2 Activity Results in Altered Sperm-Egg Interactions and Loss of ADAM3 and ADAM6 in Epididymal Sperm," The Journal of Biological Chemistry, vol. 286, No. 15, pp. 13060-13070, Apr. 2011.

Martensson et al., "Role of the surrogate light chain and the pre-B-cell receptor in mouse B-cell development," Immunology, vol. 101, pp. 435-441, 2000.

Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.

Mattila, P.S., et al., "Extensive Allelic Sequence Variation in the J Region of the Human Immunoglobulin Heavy Chain Gene Locus," European Journal of Immunology, vol. 25, No. 9, pp. 2578-2582, Sep. 1995.

Maul et al., "AID and Somatic Hypermutation," Advances in Immunology, vol. 105, pp. 159-191, 2010.

McCreath et al., "Production of Gene-Targeted Sheep by Nuclear Transfer From Cultured Somatic Cells," Nature, vol. 405, pp. 1066-1070, Jul. 2000.

Mejia et al., "The Assembly of Large BACs by in Vivo Recombination," Genomics, vol. 70, pp. 165-170, 2000.

Milner, et al, "Polymorphism and Utilization of Human $V_H$ Genes," Annals of the New York Academy of Sciences, vol. 764, pp. 50-61, Sep. 1995.

Mir, Kalim U., "Sequencing Genomes: From Individuals to Populations," Briefings in Functional Genomics and Proteomics, vol. 8, No. 5, pp. 367-378, 2009.

Moran, Nuala, "Mouse Platforms Jostle for Slice of Humanized Antibody Market," Nature Biotechnology, vol. 31, pp. 267-268, 2013.

Moreau et al., "The SV40 72 Base Repair Repeat Has a Striking Effect on Gene Expression Both in SV40 and Other Chimeric Recombinants," Nucleic Acids Research, vol. 9, No. 22, pp. 6047-6068, 1981.

Moreno et al., "The Emerging Role of Matrix Metalloproteases of the ADAM Family in Male Germ Cell Apoptosis," Spermatogenesis, vol. 1, No. 3, pp. 195-208, Jul./Aug./Sep. 2011.

Mouellic et al., "Pattern of Transcription of the Homeo Gene Hox-3.1 in the Mouse Embryo," Genes and Development, vol. 2, pp. 125-135, 1988.

Mortuza et al., "Immunoglobulin Heavy-Chain Gene Rearrangement in Adult Acute Lymphoblastic Leukemia Reveals Preferential Usage of JH-Proximal Variable Gene Segments," Blood, vol. 97, No. 9, pp. 2716-2726, May 2001.

Murphy, et al., "Mice with Megabase Humanization of Their Immunoglobulin Genes Generate Antibodies as Efficiently as Normal Mice," Proceedings of the National Academy of Sciences, vol. 111, No. 14, pp. 5153-5158, Apr. 2014.

Nagle, "Regeneron Helps Make Sanofi Velocimmune to Its 'Weak' Pipeline," Outsourcing-Pharmac.com, 2 pages, Dec. 3, 2007.

Nandi et al., "Regulated Expression of Genes Inserted at the Human Chromosomal B-Globin Locus by Homologous Recombination," Proceedings of the National Academy of Sciences (USA), Cell Biology, vol. 85, pp. 3845-3849, Jun. 1998.

Narayanan et al., "Bacterial Artificial Chromosome Mutagenesis Using Recombineering" Journal of Biomedicine and Biotechnology, vol. 2011, 10 pages, Dec. 2010.

Nelson et al., "Development Trends for Human Monoclonal Antibody Therapeutics," Nature Reviews Drug Discovery, vol. 9, pp. 767-774, Oct. 2010.

Neuberger et al., "Somatic Hypermutation," Current Opinion in Immunology, vol. 7, pp. 248-254, 1995.

Niemann et al., "Transgenic Farm Animals: Present and Future," Review of Science and Technology, vol. 24, No. 1, pp. 285-298, Apr. 2005.

Oancea et al., "Expression of the (Recombinant) Endogenous Immunoglobulin Heavy-Chain Locus requires the Intronic Matrix Attachment Regions," Molecular and Cellular Biology, vol. 17, No. 5, pp. 2658-2668, May 1997.

Oberdoerffer et al., "Unidirectional Cre-Mediated Genetic Inversion in Mice Using the Mutant Loxp Pair Lox66/Lox71," Nucleic Acids Research, vol. 31, No. 22, pp. 1-7, Nov. 2003.

Ohlin, et Al., "The Human Antibody Repertoire to Infectious Agents: Implications for Disease Pathogenesis," Molecular Immunology, vol. 40, Issue 1, pp. 1-11, Sep. 2003.

Ohm-Laursen, et al., "Identification of Two New Alleles, IGHV3-23*04 and IGHJ6*04, and the Complete Sequence of the IGHV3-H Pseudogene in the Human Immunoglobulin Locus and Their Prevalences in Danish Caucasians," Immunogenetics, vol. 57, No. 9, pp. 621-627.

Osborn et al., "High-Affinity IgG Antibodies Develop Naturally in Ig-Knockout Rats Carrying Germline Human IgH/Ig K/Ig λ Loci Bearing the Rat $C_H$ Region," The Journal of Immunology, vol. 190, No. 4, pp. 1481-1490, Feb. 2013.

Osoegawa et al., "Bacterial Aartificial Chromosome Libraries for Mouse Sequencing and Functional Analysis," Genome Research, vol. 10, No. 1, pp. 16-28, Jan. 2000.

Pavlicek et al., "Ancient Transposable Elements, Processed Pseudogenes, and Endogenous Retroviruses," Genomic Disorders, pp. 57-72, 2006.

Pelham et al., "Expression of a *Drosophila* Heat Shock Protein in Mammalian Cells: Transient Association with Nucleoli after Heat Shock," Philosophical Transactions of the Royal Society, vol. 307, No. 1132, pp. 301-307, Dec. 1984.

Perlot et al., "Antisense Transcripts From Immunoglobulin Heavy-Chain Locus V(D)J and Switch Regions," Proceedings of the National Academy of Sciences, vol. 105, No. 10, pp. 3843-3848, Mar. 2008.

Perlot et al., "Cis-Regulatory Elements and Epigenetic Changes Control Genomic Rearrangements of the IgH Locus," Advances in Immunology, vol. 99, pp. 1-32, 2008.

Pettitt, et al., "Agouti C57BL/6N Embryonic Stem Cells for Mouse Genetic Resources," Nature Methods, vol. 6, No. 7, pp. 493-495, Jul. 2009.

Plasterk et al., "Resident Aliens: The Tc1/Mariner Superfamily of Transposable Elements," Trends in Genetics, vol. 15, No. 8, pp. 326-333, Aug. 1999.

Ponsel, et al., "High Affinity, Developability and Functional Size: The Holy Grail of Combinatorial Antibody Library Generation," Molecules, vol. 16, No. 5, pp. 3675-3700, May 2011.

Popov et al., "A Human Immunoglobulin λ Locus Is Similarly Well Expressed in Mice and Humans," Journal of Experimental Medicine, vol. 189, No. 10, pp. 1611-1619, May 1999.

Pramanik, et al. "Segmental Duplication as One of the Driving Forces Underlying the Diversity of the Human Immunoglobulin Heavy Chain Variable Gene Region," BMC Genomics, vol. 12, No. 78, Jan. 2011.

Primakoff et al., "Penetration, Adhesion, and Fusion in Mammalian Sperm-Egg Interaction," Science, vol. 296, pp. 2183-2185, Jun. 2002.

Primakoff et al., "The ADAM Gene Family: Surface Proteins With Adhesion and Protease Activity," Trends in Genetics, vol. 16, No. 2, pp. 83-87, Feb. 2000.

Puente et al., "Comparative Genomic Analysis of Human and Chimpanzee Proteases," Genomics, vol. 86, No. 6, pp. 638-647, Dec. 2005.

Prosser, et al., "Mosaic Complementation Demonstrates a Regulatory Role for Myosin Viia in Actin Dynamics of Stereocilia," Molecular and Cellular Biology, vol. 28, No. 5, pp. 1702-1712, Mar. 2008.

Prosser, et al., "A Resource of Vectors and ES Cells for Targeted Deletion of Micrornas in Mice," Nature Biotechnology, vol. 29, No. 9, pp. 840-845, Sep. 2011.

(56) References Cited

OTHER PUBLICATIONS

Pruzina, et al., "Human Monoclonal Antibodies to HIV-1 Gp140 From Mice Bearing YAC-Based Human Immunoglobulin Transloci," Protein Engineering, Design & Selection, vol. 24, No. 10, pp. 791-799, Aug. 2011.
Qu et al., "Gene Targeting of ErbB3 Using a Cre-Mediated Unidirectional DNA Inversion Strategy," Technology Report, Genesis, vol. 44, pp. 477-486, 2006.
Ray, et al., "Ectopic Expression of a C-Kitw42 Minigene in Transgenic Mice: Recapitulation of W Phenotypes and Evidence for C-Kit Function in Melanoblast Progenitors," Genes & Development, vol. 5, pp. 2265-2273, 1991.
Raynard et al., "Cis-Acting Regulatory Sequences Promote High-Frequency Gene Conversion Between Repeated Sequences in Mammalian Cells," Nucleic Acids Research, vol. 32, No. 19, pp. 5916-5927, Nov. 2004.
Reddy et al., "Monoclonal Antibodies Isolated Without Screening by Analyzing the Variable-Gene Repertoire of Plasma Cells," Nature Biotechnology, vol. 28, No. 9, pp. 965-971, Sep. 2010.
Regeneron, "Big Pharma Vies for Mice," Nature Biotechnology, vol. 25, No. 6, p. 613, Jun. 2007.
Retter, "Sequence and Characterization of the Ig Heavy Chain Constant and Partial Variable Region of the Mouse Strain 129S1," The Journal of Immunology, vol. 179, pp. 2419-2427, 2007.
Rivera, et al., "Genetic Background and the Dilemma of Translating Mouse Studies to Humans," Immunity, vol. 28, No. 1, pp. 1-4, Jan. 2008.
Rodriguez, et al., "High-Efficiency Deleter Mice Show That FLPe Is an Alternative to Cre-loxP," Nature Genetics, vol. 25, pp. 139-140, Jun. 2000.
Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process," Journal of Immunology, vol. 172, pp. 3382-3384, 2004.
Sakai et al., "Recombination and Transcription of the Endogenous Ig Heavy Chain Locus is Effected by the Ig Heavy Chain Intronic Enhancer Core Region in the Absence of the Matrix Attachment Regions," Proceedings of the National Academy of Sciences, vol. 96, pp. 1526-1531, Feb. 1999.
Sarkar et al., "Molecular Evolutionary Analysis of the Widespread PiggyBac Transposon Family and Related "Domesticated" Sequences," Molecular Genetics and Genomics, vol. 270, pp. 173-180, 2003.
Sasso et al., "Expression of the Immunoglobulin Vh Gene 51p1 is Proportional to its Germline Gene Copy Number," Journal of Clinical Investigation, vol. 97, No. 9, pp. 2074-2080, May 1996.
Sasso, et al., "Ethnic Differences in Polymorphism of an Immunoglobulin $V_h3$ Gene," Journal of Clinical Investigation, vol. 96, No. 3, pp. 1591-1600, Sep. 1995.
Sauer, "Functional Expression of the Cre-Lox Site-Specific Recombination System in the Yeast *Saccharomyces cerevisiae*," Molecular and Cellular Biology, vol. 7, No. 6, pp. 2087-2096, Jun. 1987.
Sauer et al., "Cre-Stimulated Recombination at loxP-Containing DNA Sequences Placed into the Mammalian Genome," Nucleic Acids Research, vol. 17, No. 1, pp. 147-161, 1989.
Sauer et al., "Site-Specific DNA Recombination in Mammalian Cells by the Cre Recombinase of Bacteriophage P1," PNAS (USA), Genetics, vol. 85, pp. 5166-5170, 1988.
Schnutgen et al., "A Directional Strategy for Monitoring Cre-Mediated Recombination at the Cellular Level in the Mouse," Nature Biotechnology, vol. 21, pp. 562-565, May 2003.
Schlake et al., "Use of Mutated FLP Recognition Target (FRT) Sites for the Exchange of Expression Cassettes at Defined Chromosomal Loci," Biochemistry, vol. 33, pp. 12746-12751, 1994.
Schrock et al., "Comparative Genomic Hybridization (CGH)—Detection of Unbalanced Genetic Aberrations Using Conventional Micro-Array Techniques," Molecular Cytogenetics, Unit 8.12.1, Supplement 18, 30 pages, 2001.
Schroeder, et al., "Preferential Utilization of Conserved Immunoglobulin Heavy Chain Variable Gene Segments During Human Fetal Life," Proceedings of the National Academy of Sciences (USA), vol. 87, pp. 6146-6150, Aug. 1990.
Schweinfest et al., "A Heat-Shock-Inducible Eukaryotic Expression Vector," Gene, vol. 71, No. 1, pp. 207-210, Nov. 1988.
Scott, "Mice with a Human Touch," Nature Biotechnology, vol. 25, pp. 1075-1077, Dec. 2007.
Seals, et al., "The Adams Family of Metalloproteases: Multidomain Proteins With Multiple Functions," Genes & Development, vol. 17, No. 1, pp. 7-30, Jan. 2003.
Seed et al., "Purification of Genomic Sequences From Bacteriophage Libraries by Recombination and Selection In Vivo," Nucleic Acids Research, vol. 11, No. 8, pp. 2427-2445, 1983.
Sen, et al., "Multiple Nuclear Factors Interact With the Immunoglobulin Enhancer Sequences," Cell, vol. 46, pp. 705-716, Aug. 1986.
Seong, et al., "To Knockout in 129 or in C57BL/6: That is the Question," Trends in Genetics, vol. 20, No. 2, pp. 59-62, Feb. 2004.
Serwe et al., "V(D)J Recombination in B Cells is Impaired But Not Blocked by Targeted Deletion of the Immunoglobulin Heavy Chain Intron Enhancer," The EMBO Journal, vol. 12, No. 6, pp. 2321-2327, 1993.
Shaul, et al., "Homologous Recombination Between a Defective Virus and a Chromosomal Sequence in Mammalian Cells," Proceedings of the National Academy of Sciences (USA), vol. 89, pp. 3781-3784, Jun. 1985.
Shi, et al., "Comparative Analysis of Human and Mouse Immunoglobulin Variable Heavy Regions from IMGT/LIGM-DB with IMGT/HighV-QUEST," Theoretical Biology and Medical Modelling, vol. 11, pp. 1-11, Nov. 2014.
Shimizu et al., "Immunoglobulin Double-Isotype Expression by Trans-mRNA in a Human Immunoglobulin Transgenic Mouse," Proceedings of the National Academy of Sciences (USA), Immunology, vol. 86, pp. 8020-8023, Oct. 1989.
Shultz, et al., "Humanized Mice in Translational Biomedical Research," The Journal of Immunology, vol. 7, No. 2, pp. 118-130, Feb. 2007.
Sirac, et al., "Role of the Monoclonal K Chain V Domain and Reversibility of Renal Damage in a Transgenic Model of Acquired Fanconi Syndrome," Blood, vol. 108, No. 2, pp. 536-543, Jul. 2006.
Skarnes, et al., "A Conditional Knockout Resource for the Genome-Wide Study of Mouse Gene Function," Nature, vol. 474, pp. 337-342, Jun. 2011.
Simpson, et al., "Genetic Variation Among 129 Substrains and its Importance for Targeted Mutagenesis in Mice," Nature Genetics, vol. 16, pp. 19-27.
Skoultchi et al., "Expression of Genes Inserted at the Human B-Globin Locus by Homologous Recombination," Developmental Control of Globin Gene Expression, vol. 251, pp. 581-594, 1987.
Smithies, "Direct Alteration of a Gene in the Human Genome," Journal of Inheritable Metabolic Disease, vol. 9, Suppl. 1, pp. 92-97, 1986.
Smithies et al., "Insertion of DNA Sequences Into the Human Chromosomal B-Globin Locus by Homologous Recombination," Nature, vol. 317, No. 19, pp. 230-234, Sep. 1985.
Sohn et al., "Somatic Hypermutation of an Immunoglobulin μ Heavy Chain Transgene," Journal of Experimental Medicine, vol. 177, pp. 493-504, Feb. 1993.
Song et al., "Accurate Modification of a Chromosomal Plasmid by Homologous Recombination in Human Cells," Proceedings of the National Academy of Sciences (USA), Genetics, vol. 84, pp. 6820-6824, Oct. 1987.
Sonoda et al., "B Cell Development under the Condition of Allelic Inclusion," Immunology, vol. 6, pp. 225-233, Mar. 1997.
Storb et al., "Physical Linkage of Mouse Genes by Pulsed-Field Gel Electrophoresis Suggests that the Rearrangement Process Favors Proximate Target Sequences," Molecular and Cellular Biology, vol. 9, No. 2, pp. 711-718, Feb. 1989.
Stevens et al., "Human Antibody Discovery, VelocImmune—A Novel Platform," Pharma Focus Asia, Clinical Trials Issue 8, pp. 1-5, 2008.
Suárez, et al., "Rearrangement of Only One Human IGHV Gene is Sufficient to Generate a Wide Repertoire of Antigen Specific Antibody Responses in Transgenic Mice," Molecular Immunology, vol. 43, No. 11, pp. 1827-2835, Dec. 2006.

(56) References Cited

OTHER PUBLICATIONS

Taki et al., "Targeted Insertion of a Variable Region Gene into the Immunoglobulin Heavy Chain Locus," Science, vol. 262, pp. 1268-1271, Nov. 1993.

Talbot et al., "Cell Adhesion and Fertilization: Steps in Oocyte Transport, Sperm-Zona Pellucida Interactions, and Sperm-Egg Fusion," Biology of Reproduction, vol. 68, No. 1, pp. 1-9, Jan. 2003.

Te Riele, et al., "Highly Efficient Gene Targeting in Embryonic Stem Cells Through Homologous Recombination with Isogenic DNA Constructs," Proceedings of the National Academy of Sciences (USA), vol. 89, pp. 5128-5132, Jun. 1992.

Thomas et al., "High Frequency Targeting of Genes to Specific Sites in the Mammalian Genome," Cell, vol. 44, pp. 419-428, Feb. 1986.

Thomas et al., "Introduction of Homologous DNA Sequences Into Mammalian Cells Induces Mutations in the Cognate Gene" Nature, vol. 324, Nov. 1986.

Thomas et al., "Site-Directed Mutagenesis by Gene Targeting in Mouse Embryo-derived stem cells," Cell, vol. 51, pp. 503-512, Nov. 1987.

Tomizuka, et al., "Double Trans-Chromosomic Mice: Maintenance of Two Individual Human Chromosome Fragments Containing Ig Heavy and K Loci and Expression of Fully Human Antibodies," Proceedings of the National Academy of Sciences (USA), vol. 97, No. 2, pp. 722-727, Jan. 2000.

Torres et al., "Laboratory Protocols for Conditional Gene Targeting," Institute for Genetics, University of Cologne, pp. 37-40, 1997.

Ungrin et al., "Strict Control of Telomerase Activation Using Cre-Mediated Inversion", BMC Biotechnology, vol. 6, pp. 1-9, 2006.

Valenzuela, et al., "High-Throughput Engineering of the Mouse Genome Coupled with High-Resolution Expression Analysis," Nature Biotechnology vol. 21, No. 6, p. 652-659 and vol. 21, No. 7, p. 822, Jun. 2003.

Van Spriel, et al., "Immunotherapeutic Perspective for Bispecific Antibodies," Immunology Today, vol. 21, No. 8, pp. 391-397, Aug. 2000.

Vassilieva et al., "Establishment of SSEA-1- and Oct-4 Expressing Rat Embryonic Stem-Like Cell Lines and Effects of Cytokines of the IL-6 Family on Clonal Growth," Experimental Cell Research, vol. 258, pp. 361-373, 2000.

Vasicek, et al., "Structure and Expression of the Human Immunoglobulin λ Genes," Journal of Experimental Medicine, vol. 172, pp. 609-620, Aug. 1990.

Venken et al., "P[acman]: A BAC Transgenic Platform for Targeted Insertion of Large DNA Fragments in *D. melanogaster*," Science, vol. 314, pp. 1747-1751, Dec. 2006.

Vora et al., "Altering the Antibody Repertoire via Transgene Homologous Recombination: Evidence for Global and Clone-autonomous Regulation of Antigen-driven B Cell Differentiation," Journal of Experimental Medicine, vol. 181, pp. 271-281, Jan. 1995.

Wallace et al. "Manipulating the Mouse Genome to Engineer Precise Functional Syntenic Replacements with Human Sequence," Cell, vol. 128, No. 1, pp. 197-209, Jan. 2007.

Wang et al., "AID Upmutants Isolated Using a High-Throughput Screen Highlight the Immunity/Cancer Balance Limiting DNA Deaminase Activity," Nature Structural & Molecular Biology, vol. 16, No. 7, Jul. 2009.

Wang et al., "Altering the Spectrum of Immunoglobulin V Gene Somatic Hypermutation by Modifying the Active Site of AID," Journal of Experimintal Medicine, vol. 207, No. 1, pp. 141-153, Jan. 2010.

Wang et al. "Catching a Moving Target," Science, Biochemistry, vol. 333, pp. 834-835, Aug. 2011.

Wang, et al., "Chromosomal Transposition of PiggyBac in Mouse Embryonic Stem Cells," Proceedings of the National Academy of Sciences (USA), vol. 105, No. 27, pp. 9290-9295, Jul. 2008.

Wang, et al., "Many Human Immunoglobulin Heavy-Chain IGHV Gene Polymorphisms Have Been Reported in Error," Immunology and Cell Biology, vol. 86, No. 2, pp. 111-115, Feb. 2008.

Waterson, et al., "Initial Sequencing and Comparative Analysis of the Mouse Genome," Nature, vol. 420, No. 6915, pp. 520-562, Dec. 2002.

White, et al, "Genome-Wide Generation and Systematic Phenotyping of Knockout Mice Reveals New Roles for Many Genes," Cell, vol. 154, No. 2: pp. 452-464, Jul. 2013.

Wilkie et al., "Analysis of the Integrant in MyK-103 Transgenic Mice in Which Males Fail to Transmit the Integrant," Molecular and Cellular Biology, pp. 1646-1655, May 1987.

Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, vol. 167, No. 1, pp. 257-263, Jul. 2001.

Xu, et al., "Combinatorial Surrobody Libraries," Proceedings of the National Academy of Sciences (USA), vol. 105, No. 31, pp. 10756-10761, Aug. 2008.

Yancopoulous et al., "Preferential Utilization of the Most JH-Proximal VH Gene Segments in Pre-B-Cell Lines," Nature, vol. 311, pp. 727-733, 1984.

Zhao, Shaving, "A Comprehensive BAC Resource," Nucleic Acids Research, vol. 29, No. 1, Jan. 2001.

Zheng et al., Engineering Mouse Chromosomes with Cre-loxP: Range, Efficiency, and Somatic Applications, Molecular and Cellular Biology, vol. 20, No. 2, pp. 648-655, Jan. 2000.

Zou et al., "Cre-loxP-Mediated Gene Replacement: A Mouse Strain Producing Humanized Antibodies," Current Biology, vol. 4, No. 12, pp. 1099-1104, Dec. 1994.

GenBank Accession No. X97051 S64822, accessed Aug. 6, 2014, 29 pages.

Nucleotide Sequence RID Y55HBK1W114, accessed Aug. 6, 2014, 2 pages.

Affidavits Evidencing Murphy Slides as Printed Publication, 84 pages, dated Jun. 20, 2016.

Aguilera R.J. et al., "Characterization of immunoglobulin enhancer deletions in murine plasmacytomas," The EMBO Journal, 1985, vol. 4 (13B), pp. 3689-3693.

Board of Appeal of the European Patent Office, Datasheet for the Decision of Nov. 9, 2015 for Application No. 02709544.7, Case T 2220/14-3.3.08, 83 pages.

Deftos, M., et al., "Defining the Genetic Origins of Three Rheumatoid Synovium-derived IgG Rheumatoid Factors," Journal of Clinical Investigations, Jun. 1994, vol. 93, pp. 2545-2553.

Donohoe M.E., et al., "Transgenic Human λ5 Rescues the Murine λ5 Nullizygous Phenotype," Journal of Immunology, 2000, vol. 164, pp. 5269-5276.

European Patent Office, F. Chambonnet, Authorized Officer, International Search Report for Application No. PCT/GB2012/052380, dated Jan. 3, 2013, 17 pages, together with the Written Opinion of the International Searching Authority.

European Patent Office, Julien Landre, Authorized Officer, International Search Report for Application No. PCT/GB2012/052670, dated Feb. 14, 2013, 12 pages, together with the Written Opinion of the International Searching Authority.

European Patent Office, Communication pursuant to Rule 114(2) EPC regarding 14772198.9, dated Mar. 30, 2016, 16 pages.

European Patent Office, Examination Report for Application No. 12762378.3, dated Jun. 8, 2016, 5 pages.

European Patent Office, Examination Report for Application No. 13711119.1, dated Jul. 13, 2016, 6 pages.

European Patent Office, Examination Report for Application No. 14176740.0, dated Jun. 6, 2016, 5 pages.

Gratz S. et al., "Genome Engineering of *Drosophila* with the CRISPR RNA-Guided Cas9 Nuclease," Genetics, Aug. 2013, vol. 194, pp. 1029-1035.

Grund M., European Patent Attorney, Grund Intellectual Property Group, Third-Party Observations according to Article 115 EPC regarding 11705964.2, dated Aug. 5, 2016, 11 pages.

Grund M., European Patent Attorney, Grund Intellectual Property Group, Third-Party Observations according to Article 115 EPC regarding 12772122.3, dated May 17, 2016, 7 pages.

(56) References Cited

OTHER PUBLICATIONS

Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations regarding Application No. PCT/GB2012/052956, dated Mar. 26, 2014, 2 pages.
Guo, Y., et al., "A Preliminary Analysis of the Immunoglobulin Genes in the African Elephant (*Loxodonta africana*)," PLoS ONE, Feb. 2011, vol. 6 (2), pp. e16889-1-e16889-14.
Huang, D., et al., "Sequence Analyses of Three Immunoglobulin G Anti-virus Antibodies Reveal Their Utilization of Autoantibody-related Immunoglobulin Vh Genes, but Not Vλ Genes," Journal of Clinical Investigations, Dec. 1992, vol. 90, pp. 2197-2208.
Jasper, P.J., et al., "B lymphocyte deficiency in IgH-transgenic rabbits," European Journal of Immunology, 2007, vol. 37, pp. 2290-2299.
Jones, Brendan T., Attorney for Applicant, Third-Party Pre-Issuance Submission Under 37 CFR Sec. 1.290 in U.S. Appl. No. 15/018,670, 26 pages, dated Aug. 12, 2016.
Kawasaki, K., et al., "One-Megabase Sequence Analysis of the Human Immunoglobulin λ Gene Locus," Genome Research, 1997, vol. 7, pp. 250-261.
LeFranc M.P. et al., "Immunoglobulin Lambda (IGL) Genes of Human and Mouse," Molecular Biology of B Cells, Chapter 4, p. 47, 2004 (Edtrs. Honjo et al.).
LeFranc M.P., et al., "The Immunoglobulin Facts Book—Annex 3," IGHJ group, Academic Press, ISBN:9-12-441351-X, 2001, 4 pages.
Lyon C., Attorney for Applicant, Third-Party Pre-Issuance Submission Under 37 CFR Sec. 1.290 in U.S. Appl. No. 14/543,359, dated Nov. 13, 2015, 36 pages.
Meng L., Second Declaration of Dr. Meng (Amy) Li, dated Sep. 5, 2016, 2 pages.
Mills F., et al., "Enhancer Complexes Located Downstream of Both Human Immunoglobulin C a Genes," The Journal of Experimental Medicine, Sep. 1997, vol. 186 (6), pp. 845-858.
Minaee S., et al., "Mapping and Functional Analysis of Regulatory Sequences in the Mouse Lambda5-VpreB1 Domain," Molecular Immunology, 2005, vol. 42 (11), pp. 1283-1292.
Mullins, L.J., et al., "Transgenesis in the Rat and Larger Mammals," Perspective Series: Molecular Medicine in Genetically Engineered Animals, Journal of Clinical Investigation, Apr. 1996, vol. 97 (7), pp. 1557-1560.
Murphy, D., "BAC-based Modifications of the Mouse Genome: The Big and the Backward," Wellcome Trust Advanced Course: Genetic Manipulation of ES Cells, dated Nov. 3, 2009, VP Target Discovery, Regeneron Pharmaceuticals, Inc., 58 pages.
Neuberger M.S., "Expression and regulation of immunoglobulin heavy chain gene transfected into lymphoid cells," The EMBO Journal, 1983, vol. 2 (8), pp. 1373-1378.
Pear W.S., et al., "Localization of the Rat Immunoglobulin Heavy Chain Locus to Chromosome 6," Immunogenetics, 1986, vol. 23 (6), pp. 393-395.
Pera, M.F., et al., "Human embryonic stem cells," Journal of Cell Science, 2000, vol. 113, pp. 5-10.
Pettersson S., et al., "A second B cell-specific enhancer 3' of the immunoglobulin heavy-chain locus," Nature, Mar. 1990, vol. 344, pp. 165-168.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Sabbattini P., et al., "Analysis of Mice with Single and Multiple Copies of Transgenes Reveals a Novel Arrangement for the λ5-VpreB1 Locus Control Region," Molecular and Cellular Biology, Jan. 1999, vol. 19 (1), pp. 671-679.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Tanimoto Y., et al., "Embryonic Stem Cells Derived from C57BL/6J and C57BL/6N Mice," Comparative Medicine, 2008, vol. 58 (4), pp. 347-352.
Tong C., et al., "Production of p53 gene knockout rats by homologous recombination in embryonic stem cells," Nature, Sep. 2010, vol. 467 (7312), pp. 211-213.
Van Loo, P.F., et al., "Surrogate-Light-Chain Silencing Is Not Critical for the Limitation of Pre-B Cell Expansion but Is for the Termination of Constitutive Signaling," Immunity, Sep. 2007, vol. 27, pp. 468-480.
Wikipedia, "Monoclonal antibodies," 2008, 8 pages.
Wikipedia, "Polyclonal antibodies," 2008, 5 pages.
MacDonald L., et al., Poster: "Velocimmune Technology Extended to Humanization of Several Megabases of Complex" and evidence of unavailability, 2006, 42 pages.
Stevens S., et al., Poster: "VelocImmuneTM: Humanization of immunoglobulin loci using VolociGene technology" and evidence of unavailability, 2006, 42 pages.
2006 MUGEN Conference (Abstracts 1-52), 52 pages.
Adams D.J. et al., "Contemporary approaches for modifying the mouse genome," *Physiological Genomics*, vol. 34, 2008, pp. 225-238.
Adams D.J. et al., "Mutagenic Insertion and Chromosome Engineering Resource (MICER)," *Nature Genetics*, vol. 36 (8), Aug. 2004, pp. 867-871.
Arthur J.S. et al., "Gene-Targeting Vectors," Chapter 9, *Transgenesis Techniques, Principles and Protocols*, Third edition, 2009 (24 pages, including cover sheet, copyright and preface pages and table of contents), pp. 127-144.
Asenbauer H. et al., "The immunoglobulin lambda light chain enhancer consists of three modules which synergize in activation of transcription," *European Journal of Immunology*, 1999, vol. 29, pp. 713-724.
Baer A. et al., "Coping with kinetic and thermodynamic barriers: RMCE, an efficient strategy for the targeted integration of transgenes," *Current Opinions in Biotechnology*, Oct. 2001, vol. 12 (5), pp. 473-480.
Birling M.C. et al., "Site-Specific Recombinases for Manipulation of the Mouse Genome," Chapter 16, *Transgenesis Techniques, Principles and Protocols*, Third edition, 2009 (25 pages, including cover sheet, copyright and preface pages and table of contents), pp. 245-263.
De Wildt R.M. et al., "Analysis of Heavy and Light Chain Pairings Indicates that Receptor Editing Shapes the Human Antibody Repertoire," *Journal of Molecular Biology*, 1999, vol. 285, pp. 895-901.
Declerck P. et al., "Generation of Monoclonal Antibodies against autologous Proteins in Gene-inactivated Mice," *The Journal of Biological Chemistry*, Apr. 1995, vol. 270 (15), pp. 8397-8400.
European Patent Office, Examination Report for Application No. 12778780.2, dated Oct. 14, 2016, 3 pages.
European Patent Office, Extended European Search Report for Application No. 16189625.3, dated Nov. 23, 2016, 8 pages.
Glaser S. et al., "Current issues in mouse genome engineering," *Nature Genetics*, Nov. 2005, Vo. 37 (11), pp. 1187-1193.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 14176740.0, dated Nov. 2, 2016, 4 pages.

(56) References Cited

OTHER PUBLICATIONS

Guan C. et al., "A Review of Current Large-Scale Mouse Knockout Efforts," *Genesis*, vol. 48, 2010, pp. 73-85.
Hamers-Caterman C. et al., "Naturally occurring antibodies devoid of light chains," *Nature*, Jun. 1993, vol. 363, pp. 446-448.
Hsu E., "The plasticity of immunoglobulin gene systems in evolution," *Immunology Reviews*, vol. 210, Apr. 2006, pp. 8-26.
Jones, Brendan T., Attorney for Applicant, Third-Party Pre-Issuance Submission Under 37 CFR Sec. 1.290 in U.S. Appl. No. 15/016,211, 59 pages, dated Oct. 4, 2016.
Jones, Brendan T., Attorney for Applicant, Third-Party Pre-Issuance Submission Under 37 CFR Sec. 1.290 in U.S. Appl. No. 15/095,315, 26 pages, dated Sep. 16, 2016.
Kindt T.J. et al., "Organization and Expression of Immunoglobulin Genes," Chapter 5, *Immunology*, Sixth edition, 2007 (36 pages, including cover sheet and copyright page), pp. 111-144.
Kuzin I.I. et al, "Requirement for enhancer specificity in immunoglobulin heavy chain locus regulation," *Journal of Immunology*, Jun. 2008, vol. 180 (11), pp. 7443-7450.
Largaespada D.A., "Transposon Mutagenesis in Mice," *Methods in Molecular Biology*, vol. 530, 2009, pp. 379-390.
LeFranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.
Levin A.M. et al., "Optimizing the affinity and specificity of proteins with molecular display," *Molecular Biosystems*, 2006, vol. 2, pp. 49-57.
Liang Q. et al., "Extensive genomic copy number variation in embryonic stem cells," *Proceedings of the National Academy of Sciences of the U.S.A.*, Nov. 2008, vol. 105 (45), pp. 17453-17456.
MacDonald L., Declaration of Lynne E. Macdonald, dated Jun. 29, 2016, 4 pages.
Marchalonis J.J. et al., "Emergence of the immunoglobulin family: conservation in protein sequence and plasticity in gene organization," *Glycobiology*, vol. 6, 1996, pp. 657-663.
Mester G., European Patent Attorney, Grund Intellectual Property Group, Third-Party Observations according to Article 115 EPC regarding EP 12778780.2, dated Sep. 30, 2016, 5 pages.
Moffatt S. et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.
Munoz M. et al., "Constraints to Progress in Embryonic Stem Cells from Domestic Species," *Stem Cell Rev. and Rep.*, 2009, vol. 5, pp. 6-9.
Murphy et al., The Generation of Lymphocyte Antigen Receptors, Ch. 4, excerpt from Janeway's Immunobiology, Seventh edition, 2008, p. 158.
Oumard A. et al., "Recommended method for chomosome exploitation: RMCE-based cassette-exchange systems in animal cell biotechnology," *Cytotechnology*, 2006, vol. 50, pp. 93-108.
Perez-Luz S. et al., "Factor VIII mRNA expression from a BAC carrying the intact locus made by homologous recombination," *Genomics*, 2007, vol. 90, pp. 610-619.
Presta L., "Molecular engineering and design of therapeutic antibodies," *Current Opinion in Immunology*, 2008, vol. 20, pp. 460-470.
Renaut L. et al., "Affinity Maturation of Antibodies: Optimized Methods to Generate High-Quality ScFv Libraries and Isolate IgG Candidates by High-Throughput Screening," *Antibody Engineering: Methods and Protocols*, Chapter 26, Second Edition, 2012, vol. 907, pp. 451-461.
Schroeder, Jr. H.W., "Similarity and divergence in the development and expression of the mouse and human antibody repertoires," *Developmental and Comparative Immunology*, vol. 30, 2006, pp. 119-135.
Sopher B. et al., "Efficient recombination-based methods for bacterial artificial chormosome fusin and mutagenesis," *Gene*, 2006, vol. 371, pp. 136-143.
Sorrell D.A. et al., "Targeted modification of mammalian genomes," *Biotechnology Advances*, vol. 23, 2005, pp. 431-469.
Stephen R., Olswang, Response to Examination Report dated Jun. 6, 2016 for EP Application No. 14176740.0 as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Van Der Weyden L. et al., "Mouse Chromosome Engineering for Modeling Human Disease," Europe PMC Funders Group, Author Manuscript, Dec. 2008, 32 pages.
Van Dijk M., Declaration of Marcus Van Dijk with exhibits, Apr. 30, 2016, 139 pages.
Vieira P. et al., "The half-lives of serum immunoglobulins in adult mice," *European Journal of Immunology*, 1988, vol. 18, pp. 313-316.
Webpage corroborating non-confidential nature of 2006 MUGEN Conference, Athens (www.mugen.noe.org), accessed Aug. 9, 2016, 4 pages.
Zhang X. et al., "Combination of overlapping bacterial artificial chromosones by a two-step recobminogenic engineering method," *Nucleic Acids Research*, 2003, vol. 31 (15), pp. e81-1-e81-6.
Zhao Y. et al., "Physical Mapping of the Bovine Immunoglobulin Heavy Chain Constant Region Gene Locus," *Journal of Biological Chemistry*, 2003, vol. 278 (37), pp. 35024-35032.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
Beck J.A., et al., "Genealogies of mouse inbred strains," *Nature Genetics*, 2000, vol. 24, pp. 23-25 (with supporting table and chart).
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Bornstein, G.G. et al., "Development of a new fully human anti-CD20 monoclonal antibody for the treatment of B-cell malignancies", *Investigational New Drugs*, 2010, vol. 28, pp. 561-574.
Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.
Call L.M., et al., "A Cre-lox recombination system for the targeted integration of circular yeast artificial chromosomes into embryonic stem cells," *Human Molecular Genetics*, 2000, vol. 9 (12), pp. 1745-1751.
Carter T.C., et al., "Standardized Nomenclature for Inbred Strains of Mice," *Cancer Research*, 1952, vol. 12 (8), pp. 602-613.
Chia R., et al., "The origins and uses of mouse outbred stocks," *Nature Genetics*, 2005, vol. 37 (11), pp. 1181-1186.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
Collins A.M., et al., "The reported germline repertoire of human immunoglobulin kappa chain genes is relatively complete and accurate," *Immunogenetics*, 2008, vol. 60, pp. 669-676.
D'Eustachio P., et al., "Mouse Chromosome 12," *Mammalian Genome*, 1998, vol. 8, pp. S241-S257.
Engel H., et al., "Expression level of a transgenic $\lambda 2$ chain results in isotype exclusion and commitment to B1 cells," *European Journal of Immunology*, 1998, vol. 28, pp. 2289-2299.
European Patent Office, Extended European Search Report for Application No. 16151215.7, dated Mar. 16, 2016, 11 pages.
European Patent Office, Opposition against EP2517557 Animal Models and Therapeutic Molecules in the name of Kymab Limited pertaining to Application No. 12171793.8, dated Jan. 17, 2017, 39 pages.
Festing, M.F.W., et al., "Revised nomenclature for strain 129 mice," *Mammalian Genome*, 1999, vol. 10, p. 836.

(56) References Cited

OTHER PUBLICATIONS

Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.
Grandea A.G., III., et al., "Human antibodies reveal a protective epitope that is highly conserved among human and nonhuman influenza a viruses," *Proceedings of the National Academy of Sciences of the U.S.A.*, Jul. 2010, vol. 107 (28), pp. 12658-12663.
Grippo V., et al., "The Heavy Chain Variable Segment Gene Repertoire in Chronic Chagas' Heart Disease," *The Journal of Immunology*, Dec. 2009, vol. 182 (12), pp. 8015-8025.
Grund M., European Patent Attorney, Grund Intellectual Property Group, Third-Party Observations according to Article 115 EPC regarding 12762377.5, dated Jun. 20, 2017, 4 pages.
Grund M., European Patent Attorney, Grund Intellectual Property Group, Third-Party Observations according to Article 115 EPC regarding 12762378.3, dated Feb. 15, 2017, 6 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations according to Article 115 EPC regarding 16151215.7, dated Mar. 1, 2017, 4 pages.
Hong J., et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Jones, B.T., Attorney for Applicant, Third-Party Pre-Issuance Submission Under 37 CFR Sec. 1.290 in U.S. Appl. No. 15/232,122, filed Mar. 13, 2017, 32 pages.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones, B.T., Attorney for Applicant, Third-Party Pre-Issuance Submission Under 37 CFR Sec. 1.290 in U.S. Appl. No. 15/360,502, filed May 8, 2017, 40 pages.
Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. No. 15/214,963, filed Mar. 2, 2017, 42 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Jones B.T., Attorney for Applicant, Third-Party Pre-Issuance Submission Under 37 CFR Sec. 1.290 in U.S. Appl. No. 15/383,202, filed May 3, 2017, 23 pages.
Lefranc M.P., et al., Excerpts from "The Immunoglobulin FactsBook," *IMGT*, the international ImMunoGeneTics database, May 2001, 455 pages.
Magdelaine-Beuzelin C., et al., "Structure-function relationships of the variable domains of monoclonal antibodies approved for cancer treatment," *Critical Reviews in Oncology/Hematology*, 2007, vol. 64, pp. 210-225.
Martinez C., et al., "The Mouse (*Mus musculus*) Immunoglobulin Kappa Variable (IGKV) Genes and Joining (IGKV) Segments," *Experimental and Clinical Immunogenetics*, Jul. 1998, vol. 15, pp. 184-193.
Martínez P., et al., "Antibody Synthesis in Vitro," *Encyclopedia of Life Sciences*, 2005, pp. 1-8.
MGI, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Rock E.P., et al., "CDR3 Length in Antigen-specific Immune Receptors", *Journal of Experimental Medicine*, Jan. 1994, vol. 179, pp. 323-328.
Schonewald, S.L., Attorney for Applicant, Third-Party Pre-Issuance Submission Under 37 CFR Sec. 1.290 in U.S. Appl. No. 14/935,010, dated Aug. 19, 2016, 27 pages.
Sequence Listing to WO2008054606A2, 163 pages.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Shore, D.E., Attorney for Applicant, Third-Party Pre-Issuance Submission Under 37 CFR Sec. 1.290 in U.S. Appl. No. 15/199,575, filed May 31, 2017, 37 pages.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Suárez E. et al., "Human monoclonal antibodies produced in transgenic BABκ,λ mice recognising idiotypic immunoglobulins of human lymphoma cells," *Molecular Immunology*, 2004, vol. 41, pp. 519-526.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Wang X., et al., "Recombination, transcription, and diversity of a partially germline-joined VH in a mammal," *Immunogenetics*, 2012, vol. 64, pp. 713-717.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
Zou X., et al., "Subtle differences in antibody responses and hypermutation of lambda λ chains in mice with a disrupted x content region," *European Journal of Immunology*, 1995, vol. 25, pp. 2154-2162.
Adekar S.P., et al., "A Natural Human IgM Antibody that Neutralizes Botulinum Neurotoxin in vivo," *Hybridoma*, 2008, vol. 27 (2), pp. 65-69.
Aizenshtein E., et al., "Immunological complex for enhancement of innate immune response in passive vaccination," *Vaccine*, Jan. 2013, vol. 31 (4), pp. 626-631 [abstract only—1 page].
Australian IP Office, Examination Report No. 1 for Standard Patent Application for Application No. 2016244295, dated Aug. 18, 2017, 4 pages.
Australian IP Office, Notification of material filed by a third-party for Application No. 2012311288 in the name of Kymab Ltd., Applicant, dated Nov. 20, 2017, 14 pages.
Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.
Bradley A., Declarations of Allan Bradley (Tanamachi/Grosveld), as submitted in U.S. Appl. No. 13/416,684, 5 pages.
Bradley A., Declaration of Allan Bradley (commercial success), with exhibits, as submitted in U.S. Appl. No. 13/416,684, dated Feb. 12, 2015, 15 pages.
Bradley A., Declaration of Allan Bradley (mouse strain), with exhibits, as submitted in U.S. Appl. No. 13/416,684, dated Feb. 12, 2015, 68 pages.
Bradshaw, et al., "*Handbook of Cell Signalling*," 2010, Chapter 5, p. 33 (excerpt).

(56) References Cited

OTHER PUBLICATIONS

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Burton D.R., et al., "Antibody vs. HIB in a clash of evolutionary titans," *Proceedings of the National Academy of Sciences of the U.S.A*, Oct. 2005, vol. 102 (42), pp. 14943-14948.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

Davis C.G., et al., "Production of Human Antibodies from Transgenic Mice," *Antibody Engineering, Methods and Protocols, Methods in Mol. Biol.*, Chapter 10, 2004, pp. 191-200.

Delves P.J., et al., "Antibodies," Chapter 3, *Roitt's Essential Immunology*, Eleventh edition, 2006, pp. 37-60.

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.

Dörner T., et al., "Somatic hypermutation of human immunoglobulin heavy chain genes: targeting of RGYW motifs on both DNA strands," *European Journal of Immunology*, 1998, vol. 28, pp. 3384-3396.

Dübel S., "Therapeutic Antibodies—From Past to Future," in *Handbook of Therapeutic Antibodies—Technologies, Emerging Developments and Approved Therapeutics*, 2010, Chapter 1 (excerpt: pp. 3-5).

European Patent Office, Examination Report for Application No. 13723933.1, dated Jan. 17, 2018, 6 pages.

European Patent Office, Examination Report for Application No. 15188522.5, dated Aug. 11, 2017, 6 pages.

European Patent Office, Extended European Search Report for Application No. 17174426.1, dated Sep. 14, 2017, 10 pages.

European Patent Office, Extended European Search Report for Application No. 17196214.5, dated Jan. 2, 2018, 13 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages.

Frigerio B., et al., "Antibody Engineering as Opportunity for Selection and Organization of Anti-HIV Therapeutic Agents," *The Open Autoimmunity Journal*, 2010, vol. 2, pp. 127-138.

Genbank, "*Homo sapiens* partial IGHJ6 gene for immunoglobulin heavy joining 6, exon 1, allele 4," AJ879487.1, dated Jul. 26, 2016, 1 page.

Giudicelli V., et al., "IMGT/GENE-DB: a comprehensive database for human and mouse immunoglobulin and T cell receptor genes," *Nucleic Acids Research*, 2005, vol. 33, pp. D256-D261.

He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.

HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].

Hülseweh B., et al, "Human-like antibodies neutralizing Western equine encephalitis virus," *mAbs*, May/Jun. 2014, vol. 6 (3), pp. 718-727.

Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].

IMGT, *the International ImMunoGeneTics Information system database*, IMGT/GENE-DB entry for *Homo sapiens* IGHD3-9, 2007, 2 pages.

IMGT, *the International ImMunoGeneTics Information system database*, "Alignment of alleles: Human IGHJ6," dated Jun. 29, 2011, 1 page.

IMGT, *the International ImMunoGeneTics Information system database*, IMGT/GENE-DB entry for *Homo sapiens* IGHJ6, dated Jul. 26, 2017, version 3.1.17, 4 pages.

IMGT, *the International ImMunoGeneTics Information system database*, "IMGT/GENE-DB reference sequences," Nucleotide sequences of the four human IGHJ6 alleles, dated Jul. 26, 2017, version 3.1.17, 1 pages.

IMGT, *the International ImMunoGeneTics Information system database*, "IMGT/GENE-DB reference sequences," Amino acid sequences of the four human IGHJ6 alleles, dated Jul. 26, 2017, version 3.1.17, 7 pages.

Jackson S.M., et al., "Human B Cell Subsets," *Advances in Immunology*, Chapter 5, 2008, vol. 98, pp. 151-224.

Kim S.J., et al., "Antibody Engineering for the Development of Therapeutic Antibodies," *Mol. Cells*, 2005, vol. 20 (1), pp. 17-29.

Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.

Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.

Lonberg N., et al., "Human Antibodies from Transgenic Mice," *Intern. Rev. Immunol.*, 1995, vol. 13, pp. 65-93.

Lonberg N., "Human Monoclonal Antibodies from Transgenic Mice," *Therapeutic Antibodies. Handbook of Experimental Pharmacology*, 2008, pp. 69-97.

Mårtensson I.L., et al., "The pre-B-cell receptor," *Current Opinion in Immunology*, 2007, vol. 19, pp. 137-142.

O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.

O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.

O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.

Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.

Prak E.T.L., et al., "B cell receptor editing in tolerance and autoimmunity," *Annals of the New York Academy of Sciences*, Jan. 2011, vol. 1217, pp. 96-121.

Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.

Ren L., et al., "Silencing of the immunoglobulin heavy chain locus by removal of all eight constant-region genes in a 200-kb region," *Genomics*, Aug. 2004, vol. 84, pp. 686-695.

Ricker M., European Patent Attorney, Opposition against EP2758535 in the name of Kymab Limited Statement of Facts and Arguments pertaining to Application No. 12772122.3, dated Aug. 9, 2017, 42 pages.

Rudolf M.P., et al., "Molecular basis for nonanaphylactogenicity of a monoclonal anti-IgE antibody," *Journal of Immunology*, Jul. 2010, vol. 165 (2), pp. 813-819.

(56) References Cited

OTHER PUBLICATIONS

Ruiz M., et al, "The Human Immunoglobulin Heavy Diversity (IGHD) and Joining (IGHJ) Segments," *Experimental and Clinical Immunogenetics*, 1999, vol. 16, pp. 173-184.
Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.
Shore D.E., Attorney for Applicant, Third-Party Pre-Issuance Submission Under 37 CFR Sec. 1.290 in U.S. Appl. No. 15/088,805, filed Nov. 17, 2017, 44 pages.
Siman-Tov D.D., et al., "Differentiation of a passive vaccine and the humoral immune response toward infection: Analysis of phage displayed peptides," *Vaccine*, Jan. 2006, vol. 24, pp. 607-612.
Table S1 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857-11.), 60 pages.
Table S2 (from Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857-1-e16857-11.), 14 pages.
Taylor L.D., et al., "A transgenic mouse that expresses a diversity of human sequence heavy and light chain immunoglobulins," *Nucleic Acids Research*, 1992, vol. 20 (23), pp. 6287-6295.
Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161.
European Patent Office, Opposition against EP2798950 Animal Models and Therapeutic Molecules in the name of Kymab Limited pertaining to Application No. 14170196.1, dated Jan. 18, 2018, 33 pages.
1st International MUGEN Conference on Animal Models for Human Immunological Disease, Sep. 10-13, 2006—Athens Greece (Scientific Programme & Presentations), 4 pages.
Bentham A., JA KEMP, Final Written Submissions for Application No. 12171793.8, dated May 17, 2018, 20 pages.
Brüggemann M., "The Preparation of Human Antibodies from Mice Harbouring Human Immunoglobulin Loci," *Transgenic Animals. Generation and Use*, 1997, Chapter 58, Part IV, Section A, pp. 397-402 (including cover and copyright pages).
Calame K., et al., "Regulation of immunoglobulin gene transcription," *Immunoglobulin Genes*, $2^{nd}$ edition, Chapter 18, 1995, pp. 397-422.
European Patent Office, Examination Report for Application No. 16151215.7, dated Jan. 23, 2017, 5 pages.
European Patent Office, Extended European Search Report for Application No. 18153171.6, dated Jun. 28, 2018, 15 pages.
Evans M.J., Declaration of Martin J. Evans with appendices, dated Dec. 23, 2016, 99 pages.
Genbank, "*Homo sapiens* DNA, immunoglobulin heavy-chain variable region, complete sequence, 5 of 5," AB019441.1, dated Jun. 18, 2018, 36 pages.
Grund M., European Patent Attorney, Grund Intellectual Property Group, Third-Party Observations according to Article 115 EPC regarding 12171793.8, dated Oct. 10, 2013, 10 pages.
Grund M., European Patent Attorney, Grund Intellectual Property Group, Third-Party Observations according to Article 115 EPC regarding 12171793.8, dated Mar. 17, 2015, 4 pages.
Grund M., European Patent Attorney, Grund Intellectual Property Group, Third-Party Observations according to Article 115 EPC regarding 12171793.8, dated May 22, 2015, 5 pages.
Grund M., European Patent Attorney, Grund Intellectual Property Group, Third-Party Observations according to Article 115 EPC regarding 14781635.9, dated May 18, 2018, 4 pages.
Grund M., European Patent Attorney, Grund Intellectual Property Group, Third-Party Observations according to Article 115 EPC regarding 17174426.1, dated Jun. 27, 2018, 7 pages.
Janeway C.A. et al., "Structure of the Antibody Molecule and the Immunoglobulin Genes," excerpts from *Immunobiology: The Immune System in Health and Disease*, 4th Edition, 1999, 4 pages.
Li Z., et al., "The generation of antibody diversity through somatic hypermutation and class switch recombination," *Genes & Development*, vol. 18, pp. 1-11 (2004).
Lonberg N., et al., "Antigen-specific human antibodies from mice comprising four distinct genetic modifications," *Nature*, Apr. 1994, vol. 368, pp. 856-859.
Macdonald L., Declaration of Lynne E. Macdonald, dated May 16, 2018, including Annex 1, 10 pages.
Meier I.D., et al., "Short DNA sequences inserted for gene targeting can accidentally interfere with off-target gene expression," *The FASEB Journal*, Research Communication, Jun. 2010, vol. 24, pp. 1714-1724.
Missirlis P.I., et al., "A high-throughout screen identifying sequence and promiscuity characteristics of the loxP spacer region in Cre-mediated recombination," *BMC Genomics*, Apr. 2006, vol. 7(73), 13 pages.
Muramatsu M., et al., "Specific Expression of Activation-induced Cytidine Deaminase (AID), a Novel Member of the RNA-editing Deaminase Family in Germinal Center B Cells," 1999, *The Journal of Biological Chemistry*, vol. 274 (26), pp. 18470-18476.
Newcombe C., et al., "Antibody production: Polyclonal-derived biotherapeutics," *Journal of Chromatography B*, 2007 vol. 848, pp. 2-7.
Okada A., et al., "The variable region gene assembly mechanism," *Immunoglobulin Genes*, $20^{nd}$ edition, Chapter 10, 1995, pp. 205-234.
Pinaud E., et al., "The IgH Locus 3' Regulatory Region: Pulling the Strings from Behind," *Advances in Immunology*, Chapter 2, 2011, vol. 11, pp. 27-70.
Shore D.E., Attorney for Applicant, Third-Party Pre-Issuance Submission Under 37 CFR Sec. 1.290 in U.S. Appl. No. 15/656,897, filed May 4, 2018, 55 pages.
Shore D.E., Attorney for Applicant, Third-Party Pre-Issuance Submission Under 37 CFR Sec. 1.290 in U.S. Appl. No. 15/690,183, filed Feb. 28, 2018, 60 pages.
Shore D.E., Attorney for Applicant, Third-Party Pre-Issuance Submission Under 37 CFR Sec. 1.290 in U.S. Appl. No. 15/786,281, filed Jun. 27, 2018 (First Submission), 63 pages.
Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.
Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.
Stephen R., Olswang LLP, Response to Third-Party Observations for Application No. 12171793.8, as filed with the European Patent Office dated Apr. 17, 2015, 3 pages.
Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.
Stephen R., Olswang LLP, Response to Summons and Preliminary Opinion pertaining to Patent No. EP2517557 for Application No. 12171793.8, as filed with the European Patent Office on May 17, 2018, 4 pages.
Stephen R., Olswang LLP, Response to Opposition in the name of Kymab Limited filed against EP2758535B1, dated Mar. 22, 2018, 26 pages.
U.S. Appl. No. 13/310,431, filed Dec. 1, 2011.
U.S. Appl. No. 13/434,361, filed Mar. 29, 2012, issued Feb 9, 2016 as U.S. Pat. No. 6,253,965.
U.S. Appl. No. 14/137,902, filed Dec. 20, 2013, issued Sep. 6, 216 as U.S. Pat. No. 9,434,782.
U.S. Appl. No. 14/226,698, filed Mar. 26, 2014, issued May 8, 2018 as U.S. Pat. No. 9,963,716.
U.S. Appl. No. 15/018,670, filed Feb. 8, 2016, issued Mar. 27, 2018 as U.S. Pat. No. 9,924,705.
U.S. Appl. No. 15/095,315, filed Apr. 11, 2016, issued Feb. 20, 2018 as. U.S. Pat. No. 9,896,516.

(56) References Cited

OTHER PUBLICATIONS

U.S. Appl. No. 15/383,196, filed Dec. 19, 2016, issued Apr. 10, 2018 as U.S. Pat. No. 9,938,357.
U.S. Appl. No. 15/383,202, filed Dec. 19, 2016, issued Apr. 10, 2018 as U.S. Pat. No. 9,938,358.
U.S. App. No. 15/383,353, filed Dec. 19, 2016.
U.S. Appl. No. 15/948,709, filed Apr. 9, 2018.
U.S. Appl. No. 15/955,216, filed Apr. 17, 2018.
U.S. Appl. No. 15/973,376, filed May 7, 2018.
Goding J.W., "Differences Between Conventional and Monoclonal Serology,"*Monoclonal Antibodies: Principles and Practice, Production and Application of Monoclonal Antibodies in Cell Biology, Biochemistry and Immunology*,1996, Third Edition, Section 7.3, pp. 129-130.
Kelley S.K., et al., "Preclinical pharmacokinetics, pharmacodynamics, and activity of a humanized anti-CD40 antibody (SGN-40) in rodents and non-human primates," *British Journal of Pharmacology*, 2006, vol. 148, pp. 1116-1123.
Kumar R., et al., "A novel strategy for efficient production of anti-V3 human scFvs against HIV-1 clade C," *BMC Biotechnology*, 2012, vol. 12, 15 pages.
U.S. Appl. No. 09/552,219, filed Apr. 19, 2000, issued May 28, 2002 as U.S. Pat. No. 6,395,487.
U.S. Appl. No. 09/552,626, filed Apr. 19, 2000, issued Oct. 8, 2002 as U.S. Pat. No. 6,461,818.
U.S. Appl. No. 13/310,431, filed Dec. 2, 2011.
U.S. Appl. No. 13/416,684, filed Mar. 9, 2012, issued Sep. 20, 2016 as U.S. Pat. No. 9,447,177.
U.S. Appl. No. 13/433,084, filed Mar. 28, 2012, issued Sep. 20, 2016 as U.S. Pat. No. 9,445,581.
U.S. Appl. No. 13/434,361, filed Mar. 29, 2012, issued Feb. 9, 2016 as U.S. Pat. No. 9,253,965.
U.S. Appl. No. 13/740,727, filed Jan. 14, 2013, issued Nov. 29, 2016 as U.S. Pat. No. 9,505,827.
U.S. Appl. No. 13/846,672, filed Mar. 18, 2013, issued Oct. 17, 2017 as U.S. Pat. No. 9,788,534.
U.S. Appl. No. 13/875,892, filed May 2, 2013, issued Oct. 10, 2017 as U.S. Pat. No. 9,783,593.
U.S. Appl. No. 13/886,511, filed May 3, 2013.
U.S. Appl. No. 14/040,405, filed Sep. 27, 2013.
U.S. Appl. No. 14/040,427, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013, issued Sep. 6, 2016 as U.S. Pat. No. 9,434,782.
U.S. Appl. No. 14/220,074, filed Mar. 19, 2014.
U.S. Appl. No. 14/220,080, filed Mar. 19, 2014.
U.S. Appl. No. 14/220,095, filed Mar. 19, 2014, issued Oct. 10, 2017 as U.S. Pat. No. 9,783,618.
U.S. Appl. No. 14/220,099, filed Mar. 19, 2014.
U.S. Appl. No. 14/226,698, filed Mar. 26, 2014.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/497,054, filed Sep. 25, 2014.
U.S. Appl. No. 14/516,461, filed Oct. 16, 2014.
U.S. Appl. No. 14/543,359, filed Nov. 17, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015, issued Nov. 29, 2016 as U.S. Pat. No. 9,504,236.
U.S. Appl. No. 15/016,211, filed Feb. 4, 2016.
U.S. Appl. No. 15/018,670, filed Feb. 8, 2016.
U.S. Appl. No. 15/088,805, filed Apr. 1, 2016.
U.S. Appl. No. 15/095,315, filed Apr. 11, 2016.
U.S. Appl. No. 15/199,575, filed Jun. 30, 2016.
U.S. Appl. No. 15/214,963, filed Jul. 20, 2016.
U.S. Appl. No. 15/232,122, filed Aug. 9, 2016.
U.S. Appl. No. 15/251,969, filed Aug. 30, 2016.
U.S. Appl. No. 15/360,502, filed Nov. 23, 2016.
U.S. Appl. No. 15/369,595, filed Dec. 5, 2016.
U.S. Appl. No. 15/383,101, filed Dec. 19, 2016.
U.S. Appl. No. 15/383,188, filed Dec. 19, 2016.
U.S. Appl. No. 15/383,196, filed Dec. 19, 2016.
U.S. Appl. No. 15/383,202, filed Dec. 19, 2016.
U.S. Appl. No. 15/383,342, filed Dec. 19, 2016.
U.S. Appl. No. 15/383,353, filed Dec. 19, 2016.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017.
U.S. Appl. No. 15/690,183, filed Aug. 29, 2017.
U.S. Appl. No. 15/786,281, filed Oct. 17, 2017.
Bransteitter et al., Activation-Induced Cytidine Deaminase Deaminates Deoxycytidine on Single-Stranded DNA but Requires the Action of RNase, PNAS USA 100(7): 4102-4107, 2003.†
Sekiguchi et al., The Mechanism of V(D)J Recombination, in Honjo, Alt, and Neuberger (eds.), Molecular Biology of B Cells (pp. 61-82), London, UK: Elsevier Academic Press (2004).†
Murphy, A., VelocImmune: Immunoglobulin Variable Region Humanized Mice, In M. Little (ed.) Recombinant Antibodies for Immunotherapy (pp. 100-107), New York, NY: Cambridge University Press (2009).†
Murphy et al., Mice with Megabase Humanization of Their Immunoglobulin Genes Generate Antibodies as Efficiently as Normal Mice, PNAS USA 111(14): 5153-5158, 2014.†

\* cited by examiner
† cited by third party

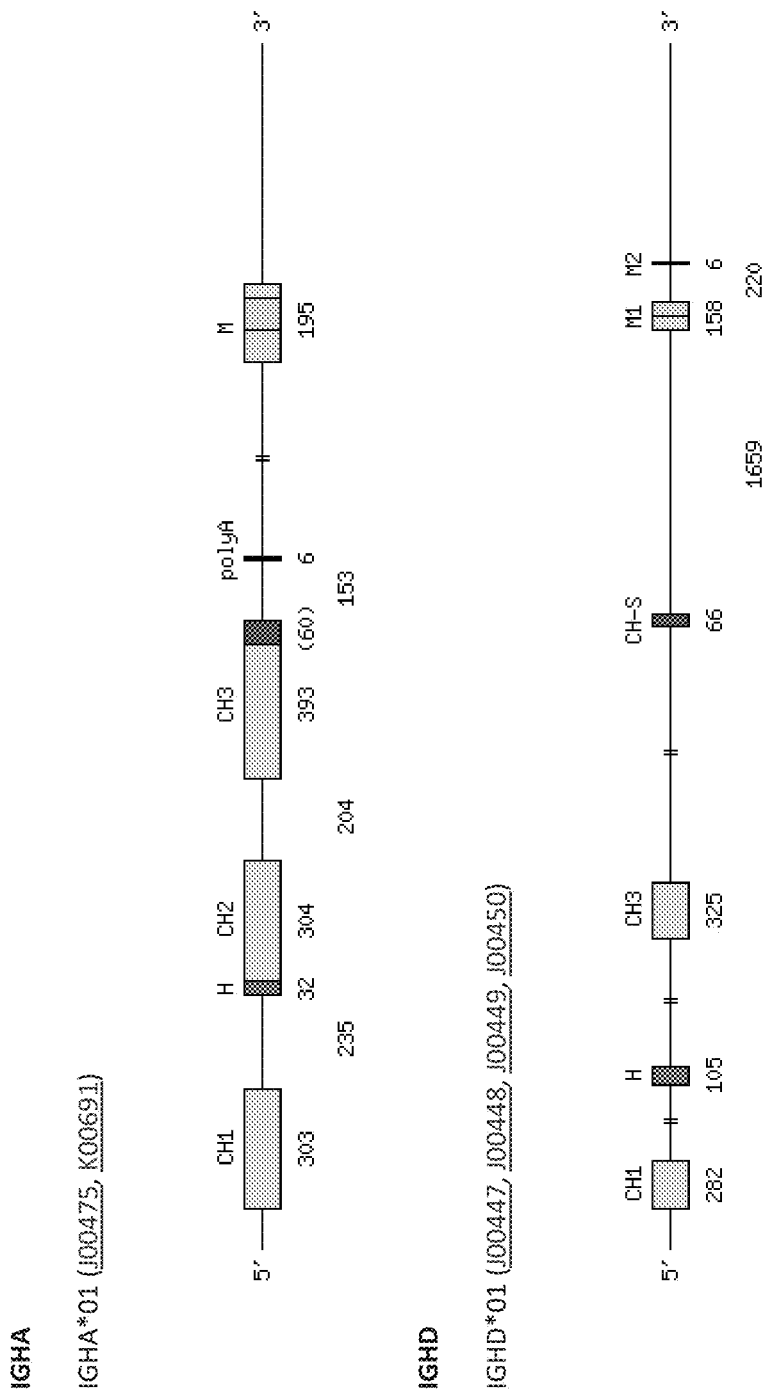
Figure 2A: Gene exon/intron organization: Mouse (Mus musculus) immunoglobulin constant genes IGHC

IGHE
IGHE*01 (X01857, X03624)

IGHG1
IGHG1*01 (J00453, J00454, J00455) (D78344)(1)

IGHG2A
IGHG2A*01 (V00825, J00471) (D78344)(1)

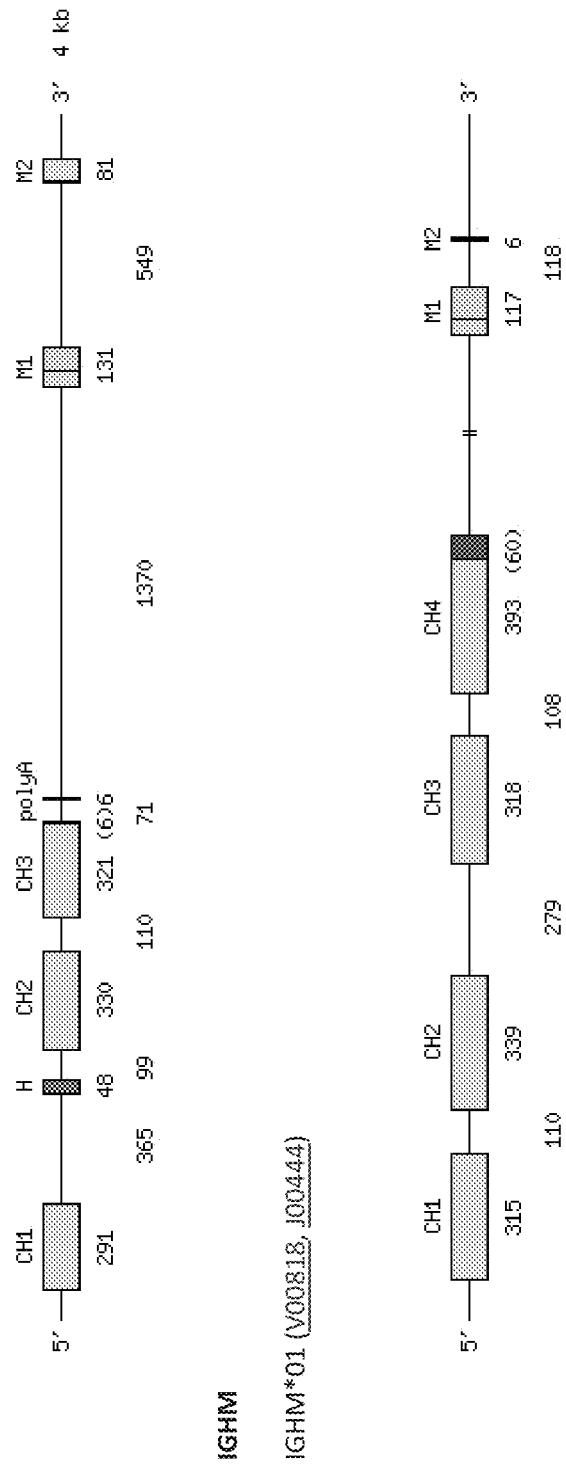

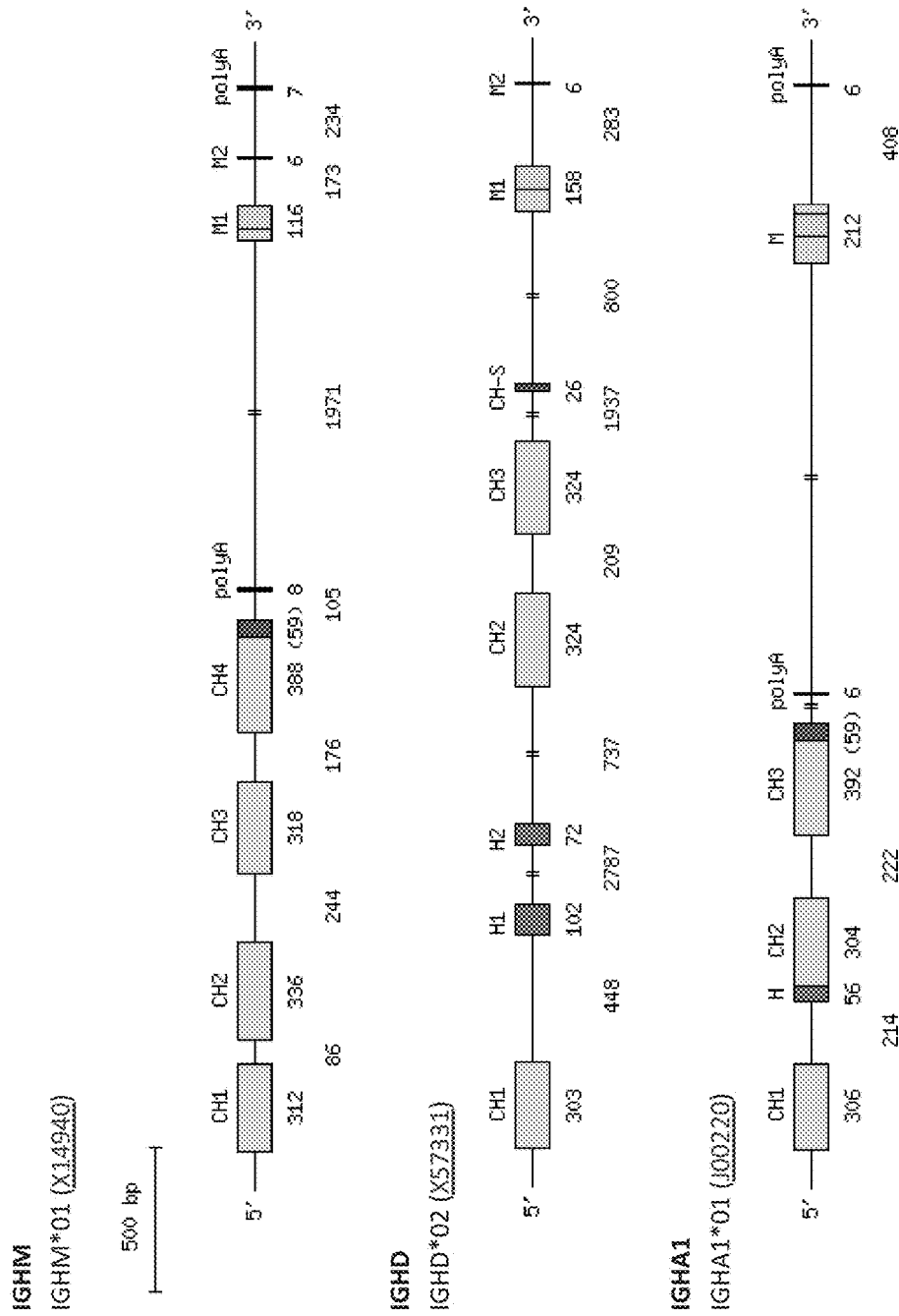

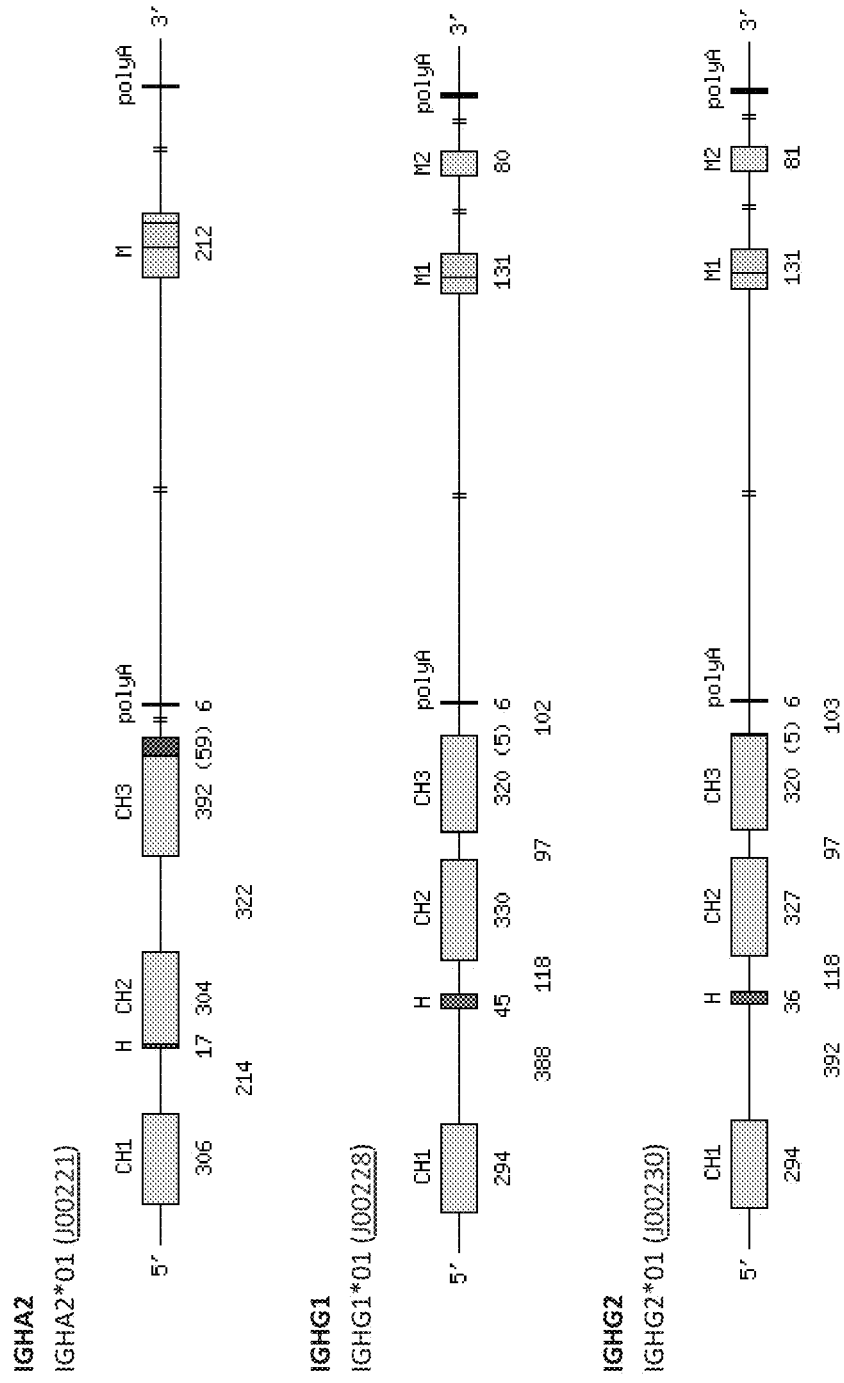

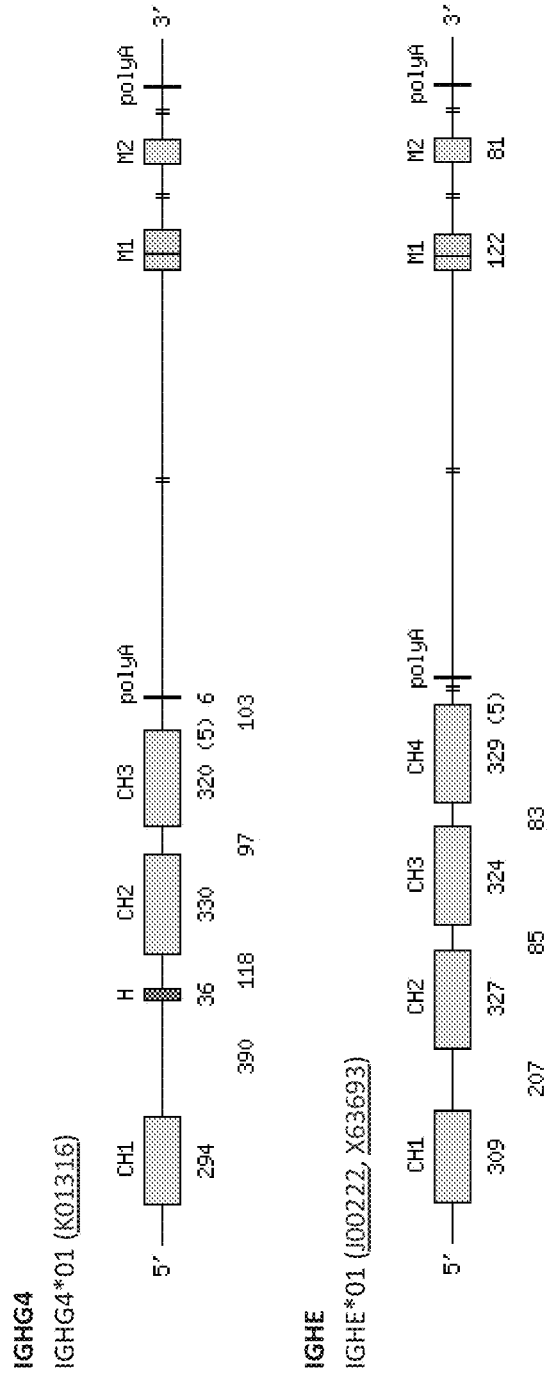

TRANSGENIC NON-HUMAN VERTEBRATE FOR THE EXPRESSION OF CLASS-SWITCHED, FULLY HUMAN, ANTIBODIES

CROSS REFERENCE

This application is a Continuation application of PCT/GB2013/050683 filed Mar. 18, 2013, which claims priority to U.S. application Ser. No. 13/433,084 filed Mar. 28, 2012, U.S. application Ser. No. 13/434,361 filed Mar. 29, 2012, GB Application No. 1207814.3 filed May 4, 2012, GB Application No. 1208708.6 filed May 17, 2012 and GB Application No. 1216795.3 filed Sep. 20, 2012, the contents of all of which are herein incorporated by reference in their entirety.

HUMANISATION OF AFFINITY MATURED ANTIBODIES & HEAVY CHAINS IN VIVO

The present invention relates to the humanisation of antibodies and heavy chains in a way that produces useful human heavy chain repertoires by harnessing endogenous control of junctional mutation and affinity maturation in the context of desired constant regions in vivo in non-human vertebrate systems. To this end, the invention provides non-human vertebrates, cells, populations and methods useful for humanising chimaeric antibodies and heavy chains in vivo. Using the present invention it is possible straightforwardly and rapidly to obtain antigen-specific antibodies and heavy chains that are fully human (ie, comprising human variable and constant regions) and have undergone junctional mutation and affinity maturation in vivo by harnessing a mouse or other non-human vertebrate system. Furthermore, such antibodies and heavy chains are humanised—and selected—totally in vivo, and as such the present invention harnesses in vivo filtering for expressibility (and provides possibly for aspects of affinity and biophysical characteristics to be factored into in vivo selection) in the context of the desired human variable and constant region pairings. This is avoids problems of down-grading antibody characteristics when humanising the constant region of chimaeric antibodies and heavy chains in vitro. Thus, the present invention allows the skilled person to select antibodies and heavy chains directly in the format that they will be used for subsequent human therapeutic and prophylactic use.

BACKGROUND

The state of the art provides methods for producing antibodies in vitro (eg, using phage, ribosome or yeast display) or in vivo (eg, using non-human vertebrates (eg, mice and rats) and cells comprising transgenic immunoglobulin loci). Such in vivo systems (eg, Xenomouse™) have used completely human transgenic heavy chain loci which comprise human variable regions (human VH, D and JH gene segments) upstream of human constant regions (eg, human mu upstream of human gamma constant gene segments). Subsequently, it has been discovered that the use of totally human transgenic loci in such in vivo systems is detrimental and B-cell development is hampered, leading to relatively small B-cell compartments and restricted utility for generating antibodies. Later-generation transgenic animals (eg, the Velocimouse™) have been created which have chimaeric heavy chain loci in which a human variable region is upstream of endogenous (eg, mouse or rat) constant regions (ie, mouse mu constant region upstream of gamma constant region, in germline configuration). This enables the harnessing of endogenous control mechanisms for B-cell and antibody development, and as such the extent of problems of totally human transgenic loci are not seen. Methods of constructing transgenic vertebrates and use of these to generate antibodies and nucleic acids thereof following antigen immunisation are known in the art, eg, see U.S. Pat. No. 7,501,552 (Medarex); U.S. Pat. Nos. 5,939,598 & 6,130,364 (Abgenix); WO02066630, WO2011163311 & WO2011163314 (Regeneron); WO2011004192 & WO2011158009 (Kymab Limited); WO2009076464, WO2009143472, EP1414858, WO2009013620A2, WO2010070263A1 & WO2010109165A2 (Harbour Antibodies); EP1399559 (Crescendo Biologics) and WO2010039900 (Ablexis), the disclosures of which are explicitly incorporated herein including, but not limited to, for the purpose of providing the skilled person with guidance of how to make non-human animals bearing transgenic immunoglobulin loci and to inactivate endogenous loci expression. US2008/0196112A1 (Innate Pharma) discloses transgenic animals comprising a single, predetermined human rearranged VDJ from a lead antibody, together with one or more human constant region genes in a locus. There are no repertoires of unrearranged V, D and J and recombination and junctional diversity to produce a repertoire of VH domains and H chains and antibodies is not addressed.

Whether selected and produced in vitro or in vivo, the art has recognised that the human therapeutic utility of chimaeric antibodies is hampered by their non-human constant domains, despite having human variable domains. This is due to the immunogenicity of the non-human portions once the antibodies have been administered to human patients. The solution in the art to this issue has been to humanise chimaeric antibodies in vitro using protein engineering whereby the non-human constant domains are replaced with corresponding human constant domains. While addressing the immunogenicity issue, however, such engineering in vitro can downgrade the desirable characteristics of the resultant antibody. For example, antigen-binding affinity, antigen specificity, expressibility (eg, in cell lines such as CHO or HEK293 cells), half-life and/or biophysical characteristics (eg, melting temperature, solution state, resistance to aggregation etc) can be downgraded, thereby hampering development of the antibody as drugs for human therapeutic or prophylactic use. It would be desirable to have means for selecting and humanising antibodies that addresses these shortcomings in the art as well as providing repertoires of such humanised antibodies or heavy chains from which drug candidates can be selected.

SUMMARY OF THE INVENTION

The present invention provides a solution by providing for the recombination, humanisation and selection of antibodies entirely in vivo by harnessing the control mechanisms of non-human vertebrate systems. To this end, the invention provides non-human vertebrates, cells, populations and methods useful for humanising chimaeric antibodies to produce fully human antibodies that have undergone variable region gene segment recombination, junctional mutation, somatic hypermutation and isotype switching in vivo and that are selected by an in vivo system. Using the present invention it is possible straightforwardly and rapidly to obtain antigen-specific antibodies that are fully human (ie, comprising human variable and constant regions) and have undergone recombination, affinity maturation in vivo. Furthermore, such antibodies are humanised—and selected—totally in vivo, and as such the present invention harnesses in vivo filtering for expressibility (and affinity and biophysical characteristics factors) in the context of the desired human variable and constant region pairings. This is avoids problems of down-grading antibody characteristics when humanising the constant region of chimaeric antibodies in vitro.

Importantly, the present invention does this in a way that harnesses endogenous control of B-cell development and antibody production and selection. The invention achieves this by ensuring that these functions are carried out in situ in a non-human vertebrate system in an endogenous IgH locus where heavy chain development and selection passes through an IgM stage that is matched with the non-human vertebrate system. Thus, the invention adapts an endogenous IgH locus by targeted insertion of unrearranged human variable region gene segments therein in functional relationship upstream of an endogenous mu constant region (ie, the endogenous Cmu or an inserted exogenous Cmu of the same species of non-human vertebrate). Thus, endogenous control of recombination and IgM heavy chain development and selection can be harnessed to provide a useful pool of properly developed B-cells expressing chimaeric human V/endogenous Cmu heavy chains. Provision of such a good repertoire of cell-surface expressed IgM heavy chains is advantageous since it provides the non-human system with a useful and diverse repertoire from which to select and clonally mature B-cells for subsequent isotype switching to a human non-mu constant region. Thus, a useful repertoire of human non-mu (eg, gamma) heavy chains is provided that have undergone rigorous selection by the endogenous non-human system in vivo for antigen binding and expressibility. The skilled person is thus able to select and isolate one or more desired heavy chains (or antibodies comprising a heavy chain) that are specific to a target antigen, knowing that these have been selected in a totally human format for compatibility with in vivo systems. Thus, one or more biophysical characteristics (eg, melting temperature, low aggregatability, expressibility etc as will be known by the skilled person) have already been usefully tuned, thereby making the selected heavy chain or antibody useful for human drug production.

Thus, the invention provides:—

A non-human vertebrate (eg, a rodent, a mouse, a rat or a rabbit) or a non-human vertebrate cell (eg, a rodent cell, a mouse cell, a rat cell or rabbit cell) whose genome comprises a gene locus for expression of antibody heavy chains, the locus comprising
(a) an unrearranged human variable region comprising human variable region gene segments for expression of a repertoire of human variable domains;
(b) an endogenous mu constant region for expression of IgM antibody heavy chains comprising endogenous mu heavy chain constant domains and human variable domains; and
(c) a humanised non-mu constant region downstream of the mu constant region for expression of non-mu antibody heavy chains comprising human non-mu constant domains and human variable domains;

Wherein the unrearranged variable region is provided as a targeted insertion of the human variable region gene segments upstream of the endogenous mu constant region in an endogenous IgH locus such that the variable region gene segments are able to recombine for expression and selection in the context of an endogenous mu constant region.

In alternative embodiments of any configuration or aspect of the invention, the mu constant region is not endogenous, but is of a different non-human vertebrate species (ie, different to the species of vertebrate or cell). For example, the vertebrate or cell is a mouse and the mu constant region is a non-mouse rodent (eg, rat) mu constant region. For example, the vertebrate or cell is a rat and the mu constant region is a non-rat rodent (eg, mouse) mu constant region. By selecting related species, for example, it is possible still for the endogenous control to function in the context of the mu constant region. Thus, in these embodiments, the vertebrate or cell is of a first non-human vertebrate species and the mu constant region is of a second (ie, different) non-human vertebrate species.

In embodiments of any configuration or aspect of the invention, the mu constant region is of the same non-human species as the vertebrate or cell, but is of a different strain (eg, different mouse or rat strain where the vertebrate is a mouse or rat, or the cell is a mouse or rat cell).

The invention also provides embodiments wherein the IgH locus is provide not by targeted insertion, but by insertion of a transgene and random integration into the genome or integration in a location that is not the endogenous wild-type IgH locus. For example, an IgH locus comprising human variable region and human non-mu constant region can be provided in a yeast artificial chromosome (YAC), PAC or other vector known in the art for accommodating large inserts. The vector can be introduced into an ES cell (eg, mouse or rat ES cell) and the IgH locus can integrate into the genome of the cell.

In embodiments of any configuration or aspect of the invention the humanised non-mu constant region is totally human (ie, comprises only human constant domain genes).

Thus, the invention provides:—

A non-human vertebrate (eg, a rodent, a mouse, a rat or a rabbit) or a non-human vertebrate cell (eg, a rodent cell, a mouse cell, a rat cell or rabbit cell) whose genome comprises a gene locus for expression of antibody heavy chains, the locus comprising
(a) an unrearranged human variable region comprising human variable region gene segments for expression of a repertoire of human variable domains;
(b) an endogenous mu constant region for expression of IgM antibody heavy chains comprising endogenous mu heavy chain constant domains and human variable domains; and
(c) a humanised non-mu constant region downstream of the mu constant region for expression of non-mu antibody heavy chains comprising human non-mu constant domains and human variable domains;

Wherein the unrearranged variable region is provided upstream of the endogenous mu constant region in the locus such that the variable region gene segments are able to recombine for expression and selection in the context of an endogenous mu constant region.

The invention also provides:—

A non-human vertebrate (eg, a mouse or a rat) or a non-human vertebrate cell (eg, a mouse cell or a rat cell) whose genome comprises a gene locus for expression of antibody heavy chains, the locus comprising
(a) a human variable region comprising human variable region gene segments for expression of human variable domains;
(b) an endogenous mu constant region for expression of IgM antibody heavy chains comprising endogenous mu heavy chain constant domains and human variable domains; and
(c) a humanised non-mu constant region downstream of the mu constant region for expression of non-mu antibody heavy chains comprising human non-mu constant domains and human variable domains.

Also the invention provides a non-human vertebrate (eg, a mouse or a rat) or a non-human vertebrate cell whose genome comprises an antibody heavy chain locus comprising (in 5' to 3' direction) a variable region, a first switch, an endogenous mu constant region, a second switch and a human non-mu (eg, gamma) constant region; wherein the heavy chain locus of each cell is capable of undergoing switching from IgM to the non-mu (eg, IgG) isotype.

By retaining an endogenous IgM stage, the invention retains the ability to harness the endogenous antibody and B-cell development control mechanisms of the non-human vertebrate or cell. This includes the ability to harness endogenous terminal deoxynucleotidyl transferase (TdT) activity and junctional mutation as well as proper B-cell development (including at early stages of development when IgM is expressed) to yield good size B-cell compartments and good size and quality repertoires of recombined VDJ diversity from which to subsequently select and mature isotype-switched heavy chains produced from the gene locus of the invention. Furthermore, this entails switching to a human constant region in resulting antibodies, which is beneficial for producing drugs for human therapeutic use. Thus, for example, a vertebrate of the invention can be immunised with a predetermined therapeutic target antigen (eg, a human, viral or bacterial antigen) and antibodies (eg, human IgG) or heavy chains (eg, human gamma-type heavy chains) can be isolated that (i) have undergone junctional and somatic mutation, and thus affinity maturation in vivo in response to antigen challenge, (ii) are fully human, ie, have human variable and constant domains, and (iii) have been selected by a totally in vivo system for expression and ability to bind antigen. Thus, the invention employs in vivo systems to direct the skilled person to viable human antibodies and heavy chains that can be expressed well in vivo and which are specific for a predetermined antigen. The method is simple and avoids multi-step combinations of in vivo and in vitro production and engineering as per the prior art methods.

Moreover, having undergone affinity maturation in the vertebrate or cell, the selected antibodies have had their antigen binding affinities tuned by nature—rather than by man. Thus, vertebrates and cells of the invention provide good sources for fully human antigen-specific antibodies and heavy chains with therapeutically-amenable affinities without the need to perform laborious in vitro affinity maturation (or risk downgrading desirable characteristics due to in vitro manipulation).

Additionally, the present invention enables the skilled person to design vertebrates and cells to produce fully human antibodies of a specific, desired isotype in a predictable way. For example, the skilled person is able to design the heavy chain loci in a vertebrate of the invention so that all gamma constant region gene segments are human ones. In this way, the skilled person will know that all IgG-type antibodies or heavy chains selected from the vertebrate will be fully human in their H chains and will have been subjected to endogenous antibody development (eg, affinity maturation) and in vivo expression and selection. Going a step further, the skilled person could design a vertebrate in which just the IgG1 isotype gene segments are human. Thus, the skilled person will know from the outset that all IgG1 isotype antibodies will be fully human and matured, expressed and selected in vivo. This is useful for tailoring antibody sub-types, such as IgG1 or IgG4, to particular human therapeutic indications, as explained further below.

Thus, in an embodiment, the gene locus of the invention comprises only human constant regions, with the exception of the endogenous mu constant region. This is useful for producing isotype-switched heavy chains in which the constant regions are predictably always human.

In an embodiment, the gene locus of the invention comprises only human constant region gene segments, with the exception of the constant region gene segments of the endogenous mu constant region. Thus, usefully, the skilled person will reliably know at the outset that all switched heavy chains and antibodies will bear human heavy chain constant domains.

In an embodiment, the gene locus of the invention comprises gamma constant region gene segments and all of the gamma constant region gene segments are human. This is useful for producing isotype-switched gamma heavy chains in which the constant regions are predictably always human.

In an embodiment, the gene locus of the invention comprises gamma constant region gene segments and all of the delta constant region gene segments are human. This is useful for producing isotype-switched delta heavy chains in which the constant regions are predictably always human.

In an embodiment, the gene locus of the invention comprises epsilon constant region gene segments and all of the delta constant region gene segments are human. This is useful for producing isotype-switched epsilon heavy chains in which the constant regions are predictably always human.

In an embodiment, the gene locus of the invention comprises alpha constant region gene segments and all of the delta constant region gene segments are human. This is useful for producing isotype-switched alpha heavy chains in which the constant regions are predictably always human.

The invention also enables the skilled person to tailor other characteristics of antibody constant regions to particular therapeutic or prophylactic uses. For example, one can include variant human non-mu constant region gene segments in the heavy chain locus. Thus, in one embodiment, the variants may encode mutant human Fc regions that are either activated (eg, for cell-killing applications such as oncology or treatment of inflammatory conditions) or inactivated (eg, when activation due to cross-linking of cell-surface antigens by antibody is undesirable, eg, as seen when the target antigen is CD40 or CD40 ligand).

In another configuration, the application recognises the desirability of exploring repertoires of variant human constant domains of antibodies when paired and selected with human variable domains in vivo. Such variants are seen in different populations of humans (eg, encoded by different variants of gamma constant region gene segments as seen in different ethnic human populations). Similarly, this concept can be applied to synthetic variants of human constant domains and corresponding human constant region gene segments (eg, variants that have been mutated in different ways to inactivate Fc, or to activate Fc). To this end, the invention provides:—A population of vertebrates of the invention, wherein the population comprises
(i) a first vertebrate wherein the antibody heavy chain locus comprises one or more first human non-mu gene segment(s) (eg, a human CH1, CH2 or CH3; or an Fc);
(ii) and a second vertebrate the antibody heavy chain locus comprises one or more second human non-mu gene segment(s) (eg, a human CH1, CH2 or CH3; or encoding an Fc); and
wherein the first and second gene segments are the same type of constant region gene segment(s) (eg, both CH1 gene segments or both encoding an Fc) and the second gene segment(s) is a variant of the first gene segment(s).

In an embodiment, the immunoglobulin loci of the vertebrates of the population differ only in the repertoire of said human constant regions or constant region gene segments.

The invention also provides a method of isolating a human antibody, the method comprising immunising a vertebrate or population of vertebrates according to any preceding claim with an antigen and isolating an antibody from said vertebrate or a vertebrate of the population, wherein the isolated antibody specifically binds to the antigen and comprises a fully human heavy chain of said non-mu isotype.

The invention also provides:—

A method of obtaining a humanised and affinity matured antigen-specific antibody heavy chain, the method comprising humanising the heavy chain in vivo in a non-human vertebrate (eg, a mouse or a rat) comprising functional RAG and activation induced cytidine deaminase (AID) by immunising the vertebrate with the antigen and obtaining recombination of VH, D and JH gene segments in vivo, somatic hypermutation and isotype switching in a B-cell of the vertebrate from an endogenous mu isotype to a human non-mu isotype, wherein a repertoire of affinity matured antigen-specific non-mu antibody heavy chains are produced and expressed by the vertebrate, the non-mu constant domains of the heavy chains being human constant domains, the method further comprising isolating one or more of said humanised heavy chains.

By using a non-human vertebrate ES cell (eg, an ES cell disclosed herein) the skilled person will be able to provide for the provision of functional RAG and AID. These will be matched with the endogenous mu for good harnessing of the endogenous control mechanisms.

A method of obtaining a humanised and affinity matured antigen-specific antibody heavy chain, the method comprising humanising the heavy chain in vivo in a non-human vertebrate (eg, a mouse or a rat) comprising a functional activation induced cytidine deaminase (AID) by immunising the vertebrate with the antigen and obtaining somatic hypermutation and isotype switching in a B-cell of the vertebrate from an endogenous mu isotype to a human non-mu isotype, wherein an affinity matured antigen-specific antibody heavy chain is produced and expressed by the vertebrate, the non-mu constant domains of the heavy chain being human constant domains, the method further comprising isolating said humanised heavy chain.

The invention also provides a pharmaceutical composition comprising the isolated antibody heavy chain obtained in the method of the invention or a copy or derivative thereof; optionally wherein the heavy chain, copy or derivative is provided by an antibody that specifically binds the antigen.

The invention also provides a method of treating or preventing a medical condition or disease in a human associated or caused by said antigen, the method comprising administering to the human the antigen-specific antibody or heavy chain obtained in the method described above.

The invention also provides the antigen-specific antibody or heavy chain obtained in the method of the invention for use in the treatment or prophylaxis of a medical condition or disease in a human associated or caused by said antigen.

The invention also provides the use of the antigen-specific antibody or heavy chain obtained in the method of the invention in the manufacture of a medicament for use in the treatment or prophylaxis of a medical condition or disease in a human associated or caused by said antigen.

FIGURES

FIG. 2A-2D is a schematic showing the arrangement of gamma, delta, alpha, mu and epsilon isotype human constant regions as found in genomic heavy chain loci (see IMGT database; www.IMGT.org).

FIG. 3A-3D is a schematic showing the arrangement of gamma, delta, alpha, mu and epsilon isotype mouse constant regions as found in genomic heavy chain loci (see IMGT database; www.IMGT.org).

DETAILED DESCRIPTION OF THE INVENTION

The present invention relates to humanisation of antibodies in vivo. To this end, the invention provides non-human vertebrates, cells, populations and methods useful for humanising chimaeric antibodies in vivo. Using the present invention it is possible straightforwardly and rapidly to obtain antigen-specific antibodies that are fully human (ie, comprising human variable and constant regions) and have undergone affinity maturation in vivo. Furthermore, such antibodies are humanised—and selected—totally in vivo, and as such the present invention harnesses in vivo filtering for expressibility (and factors in affinity and biophysical characteristics) in the context of the desired human variable and constant region pairings. This is avoids problems of down-grading antibody characteristics when humanising the constant region of chimaeric antibodies in vitro.

To this end, the invention provides a non-human vertebrate (eg, a mouse or a rat) or a non-human vertebrate cell (eg, a mouse cell or a rat cell) whose genome comprises a gene locus for expression of antibody heavy chains, the locus comprising (a) a human variable region comprising human variable region gene segments for expression of human variable domains;

(b) an endogenous mu constant region for expression of IgM antibody heavy chains comprising endogenous mu heavy chain constant domains and human variable domains; and (c) a humanised non-mu constant region downstream of the mu constant region for expression of non-mu antibody heavy chains (eg, following immunisation of the vertebrate with target antigen) comprising human non-mu constant domains and human variable domains.

The locus is, in the preferred embodiment, a heavy chain locus of the genome, ie, it is in the germline location of a heavy chain locus of said type of vertebrate or cell. In this example, therefore, the humanised locus of the invention can be constructed by inserting human constant region DNA into the endogenous (ie, non-human vertebrate) heavy chain locus downstream of the endogenous mu constant region. In another embodiment, the locus of the invention is synthetically constructed elsewhere in the genome (ie, not in the endogenous heavy chain locus location) and may be on a different chromosome to that chromosome harbouring the heavy chain locus in a wild-type vertebrate or cell. For example, the locus of the invention is constructed at the Rosa26 locus.

Figure 1:
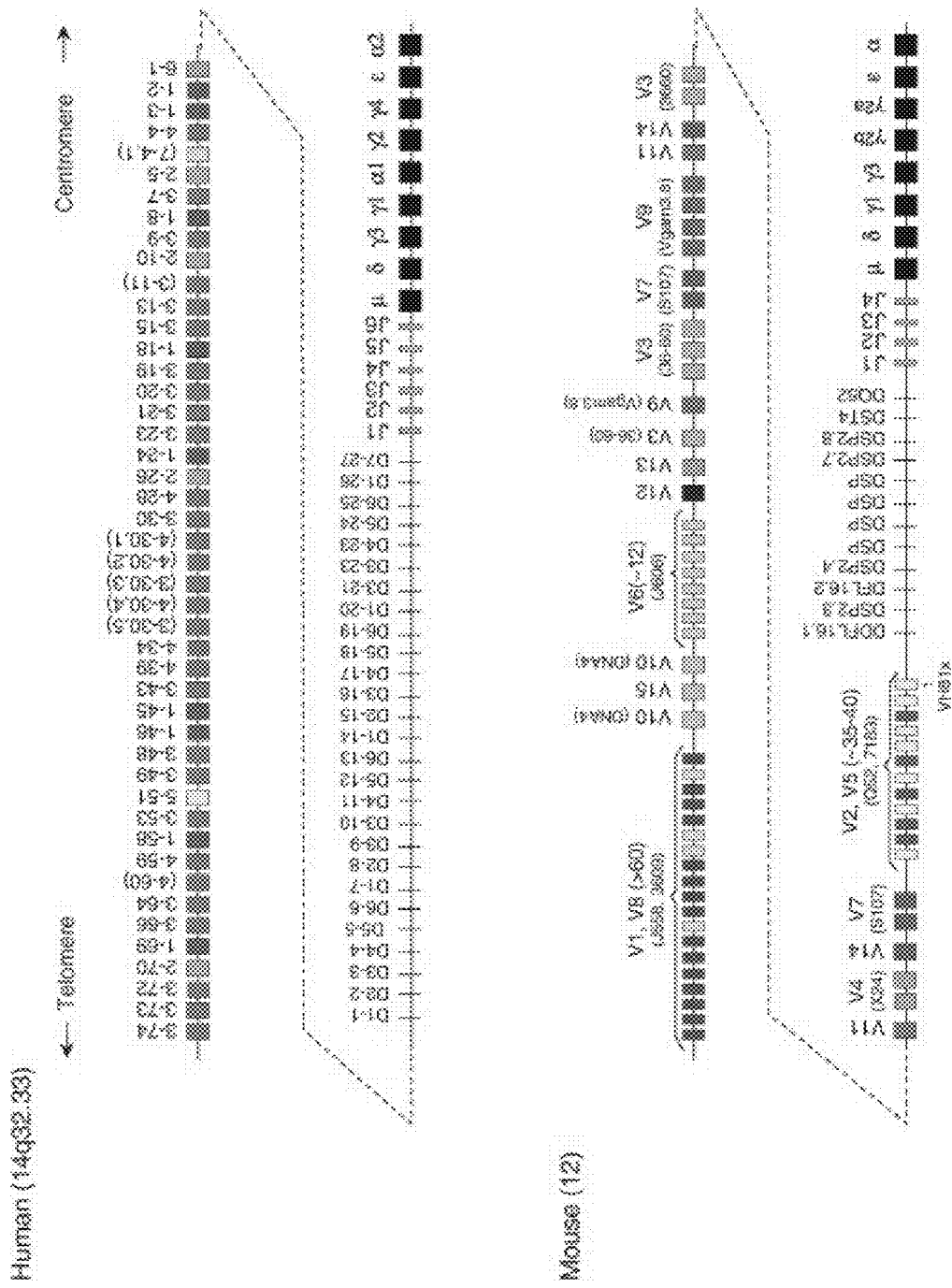
FIG. 1 is a schematic showing the arrangement of the constant regions in wild-type human and mouse genomes (Dev Comp Immunol. 2006; 30(1-2):119-35; Schroeder H W Jr)
Figure 2B:
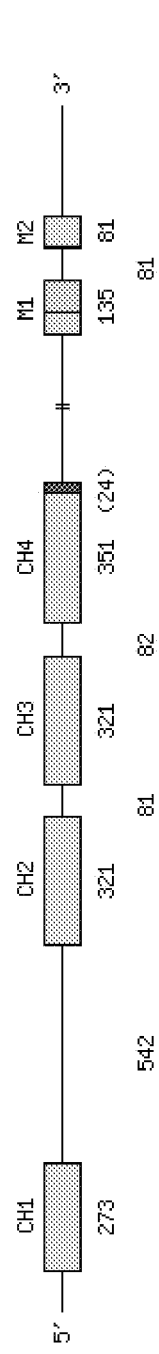
Figure 2B:
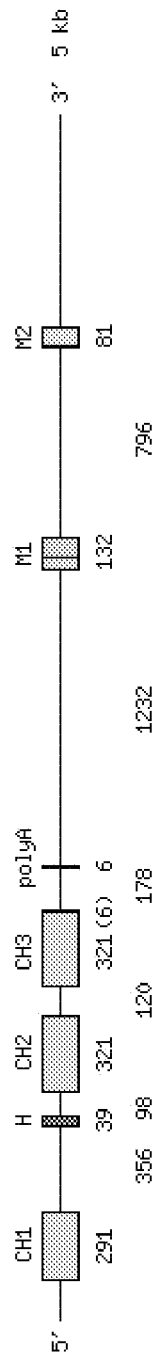
Figure 2C:
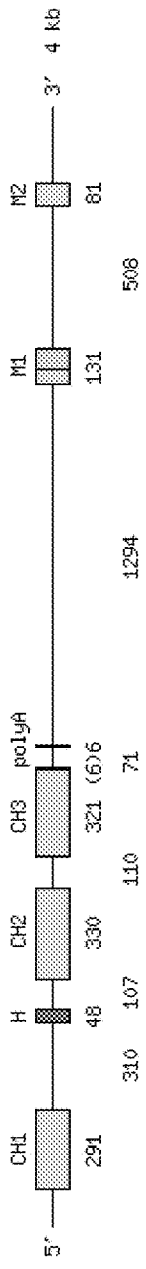
Figure 2C:
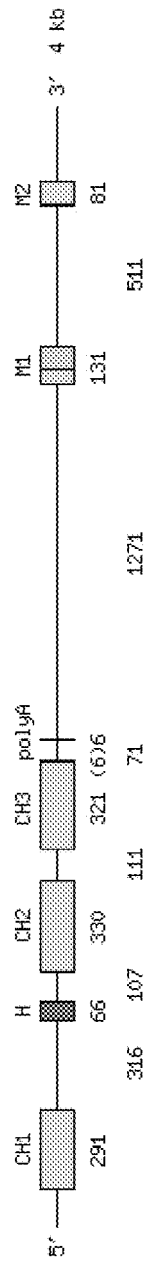
Figure 2C:
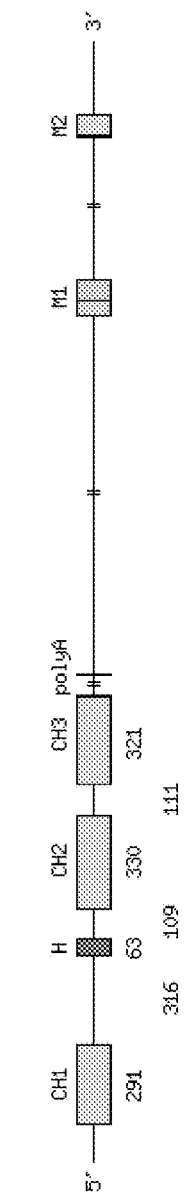
Figure 3C:
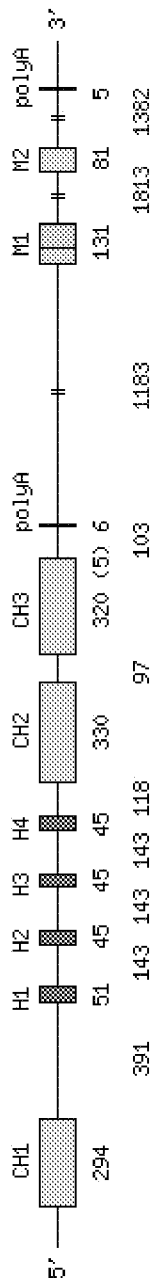
Figure 3C:
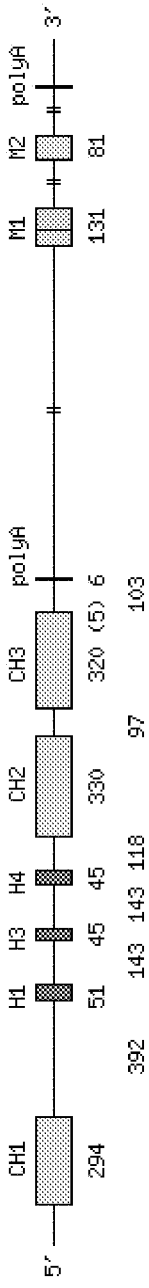
Figure 3C:
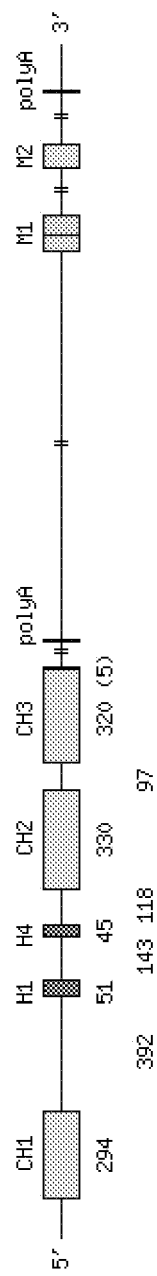

The gene locus of the invention comprises all of the elements required for expression of heavy chains and isotype switching in the vertebrate or cell, such a human variable region comprising a plurality of VH gene segments, a plurality of D gene segments and a plurality of JH gene segments upstream of (ie, 5' of) a S-mu switch (eg, the endogenous S-mu), an endogenous mu constant region comprising endogenous mu constant gene segments (eg, CH1, CH2 and CH3), a second switch (eg, an endogenous switch; eg, a gamma switch) and a (ie, one or more) human non-mu constant region. For example, the human non-mu constant region is a gamma-1 constant region comprising from CH2 to (and including) the poly-A 3' of M2 as shown in FIG. 3. Alternatively, the non-mu constant region is a gamma-1 constant region comprising from CH1 to (and including) the poly-A 3' of M2 as shown in FIG. 3. Alternatively, the non-mu constant region is a gamma-1 constant region comprising from the hinge region (H) to (and including) the poly-A 3' of M2 as shown in FIG. 3. Optionally, the human constant region lacks a CH1 gene segment but includes one or more other human constant gene segments (eg, CH2 and CH3); optionally wherein the constant region is a gamma constant region. This example is useful for producing heavy chain-only antibodies (H2 antibodies) when the vertebrate or cell does not express functional light chains (or expresses no light chains) after isotype switching to the non-mu isotype.

Thus, the following examples of inserted DNA comprising one or more human non-mu constant regions are contemplated:—

Human Gamma Constant Regions
1. A human gamma (eg, gamma-1, gamma-2, gamma-3 or gamma-4) constant region comprising or consisting of the sequence from CH1 to (and including) CH3, M1, M2 or the poly-A immediately 3' of CH3 or M2;
2. A human gamma (eg, gamma-1, gamma-2, gamma-3 or gamma-4) constant region comprising or consisting of the sequence from a hinge to (and including) CH3, M1, M2 or the poly-A immediately 3' of CH3 or M2;
3. A human gamma (eg, gamma-1, gamma-2, gamma-3 or gamma-4) constant region comprising or consisting of the sequence from CH2 to (and including) CH3, M1, M2 or the poly-A immediately 3' of CH3 or M2;
4. A human gamma (eg, gamma-1, gamma-2, gamma-3 or gamma-4) constant region comprising or consisting of the sequence from CH3 to (and including) M1, M2 or the poly-A immediately 3' of CH3 or M2;
5. A human gamma (eg, gamma-1, gamma-2, gamma-3 or gamma-4) constant region excluding a CH1 gene segment;
6. A human gamma (eg, gamma-1, gamma-2, gamma-3 or gamma-4) constant region comprising a CH1 (and optionally also a CH2 and CH3) gene segment;
7. A human gamma (eg, gamma-1, gamma-2, gamma-3 or gamma-4) constant region comprising a CH2 (and optionally also a CH3) gene segment;
8. A human gamma (eg, gamma-1, gamma-2, gamma-3 or gamma-4) constant region comprising a CH3 gene segment;
9. A human gamma (eg, gamma-1, gamma-2, gamma-3 or gamma-4) constant region comprising CH2-CH3 gene segments and excluding a CH1 gene segment;

Human Delta Constant Regions
10. A human delta constant region comprising or consisting of the sequence from CH1 to (and including) CH3, CH-S, M1 or M2;
11. A human delta constant region comprising or consisting of the sequence from hinge H1 or H2 to (and including) CH3, CH-S, M1 or M2;
12. A human delta constant region comprising or consisting of the sequence from CH2 to (and including) CH3, CH-S, M1 or M2;
13. A human delta constant region comprising or consisting of the sequence from CH3 to (and including) CH-S, M1 or M2;
14. A human delta constant region excluding a CH1 gene segment;
15. A human delta constant region comprising a CH1 (and optionally also a CH2 and CH3) gene segment;
16. A human delta constant region comprising a CH2 (and optionally also a CH3) gene segment;
17. A human delta constant region comprising a CH3 gene segment;
18. A human delta constant region comprising CH2-CH3 gene segments and excluding a CH1 gene segment;

Human Alpha Constant Regions
19. A human alpha constant region comprising or consisting of the sequence from CH1 to (and including) CH3, M or the poly-A immediately 3' of M or CH3;
20. A human alpha constant region comprising or consisting of the sequence from hinge (H) to (and including) CH3, M or the poly-A immediately 3' of M or CH3;
21. A human alpha constant region comprising or consisting of the sequence from CH2 to (and including) CH3, M or the poly-A immediately 3' of M or CH3;
22. A human alpha constant region comprising or consisting of the sequence from CH3 to (and including) M or the poly-A immediately 3' of M or CH3;
23. A human alpha constant region excluding a CH1 gene segment;
24. A human alpha constant region comprising a CH1 (and optionally also a CH2 and CH3) gene segment;
25. A human alpha constant region comprising a CH2 (and optionally also a CH3) gene segment;
26. A human alpha constant region comprising a CH3 gene segment;
27. A human alpha constant region comprising CH2-CH3 gene segments and excluding a CH1 gene segment;

The alpha constant region is, in one example, a human alpha-1 constant region. In another example the constant region is a human alpha-2 constant region.

Human Epsilon Constant Regions
28. A human epsilon constant region comprising or consisting of the sequence from CH1 to (and including) CH3, CH4, M or the poly-A immediately 3' of M or CH4;
29. A human epsilon constant region comprising or consisting of the sequence from hinge (H) to (and including) CH3, CH4, M or the poly-A immediately 3' of M or CH4;
30. A human epsilon constant region comprising or consisting of the sequence from CH2 to (and including) CH3, CH4, M or the poly-A immediately 3' of M or CH4;
31. A human epsilon constant region comprising or consisting of the sequence from CH3 to (and including) CH4, M or the poly-A immediately 3' of M or CH4;
32. A human epsilon constant region comprising or consisting of the sequence from CH4 to (and including) M or the poly-A immediately 3' of M or CH4;
33. A human epsilon constant region excluding a CH1 gene segment;
34. A human epsilon constant region comprising a CH1 (and optionally also a CH2, CH3 and CH4) gene segment;

35. A human epsilon constant region comprising a CH2 (and optionally also a CH3 and CH4) gene segment;
36. A human epsilon constant region comprising a CH3 (and optionally also a CH4) gene segment;
37. A human epsilon constant region comprising a CH4 gene segment;
38. A human epsilon constant region comprising CH2-CH3-CH4 gene segments and excluding a CH1 gene segment.

Multiple Isotype Constant Regions
39. A nucleotide sequence comprising or consisting of the sequence from human gamma-3 to (and including) human gamma-4 constant regions;
40. A nucleotide sequence comprising or consisting of the sequence from human gamma-3 to (and including) human gamma-2 constant regions;
41. A nucleotide sequence comprising or consisting of the sequence from human gamma-3 to (and including) human gamma-1 constant regions;
42. A nucleotide sequence comprising or consisting of the sequence from human gamma-1 to (and including) human gamma-4 constant regions;
43. A nucleotide sequence comprising or consisting of the sequence from human gamma-1 to (and including) human gamma-2 constant regions;
44. A nucleotide sequence comprising or consisting of the sequence from human gamma-2 to (and including) human gamma-4 constant regions;
45. A nucleotide sequence comprising or consisting of the sequence from human delta to (and including) human alpha-2 constant regions;
46. A nucleotide sequence comprising or consisting of the sequence from human delta to (and including) human epsilon regions;
47. A nucleotide sequence comprising or consisting of the sequence from human delta to (and including) human gamma-4 constant regions;
48. A nucleotide sequence comprising or consisting of the sequence from human delta to (and including) human gamma-2 constant regions;
49. A nucleotide sequence comprising or consisting of the sequence from human delta to (and including) human alpha-1 constant regions;
50. A nucleotide sequence comprising or consisting of the sequence from human delta to (and including) human gamma-1 constant regions;
51. A nucleotide sequence comprising or consisting of the sequence from human delta to (and including) human gamma-3 constant regions.

Stretches of human DNA can be inserted in one piece or in serial insertions into the genome of a non-human vertebrate or cell (eg, ES cell) genome. For example, a plurality of bacterial artificial chromosomes (BACs) can be constructed using standard recombineering techniques which between them comprise the entire sequence of human constant region DNA to be inserted, each BAC containing a portion of that stretch of DNA. By using serial insertions from serial BACs (eg, using standard homologous recombination (eg, see the Regeneron and Ablexis PCTs disclosed herein) or serial recombinase mediated cassette exchange—sRMCE—(eg, see the Kymab Limited PCTs disclosed herein) the skilled person can build up the one or more human constant regions downstream of the endogenous mu constant region in the genome. When an ES cell is manipulated in this way, the ES cell can be used, as is standard, to implant in a donor blastocyst, which is then implanted into a foster mother. With germline transmission and any necessary subsequent breeding and crossing (again as is conventional), the skilled person can arrive at progeny vertebrates and cells bearing the gene locus of the invention in which one or a plurality of human non-mu constant regions are downstream of an endogenous mu constant region. The gene locus may be present in a homozygous state (eg, a gene locus of the invention at each heavy chain allele) or heterozygous state (eg, with the second allele being an inactivated endogenous heavy chain so that only heavy chain expression from the first allele—bearing the gene locus of the invention—provides expression of heavy chains). In an alternative, different gene loci of the invention are provided at the first and second alleles of the heavy chain locus in the genome, so that different combinations of human isotype switched heavy chains can be expressed by the combination of loci.

In an embodiment, the genome also comprises transgenic light chain loci that express human light chains (or in the alternative at least human light chain variable regions) and endogenous light chain expression is substantially inactive; also endogenous heavy chain expression is substantially inactive. This embodiment advantageously provides a genome for predictable expression of only fully human antibodies (or at least fully human heavy chains and fully human light chain variable regions in the alternative) and no endogenous antibody chains, from which pool of antibodies the skilled person can select (eg, after immunisation with target antigen) non-mu type antibodies (eg, gamma type) that have undergone mutation and maturation and selection by the in vivo machinery of the vertebrate or cell.

It is particularly beneficial to use embodiments in which one or more human gamma constant regions are inserted, since gamma-type antibodies are frequently used in humans in immune responses in disease settings and are thus frequently used as drugs for human medicine. Human gamma-1 isotype is particularly useful for this reason, and many human therapeutic antibody drugs have gamma-1 isotype constant domains accordingly.

As discussed further in WO2011066501, human IgG sub-types IgG1, IgG2, gG3 and IgG4 exhibit differential capacity to recruit immune functions, such as antibody-dependent cellular cytotoxicity (ADCC, e.g., IgG1 and IgG3), antibody-dependent cellular phagocytosis (ADCP, e.g., IgG1, IgG2, IgG3 and IgG4), and complement dependent cytotoxicity (CDC, e.g., IgG1, IgG3). Sub-type-specific engagement of such immune functions is based on selectivity for Fc receptors on distinct immune cells and the ability to bind C1q and activate the assembly of a membrane attack complex (MAC). Among the various types, relative affinity for Fcγ receptors (e.g., FcγRI, FcγRIIa/b/c, FcγRIIIa/b) is high for IgG1 and IgG3, however, there is minimal affinity for IgG2 (restricted to the FcγRIIa 131H polymorphism), and IgG4 only has measurable affinity for FcγRI. Using comparative sequence analysis and co-crystal structures, the key contact residues for receptor binding have been mapped to the amino acid residues spanning the lower hinge and CH2 region. Using standard protein engineering techniques, some success in enhancing or reducing the affinity of an antibody preparation for Fc receptors and the C1q component of complement has been achieved.

Among the isotypes, IgG2 is least capable of binding the family of Fc receptors. Using IgG2 as the starting point, efforts have been made to find a mutant with diminished effector functions but which retains FcRn binding, prolonged stability, and low immunogenicity. Improved mutants of this nature may provide improved antibody therapeutics with retained safety. Human IgG1 therapeutic antibodies that bind to cell surface targets are able to engage effector cells that may mediate cell lysis of the target cell by antibody-dependent cellular cytotoxicity (ADCC) or complement dependent cytotoxicity (CDC). These mechanisms occur through interaction of the CH2 region of the antibody Fc domain to FcγR receptors on immune effector cells or with C1q, the first component of the complement cascade. Table 1 shows the activities of different human gamma sub-types. The skilled person may choose accordingly to promote or dampen-down activity depending upon the disease setting in humans of interest. For example, use of an insertion comprising human gamma-1 constant region is desirable when one wishes to isolated totally human heavy chains and antibodies that have relatively high complement activation activity by the classical pathway and FcγR1 recognition in human patients.

TABLE 1

Summary of function correlated with human gamma sub-type
Effector functions of human IgG

|  | IgG1 | IgG2 | IgG3 | IgG4 |
|---|---|---|---|---|
| Complement activation |  |  |  |  |
| Classical pathway | +++ | + | +++ | − |
| Alternative pathway | − | + | − | − |
| Fc receptor recognition |  |  |  |  |
| FcγRI | +++ | − | +++ | ++ |
| FcγRIIa, 131R/R | ++ | − | ++ | − |
| FcγRIIa, 131H/H | + | + | ++ | − |
| FcγRIIb | ++ | − | ++ | + |
| FcγRIII | + | +/− | + | +/− |

See also Mol Immunol. 2003 December; 40(9):585-93; "Differential binding to human FcgammaRIIa and FcgammaRIIb receptors by human IgG wildtype and mutant antibodies"; Armour K L et al, which is incorporated herein by reference.

IgG2 constant regions are well suited to producing antibodies and heavy chains according to the invention for binding to cytokines or soluble targets in humans, since IgG2 is essentially FcγRI,III-silent, FcγRIIa-active and has little Complement activity.

IgG1 constant regions have wide utility for human therapeutics, since IgG1 antibodies and heavy chains are FcγRI, II,III-active and have complement activity. This can be enhanced by using a human gamma-1 constant region that has been activated by engineering as is known in the art.

Thus, in one embodiment of the vertebrate or cell of the invention the human non-mu constant region comprises CH2 or CH2 and CH3 gene segments encode for an activated Fc region. This is useful for, eg, treating or preventing inflammation or a inflammatory disease or condition. This embodiment is also useful where cell killing in the human patient is desirable, eg, for oncology applications.

In one embodiment of the vertebrate or cell of the invention the human non-mu constant region comprises CH2, or CH2 and CH3, gene segments encode for an inactivated Fc region. This is useful for, eg, applications where triggering following cross-linking is undesirable. This may be useful, for example where cross-linking of cell-surface antigens is to be avoided after administration of an antibody produced according to the invention (eg, where the target antigen against which the antibody or heavy chain is raised is a T-cell costimulatory antigen such as CD40 or CD40 ligand).

The choice of constant region and gene segments to include in the human constant region(s) may also take into account the desirability for good binding to human FcRn in the human patient, so that the heavy chain or antibody comprising this is efficiently recycled and a desirable drug half-life is achieved. For this purpose, gamma-type human constant regions are desirable, since IgG antibodies and heavy chains bind efficiently to human FcRn in vivo.

"Antibody-dependent cell-mediated cytotoxicity" or ADCC" refers to a form of cytotoxicity in which secreted Ig bound onto Fc receptors (FcRs) present on certain cytotoxic cells (e.g., Natural Killer (NK) cells, neutrophils, and macrophages) that enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are required for such killing. Lysis of the target cell is extracellular, requires direct cell-to-cell contact, and does not involve complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al, 1985, 19:21 1; Bruggemann et al, 1987, J Exp Med 166: 1351; Wilkinson et al, 2001, J Immunol Methods 258: 183; Patel et al, 1995 J Immunol Methods 184:29 (each of which is incorporated by reference). Alternatively, or additionally, ADCC activity of the antibody of interest may be assessed in vivo, e.g., in an animal model, such as that disclosed in Clynes et al, 1998, PNAS USA 95:652, the contents of which are incorporated by reference in its entirety.

"Complement-directed cytotoxicity" or CDC refers to the form of cytotoxicity in which the complement cascade is activated by the complement component C1q binding to antibody Fc.

The term "Fc" as used herein refer to the protein comprising (in N- to C-terminal direction) an immunoglobulin CH2 and CH3 domain. The CH2 and CH3 domains can form at least a part of the constant region of an antibody or heavy chain.

"Constant region" as used herein when referring to the gene locus of the invention, is a reference to a stretch of DNA sequence comprising gene segments (constant region gene segments) that combine in vivo with recombined VDJ sequence in the locus. The VDJ yield (optionally following hypermutation), together with the constant region gene segments RNA transcripts in the vertebrate or cell from which can be produced antibody heavy chains (eg, following splicing of RNA), each heavy chains comprising an variable domain and one or more constant domains. When "constant region" is used with reference to an antibody or antibody heavy chain, this is referring to the region C-terminal to the variable domain and comprising one or more constant domains.

"Endogenous" as used herein indicates that the constant region etc is a type of constant region etc that is normally found in the vertebrate or cell (as opposed to an exogenous constant region whose sequence is not normally found in such a vertebrate or cell, eg a human sequence). For example, the endogenous constant region can be those encoded by the wild-type genome of the non-human vertebrate or cell. So, in an example wherein the vertebrate is a mouse, the endogenous constant region would be a mouse constant region. Going further, the endogenous regions are, in an example, strain-matched to the vertebrate or cell. So, in one embodiment, the vertebrate or cell is a mouse 129 ES cell, the endogenous constant region would be mouse 129 constant region. In another embodiment, the vertebrate or cell is a JM8 strain mouse or mouse cell, the endogenous constant region would be mouse JM8 constant region. In another embodiment, the vertebrate or cell is a Black 6 mouse or mouse cell, the endogenous constant region would be mouse Black 6 constant region.

In an embodiment, the gene locus in the vertebrate or cell of the invention comprises (in 5' to 3' direction) one or more membrane-encoding exons (M) and a polyA downstream of the non-human human constant region gene segments, wherein the vertebrate is capable of expressing membrane-bound heavy chain or antibody of said non-mu isotype. Additionally or alternatively, the locus comprises a polyA immediately downstream of the last human constant region gene segment. The locus may further comprise a splice site between the latter polyA and the one or more membrane-encoding exons, wherein the vertebrate or cell is capable of expressing both membrane-bound and secreted forms of the non-mu heavy chain or antibody.

In order to obtain switching from the endogenous mu to human non-mu isotypes, the locus comprises a switch 5' of the mu constant region (eg, the endogenous S-mu is retained) and a second switch 5' of the (or each) human non-mu constant region. The second switch can be the human switch usually present with the human constant region (eg, when the human constant region is a gamma-1 constant region, the human gamma-1 switch is retained). Alternatively, the switch can be the corresponding endogenous non-human vertebrate switch, in this example an endogenous S-gamma (eg, S-gamma-1), eg, where a nucleotide sequence corresponding to human DNA from CH1 to the M2 or polyA 3' of M2 of a human gamma constant region is inserted downstream of an endogenous S-gamma in the vertebrate or cell genome. Switch sequences are known in the art, for example, see Nikaido et al, Nature 292: 845-848 (1981) and also WO2011004192, U.S. Pat. Nos. 7,501,552, 6,673,986, 6,130,364, WO2009/076464 and U.S. Pat. No. 6,586,251, eg, SEQ ID NOs: 9-24 disclosed in U.S. Pat. No. 7,501,552. Commercial human and mouse BAC libraries (eg, the RPC-11 and Caltech A, B, C and D libraries) are sources of suitable immunoglobulin locus sequences, eg, sequences of switches or constant regions. Alternatively, human DNA samples can be obtained de novo from consenting donors (eg, using cheek swabs) and DNA sequences obtained from the samples.

In an embodiment, the vertebrate or cell of the invention comprises an antibody heavy chain locus that comprises (in 5' to 3' direction) a rearranged or unrearranged variable region, a first switch (eg, an S-mu switch, eg an endogenous S-mu), an endogenous mu constant region, a second switch (an S-gamma switch; eg, endogenous S-gamma) and a human constant region of said non-mu isotype; wherein the heavy chain locus is capable of undergoing switching from IgM to the non-mu isotype. Thus, for example, this can be provided by inserting one or more human non-mu constant region sequences downstream (3') of an endogenous mu region in the genome of a non-human vertebrate or cell (eg, ES cell). In this way, the human sequences are provided within the location of the endogenous heavy chain locus and expression from the human sequence can be effectively controlled using endogenous antibody and B-cell mechanisms.

By accommodating VH, D and JH recombination and initial expression in the context of an endogenous IgM, heavy chain variable regions are produced and selected in context of non-human (eg, mouse) mu constant regions. This advantageously enables endogenous RAG-1 and RAG-2 to be efficiently employed in a completely endogenous context, as well as harnessing endogenous control, mutation and signalling involved in antibody and B-cell development. The invention subsequently enables switching to a human non-mu C region, which enables one to produce human constant domains in product heavy chains which have been affinity matured by somatic hypermutation effected by endogenous activation induced cytidine deaminase (AID). Those rearranged variable regions that still work well (eg, good expression, affinity, biophysical characteristics) in the context of the human C domains are selected in vivo by the mouse and amplified following immunisation with a predetermined antigen. This retains the advantage of harnessing endogenous antibody and B-cell production and control, together with affinity maturation and in vivo amplification of selected B-cells expressing desirable antibodies/heavy chains in a way that harnesses the mouse (or other non-vertebrate) system to select for good, fully-human antibodies and heavy chains. This is superior to the prior art method of humanising in vitro, where selection for good biophysical characteristics, expression, affinity etc is not factored in (thus often resulting in a down-grading of these in the prior art) and which adds multi-step procedures following initial production of a chimaeric antibody in vivo.

In one embodiment, the vertebrate or cell of the invention does not express endogenous antibody heavy chains of said non-mu isotype. For example, this is effected using standard methods to delete or inactivate endogenous heavy chain variable and constant regions. Thus, the skilled person will know that heavy chains (and antibodies comprising these) of the predetermined human non-mu isotype (eg, IgG antibodies) produced by the vertebrate or cell will always comprise human constant regions.

In one embodiment, in the vertebrate or cell of the invention the human non-mu constant region is a gamma constant region (eg, gamma-1, -2, 3 or -4). Instead of a gamma constant region, the constant region can be a delta, alpha (eg, alpha-1 or -2) or epsilon constant region. Thus, the invention allows the skilled person to tailor the genome of the vertebrate or cell according to desired constant region functionality of resultant antibodies and heavy chains, as discussed above.

In one embodiment, in the vertebrate or cell of the invention the gamma constant region comprises CH2 and CH3 gene segments for encoding an antibody Fc region. In an example, the constant region also comprises a CH1 gene segment of the human constant region. This is useful for producing heavy chains that are to form part of 4-chain antibodies (classic H2L2 antibodies). In another example, the constant region lacks a CH1 gene segment. This is useful for producing heavy chains that are to form part of heavy-chain only antibodies (H2 antibodies) which are devoid of light chains.

In one embodiment, in the vertebrate or cell of the invention the genome comprises a light chain locus comprising human VL and JL gene segments upstream of a constant region for expression of light chains comprising human variable regions; optionally wherein the constant region is a human light chain constant region. For example, the genome comprises a light chain locus comprising human Vκ and Jκ gene segments upstream of an endogenous or human kappa constant region in the endogenous kappa locus for expression of kappa light chains comprising human variable regions. In this example, where the vertebrate is a mouse, it may not be necessary to humanise the lambda locus, since lambda chain expression in mice is relatively low. Optionally, the lambda locus is inactive and/or comprises human Vλ and Jλ upstream of an endogenous or human lambda constant region. Optionally, endogenous kappa chain expression is inactive.

For example, the vertebrate or cell does not substantially express endogenous light chains.

Inactivation of endogenous antibody, antibody chain or gene segment usage is, for example, substantially complete inactivation or prevention (substantially 100%, ie, essentially none (eg, less than 10, 5, 4, 3, 2, 1 or 0.5%) of the endogenous antibody chain etc (eg, no endogenous heavy chains etc) is expressed). This can be determined, for example, at the antibody chain (protein) level by assessing the antibody repertoire produced by the non-human vertebrate or cell or at the nucleotide level by assessing mRNA transcripts of antibody gene loci, eg, using RACE. In an embodiment, inactivation is more than 50% (ie, 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate is provided by endogenous heavy chains. For example, endogenous heavy chain expression is substantially inactivated such that substantially none of the heavy chain repertoire of the vertebrate is provided by endogenous heavy chains. For example, in an embodiment, endogenous kappa chain expression is substantially inactivated such that no more than 85%, 90%, 95%, 96%, 97%, 98% or 99% of the kappa chain repertoire of the vertebrate is provided by endogenous kappa chains. For example, endogenous kappa chain expression is substantially inactivated such that substantially none of the kappa chain repertoire of the vertebrate is provided by endogenous kappa chains. For example, in an embodiment, endogenous lambda chain expression is substantially inactivated such that no more than 85%, 90%, 95%, 96%, 97%, 98% or 99% of the lambda chain repertoire of the vertebrate is provided by endogenous lambda chains. For example, endogenous lambda chain expression is substantially inactivated such that substantially none of the lambda chain repertoire of the vertebrate is provided by endogenous lambda chains.

In one embodiment, in the vertebrate or cell of the invention the human gamma constant region does not comprise a CH1 gene segment. In this embodiment, in an example, light chain expression is inactive when the non-mu heavy chains are expressed. This is useful for producing heavy-chain only antibodies of the non-mu isotype.

In one embodiment, in the vertebrate or cell of the invention the locus comprises a replacement of endogenous non-mu constant region gene segments (eg, CH2 and CH3 gene segments) with corresponding human constant region gene segments (eg, CH2 and CH3 gene segments) of the same non-mu isotype; optionally wherein an endogenous switch of said non-mu isotype is retained. This may be advantageous for maintaining the non-mu switch control of switching to the accompanying human isotype. Replacement here means functional or physical replacement, wherein the endogenous constant region of said non-mu isotype is non-functional or absent in the final genome and the human constant region is functional and present.

The vertebrate or cell of any preceding claim, wherein the locus comprises an insertion of a human gamma constant region nucleotide sequence comprising sequence from the human gamma S-gamma CH1, hinge or CH2 gene segment to (and including) the human gamma CH3 gene segment, wherein the insertion replaces a corresponding sequence of an endogenous gamma constant region in the genome of the vertebrate or cell. This is advantageous for maintaining the human CH2 and CH3 and inter-gene segment sequences in relative genomic or germline configuration for proper expression of human non-mu Fc in the product heavy chain or antibodies. Proper Fc function is desirable for Fc receptor interactions and recycling in human patients receiving the chain or antibody or a derivative drug thereof, as discussed above. Replacement here means functional or physical replacement, wherein the endogenous constant region of said non-mu isotype is non-functional or absent in the final genome and the human constant region is functional and present.

In an example, the human constant region is in human germline configuration. The term "germline configuration" refers to a germline genomic configuration. For example, human immunoglobulin gene segments present in the gene locus of the invention are in a germline configuration when the relative order of the human gene segments is the same as the order of corresponding gene segments in a human germline genome. For example, when the gene locus of the invention comprises hypothetical human immunoglobulin constant region gene segments A, B and C, these would be provided in this order (5' to 3' in the locus) when the corresponding gene segments of a human germline genome comprises the arrangement 5'-A-B-C-3'; and optionally the inter-gene segments too are in germline configuration (ie, the nucleotide sequence from A to C corresponds to a stretch of contiguous nucleotide sequence from A to C in a human germline genome). Available databases and sources of human germline sequence are discussed below. Thus, in an example, when elements of a human immunoglobulin locus (eg, gene segments, enhancers or other regulatory elements) are provided in a gene locus according to the invention, the human Ig locus elements are in germline configuration when the relative order of the elements is the same as the order of corresponding elements in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C-S3-3', wherein A, B and C are human immunoglobulin gene segments and S1-S3 are human inter-gene segment sequences, wherein the corresponding arrangement 5'-A-S1-B-S2-C-S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT, Kabat and other antibody resources).

In an embodiment of the invention, endogenous inter-gene segment sequences have been retained so that the heavy chain locus comprises said human non-mu constant region gene segments flanked by endogenous constant region inter-gene segment sequences. This is useful for preserving any endogenous, non-human regulatory elements between gene segments—for control using endogenous mechanisms for class switching and antibody/chain production in the vertebrate or cell.

In an embodiment of the invention, the gene locus comprises a replacement of endogenous gamma constant region gene segments (eg, gamma CH2 and CH3 gene segments) with human gamma constant region gene segments (eg, gamma CH2 and CH3 gene segments), but endogenous sequences between gamma constant regions have been retained. This is useful for preserving any endogenous, non-human regulatory elements between gene segments— for control using endogenous mechanisms for class switching and antibody/chain production in the vertebrate or cell.

Populations for Providing Alternative Combinations & In Vivo Selections of Human Constant Regions The invention also provides a general combinatorial or repertoire approach that enables the skilled person to design an antibody/heavy chain production and selection scheme that combines human mutated variable regions with a plurality of different human constant domains (and/or synthetic mutants thereof). This scheme straight-forwardly harnesses the in vivo non-human vertebrate system to perform combinations, affinity maturation, and selection by expression and amplification of target antigen-specific heavy chains that are productive and in a fully human configuration. Thus, the skilled person is provided with a way of obtaining a repertoire of matured, target antigen-specific human heavy chain variable domains paired with a repertoire of human constant regions. The skilled person will know that all members of the repertoire represent productive combinations of human variable and constant heavy chain regions, in that they can be expressed to detectable and selectable levels in an in vivo system. From the repertoire (eg, a repertoire provided in a population of non-human vertebrates of the invention; or a repertoire of B-cells isolated from such vertebrates; or a repertoire of antibodies or heavy chains isolated from such vertebrates or cells; or a repertoire of nucleotide sequences encoding such antibodies or heavy chains) the skilled person is able to select one or more antibodies or heavy chains (or corresponding nucleotides sequences) that bind the target antigen. Selection is performed on the basis of a desired antibody/chain characteristic, such as antigen binding affinity and/or a biophysical characteristic.

To this end, there is provided a population of vertebrates according to the invention, wherein the population comprises (i) a first of said vertebrates wherein said gene locus is an antibody heavy chain locus that comprises one or more first human non-mu gene segment(s) (eg, a human CH1, CH2 or CH3; or an Fc) or a first human non-mu constant region;

(ii) and a second of said vertebrates wherein said gene locus is an antibody heavy chain locus that comprises one or more second human non-mu gene segment(s) (eg, a human CH1, CH2 or CH3; or encoding an Fc) or a second human non-mu constant region; and wherein the first and second gene segments are the same type of constant region gene segment(s) (eg, both CH1 gene segments or both encoding an Fc) and the second gene segment(s) is a variant of (ie, is a mutant of) the first gene segment(s).

Thus, this aspect of the invention is useful, for example, because it enables the skilled person to use the vertebrates to select for desirable human V regions (and those that express and perform well, have good biophysical characteristics etc) in vivo in the context of a repertoire of naturally-occurring human constant region polymorphic variants—thus one can include the most common human variants (eg, as present in the 1000 Genomes database; www.1000genomes.org) to arrive at human antibodies and heavy chains that have wide application in human medicine, or can be selected (according to the C region variant distribution in the human ethnic and other populations) to be tailored to specific human populations. Also variants may have differing expression and/or biophysical characteristics—thus allowing one to have a pool of human antibodies and heavy chains from which to select good drug candidates for human use.

Thus, in an example, the second gene segment(s) is derived from the genome sequence of different human individuals, for example sequences appearing in the 1000 Genomes database (www.1000genomes.org).

The variant can, in one example, have no more than 15, 10, 9, 8, 7, 6, 5, 4, 3, 2 or 1 mutations compared to the corresponding first gene segment(s) or region.

In an embodiment, the second gene segment(s) or region is a synthetic mutant of the first gene segment(s) or region. In one example, the second gene segment(s) or region has no more than 15, 10, 9, 8, 7, 6, 5, 4, 3, 2 or 1 mutations compared to the corresponding first gene segment(s) or region. In this way, the skilled person can test out mutations in vivo in combination with a repertoire of human heavy chain variable regions. Combinations that are not productive will not be expressed and/or proliferate (as regulated by the vertebrates' own in vivo machinery) and productive combinations are then provided in one of said repertoires for selection of one or more desirable antibodies or heavy chains bearing human constant regions. Thus, for example, one can make (eg, design by specific choice of positions to mutate and/or residues to be encoded) mutant variants of a desired type of constant region (eg, to produce a collection of constant region encoding variant gamma, eg, gamma-1, constant regions). The mutants, in one example, are made with the aim of finding Fc inactivating variants that work well with the selected human variable regions. In another example, the mutants are made with the aim of finding Fc activating variants that work well with the selected human variable regions. Inactivation or activation of Fc can be tested (as is known in the art) after one or more antibodies or heavy chains have been selected from the population or repertoire. Advantageously, no further manipulation is required in vitro and expressibility of mutants and combinations is guaranteed in an in vivo system (at least cells of the non-human vertebrate type). For example, by immortalising isolated B-cells expressing to the selected antibodies/ heavy chains (eg, by immortalising the B-cell directly or by fusion with a myeloma cell to produce a hybridoma), one then has a cell line that provides a good source of selected antibodies. Additionally, since in vitro manipulation is not necessary post-selection, the risk of down-grading biophysical characteristics is lowered and one can simply test the biophysical characteristics of a panel of lead antibodies/ heavy chains (that have been selected for antigen binding in the desired affinity range) and select one or more antibodies/ chains from this pane that meet the profile of characteristics required for human medicinal use and drug production and administration methods.

Thus, in an embodiment, one or both of the first and second gene segment(s) or regions encodes an inactivated human gamma Fc.

In an embodiment one or both of the first and second gene segment(s) or regions encodes an activated human gamma Fc.

Thus, the population of the invention provides an overall heavy chain repertoire comprising the heavy chain sequence repertoires of the first and second vertebrates. The vertebrates in the population can be immunised with the same antigen in a method of selecting and isolating one or more heavy chains (eg, provided as part of antibodies) that specifically bind to the antigen.

The VH gene segments of a repertoire can, in one embodiment, be recombed VH, ie, provided as part of a variable region sequence derived from the recombination of human VH with D and JH (eg, where the VH, D and JH are human).

In an embodiment, the population comprises a third said non-human vertebrate, wherein the human constant region gene segment repertoire is different from those of the first and second vertebrates, whereby the third vertebrate can produce a heavy chain sequence repertoire that is different from the heavy chain sequence repertoire produced by the first and second vertebrates. Thus, the population provides an overall heavy chain repertoire comprising the heavy chain sequence repertoires of the first, second and third vertebrates. The vertebrates in the population can be immunised with the same antigen in a method of selecting and isolating one or more heavy chains (eg, provided as part of antibodies) that specifically bind to the antigen.

In an embodiment, VH gene segment repertoire provided by said population comprises a substantially complete repertoire of functional human VH gene segments; optionally providing at least 6 different human JH gene segments, 27 different human D segments and at least 40 different human VH gene segments.

In an embodiment, the VH gene segment repertoire provided by said population comprises at least 20, 25, 30, 35 or 40 different human VH gene segments.

In an embodiment, the method of the invention comprises the step of immunising the vertebrates of the population with the same antigen (eg, a human antigen). Thus, the vertebrates are a population and are used as such.

In an embodiment, immunisation of two, more or all of said vertebrates is separated by no more than 12, 9, 6, 5, 4, 3, 2 or 1 months or 3, 2 or 1 week or 6, 5, 4, 3, 2, or 1 day. Thus, the vertebrates are a population and are used as such.

In an embodiment, the method of the invention comprises the step of selecting one or more heavy chains or antibodies from each of said immunised vertebrates on the basis of a common desired antibody or heavy chain characteristic (eg, binding affinity for said antigen), wherein the selected antibodies comprise human non-mu heavy chains, or the selected heavy chains are human.

In an example, the vertebrates share the same genetic background, with the exception of the heavy chain loci thereof (and optionally one or more of the light chain loci thereof).

In any configuration of the invention, in an embodiment vertebrates are derived from transgenic non-human vertebrate ancestor embryonic stem cells that have been genetically modified to include human immunoglobulin locus DNA, the ancestor stem cells being identical or related (eg, clonally related); optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction). For example, the genomes comprise a common junction within or at the boundary of one or more of their immunoglobulin chain loci (eg, heavy chain loci and/or light chain loci). For example, the vertebrates of the population are mice whose genomes comprise a common human-mouse DNA junction within their heavy chain loci and/or one or more light chain loci. This is indicative that the mice form a population. For example, by producing variant vertebrates all stemming back from a common ancestor, the vertebrates can all share the same genetic background with the exception of one or more human gene segment repertoires in their genomes. This means that, with the exception of the expression profile resulting from the different gene segment sub-repertoires, there are no other introduced genetic variables between the members of the population, which enhances consistency of performance of the members of the population. This also simplifies breeding to produce the variants making up the population.

The invention provides an animal house or a laboratory containing a population according to the invention. For example, vertebrates of the population can be housed in the same cage or in the same collection of cages in the same animal house, building or laboratory. The cages or vertebrates themselves may be labelled so that they are part of the same population or experiment. They may be owned by the same owner, eg, the same company, or in the control of a single person or company. They may be allocated for use in the same research programme or series of related research experiments aimed at discovering one or more antibodies or antibody chains against a common antigen or related antigens. Thus, the vertebrates provide a population and are used as such. It is indicative of a population, that the vertebrates are discussed in the context of the same research programme or immunisation schedule or experiment or set of experiments in a laboratory notebook or a set of laboratory notebooks that relate to the same research programme or immunisation schedule or experiment or set of experiments. For example, such a programme, schedule or experiment(s) may relate to immunisation of the vertebrates of a population with the same antigen.

Methods of In Vivo Humanisation & Antibody/Chain Selection

An aspect provides a method of isolating an antibody, heavy chain or nucleotide sequence encoding said antibody, the method comprising (a) immunising (see e.g. Harlow, E. & Lane, D. 1998, $5^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259) a vertebrate or population according to the invention with an antigen such that the vertebrate(s) produce antibodies; and (b) isolating from immunised vertebrate(s) an antibody or heavy chain that specifically binds to said antigen and/or a nucleotide sequence encoding at least the heavy chain variable region of said antibody.

Suitably an immunogenic amount of the antigen is delivered in the method of the invention. The invention also relates to a method for detecting a target antigen comprising detecting an antibody or heavy chain produced as above or a derivative thereof with a secondary detection agent which recognises a portion of that antibody/chain.

Isolation of the antibody in step (b) can be carried out using conventional antibody selection techniques, eg, panning for antibodies against antigen that has been immobilised on a solid support, optionally with iterative rounds at increasing stringency, as will be readily apparent to the skilled person.

As a further optional step, after step (b) the amino acid sequence of the heavy chain variable region is mutated to improve affinity for binding to said antigen. Mutation can be generated by conventional techniques as will be readily apparent to the skilled person, eg, by error-prone PCR.

Affinity can be determined by conventional techniques as will be readily apparent to the skilled person, eg, by surface plasmon resonance, eg, using Biacore™.

Additionally or alternatively, as a further optional step, after step (b) the amino acid sequence of the heavy chain variable region is mutated to further improve one or more biophysical characteristics of the antibody, eg, one or more of melting temperature, solution state (monomer or dimer), stability and expression (eg, in CHO or *E coli*).

An aspect provides an antibody or heavy chain produced by the method of the invention, optionally for use in human medicine, eg, for treating and/or preventing a medical condition or disease in a human patient.

The invention provides a method of isolating a human antibody, the method comprising immunising a vertebrate or population of vertebrates according to any preceding claim with an antigen (eg, human antigen or viral or bacterial antigen) and isolating an antibody from said vertebrate or a vertebrate of the population, wherein the isolated antibody specifically binds to the antigen and comprises a fully human heavy chain of said non-mu isotype. The invention provides a pharmaceutical composition comprising the isolated antibody or a copy or derivative thereof.

The method provides a method of obtaining a humanised and affinity matured antigen-specific antibody heavy chain, the method comprising humanising the heavy chain in vivo in a non-human vertebrate (eg, a mouse or a rat) comprising a functional activation induced cytidine deaminase (AID) by immunising the vertebrate with the antigen and obtaining somatic hypermutation and isotype switching in a B-cell of the vertebrate from an endogenous mu isotype to a human non-mu isotype, wherein an affinity matured antigen-specific antibody heavy chain is produced and expressed by the vertebrate, the non-mu constant domains of the heavy chain being human constant domains, the method further comprising isolating said humanised heavy chain.

In an example, the variable domain of the heavy chain is a human variable domain.

In an example, the vertebrate is according to any aspect of the invention as described above.

The method provides a pharmaceutical composition comprising the isolated antibody heavy chain obtained in the method or a copy or derivative thereof; optionally wherein the heavy chain, copy or derivative is provided by an antibody that specifically binds the antigen.

Optionally, the method comprises the step of isolating a B-cell from said immunised vertebrate (or an immunised vertebrate of said population), wherein the B-cell expresses said isolated antibody or heavy chain; and optionally immortalising the B-cell.

Optionally, the method comprises the step of isolating a nucleotide sequence from said immunised vertebrate or B-cell, wherein the nucleotide sequence encodes said isolated antibody or a heavy chain thereof.

The method provides a vector (optionally in a host cell) comprising the nucleotide sequence of the invention or a copy thereof, or a derivative thereof; optionally comprising up to 15, 10, 9, 8, 7, 6, 5, 4, 3, or 1 mutations. The derivative specifically binds target antigen.

The method provides a method of treating or preventing a medical condition or disease in a human associated or caused by said antigen, the method comprising administering to the human the antigen-specific antibody or heavy chain obtained in the method.

The method provides the antigen-specific antibody or heavy chain obtained in the method for use in the treatment or prophylaxis of a medical condition or disease in a human associated or caused by said antigen.

The method provides the use of the antigen-specific antibody or heavy chain obtained in the method in the manufacture of a medicament for use in the treatment or prophylaxis of a medical condition or disease in a human associated or caused by said antigen.

As will be readily apparent to the skilled person, the operable connection of a human gene segment (eg, a V or J gene segment) upstream of a constant region in an Ig locus in any configuration of the invention enables the gene segment to be recombined and expressed in an immunoglobulin chain comprising sequence encoded by the constant region of the locus.

The term "antibody" includes monoclonal antibodies (including full length antibodies which have an immunoglobulin Fc region), antibody compositions with polyepitopic specificity, multispecific antibodies (e.g., bispecific antibodies, as well as antibody fragments (e.g., Fab, F(ab')2). The term "antibody" also includes H2 antibodies that comprise a dimer of a heavy chain (5'-VH-(optional Hinge)-CH2-CH3-3') and are devoid of a light chain (akin to naturally-occurring H2 antibodies; see, eg, Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). Thus, in an embodiment of the present invention, RNA produced from the transgenic heavy chain locus of the invention encodes for heavy chains that re devoid of a CH1 gene segment and comprise no functional antibody light chain. In an example, RNA produced from the transgenic heavy chain locus encodes for VH single variable domains (dAbs; domain antibodies) with one or more human constant domains. Antibodies, according to the invention, comprise one or more human constant domains of non-mu isotype.

Examples of antibodies are classic 4-chain antibodies comprising two heavy chains paired with two light chains (such as, a dimer of 5'-VH-CH1-Hinge-CH2-CH3-3' paired with 5'-VL-CL-3') or H2 antibodies that comprise a dimer of a heavy chain (5'-VH-(optional Hinge)-CH2-CH3-3') and are devoid of a light chain Thus, in an embodiment of the present invention, the heavy chain sequence repertoire encodes for heavy chains that re devoid of a CH1 gene segment and comprise no functional antibody light chain. In an example, the heavy chain sequence repertoire encodes a repertoire of VH single variable domains (dAbs; domain antibodies) with one or more human constant domains.

In an example of any configuration of the invention, a repertoire comprises a plurality of different members (thus, for example, a heavy chain repertoire comprises a plurality of different heavy chain sequences, such as sequences differing in their variable regions and/or human non-mu constant regions). In an example of any configuration of the invention, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ members. For example, a repertoire of antibody heavy chains or antibodies comprises or consists of at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ antibody chain sequences or antibodies respectively. For example, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ different members. For example, a repertoire of gene segments comprises or consists of 2, 3, 4, 5, 6, 7, 8, 9, 10, at least 15, at least 20, at least 30, at least 40, at least 50 gene segments. Optionally, all of the gene segments are different from each other; or all of the gene segments of the same type (eg, CH2) are different from each other.

In an example of any configuration of the invention, a population comprises a plurality of different members. Thus, for example, a population of non-human vertebrates (eg, mice or rats) comprises a plurality of vertebrates wherein at least two or more of the vertebrates comprise non-identical genomes. The genomes differ in their respective repertoire of human constant region gene segments. In an example of any configuration of the invention, a population of non-human vertebrates comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$ non-human vertebrates. When the population consists of two vertebrates, the genomes of vertebrates are different.

In one embodiment in any configuration of the invention, each vertebrate is a non-human mammal. In one embodiment in any configuration of the invention, the vertebrate is a mouse, rat, rabbit, Camelid (eg, a llama, alpaca or camel), chicken, lamprey or shark. For example, all vertebrates are of the same vertebrate species, eg, all mice or all rats.

In any configuration of the invention, the human gene regions or segments may be derived from the same individual or different individuals, or be synthetic (synthetically mutated human gene segments) or represent human consensus sequences.

Techniques for constructing non-human vertebrates and vertebrate cells whose genomes comprise a human immunoglobulin gene segments are well known in the art. For example, reference is made to WO2011004192, U.S. Pat. Nos. 7,501,552, 6,673,986, 6,130,364, WO2009076464 and U.S. Pat. No. 6,586,251, the disclosures of which are incorporated herein by reference in their entirety.

In one example, a non-human vertebrate of any configuration of the invention is able to generate a diversity of at least $1 \times 10^6$ different functional non-mu immunoglobulin sequence combinations.

Human variable regions are suitably inserted upstream of a non-human vertebrate mu constant region, the latter together with downstream human constant region(s) comprising all of the DNA required to encode the full constant region or a sufficient portion of the constant region to allow the formation of an effective non-mu antibody/heavy chain capable of specifically recognising a target antigen.

The endogenous mu non-human vertebrate constant region herein is optionally the endogenous host wild-type constant region located at the wild type locus, as appropriate for the heavy chain. For example, the human constant region DNA is suitably inserted on mouse chromosome 12, immediately downstream of the mouse heavy chain mu constant region, where the vertebrate is a mouse.

In one optional aspect where the vertebrate is a mouse, the insertion of human variable region DNA (V, D and J gene segments) is targeted to the region between the J4 exon and the endogenous Sμ locus in the mouse genome IgH locus, and in one aspect is inserted between coordinates 114,667,090 and 114,665,190, suitably at coordinate 114,667,091, after 114,667,090.

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see www.genome.ucsc.edu and http://genome.ucsc.edu/FAQ/FAQreleases.html) unless otherwise specified. Human nucleotides coordinates are those corresponding to GRCh37 (e.g. UCSC version hg 19, http://genome.ucsc.edu/FAQ/FAQreleases.html), February 2009 ENSEMBL Release 55.or are those corresponding to NCBI36, Ensemble release 54 unless otherwise specified. Rat nucleotides are those corresponding to RGSC 3.4 Dec. 2004 ENSEMBL release 55.34w, or Baylor College of Medicine HGSC v3.4 Nov. 2004 (e.g., UCSC rn4, see www.genome.ucsc.edu and http://genome.ucsc.edu/FAQ/FAQreleases.html) unless otherwise specified.

In one aspect the host non-human vertebrate mu constant region for forming the chimaeric IgM antibody/heavy chain may be at a different (non endogenous) chromosomal locus. In this case the inserted human DNA, ie, the human variable V,D,J and C gene segments, may then be inserted into the non-human genome at a site which is distinct from that of the naturally occurring heavy locus. Endogenous heavy chain expression is inactivated.

Reference to location of a human variable region, constant region or a gene segment upstream or downstream of an endogenous mu constant region means that there is a suitable relative location of the antibody nucleotide elements to enable formation of mu and then non-mu heavy chains in vivo in the vertebrate. Thus, the inserted human DNA and endogenous constant region and any other endogenous sequences are in operable connection with one another for antibody or antibody chain production.

As a source of human and non-human antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest*, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization bY Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, *Methods in Molecular Biology*™, Human Press. Also at World Wide Web (www) blogsua.com/pdf/antibody-engineering-methods-and-protocolsantibody-engineering-methods-and-protocols.pdf Samples from which B-cells can be obtained include but are not limited to blood, serum, spleen, splenic tissue, bone marrow, lymph, lymph node, thymus, and appendix. Antibodies and immunoglobulin chains can be obtained from each of the previous-mentioned samples and also from the following non-limiting list of B-cells, ascites fluid, hybridomas, and cell cultures.

"Plurality" is used in the ordinary sense of the term and means "at least one" or "more than one".

"Derived from" is used in the ordinary sense of the term. Exemplary synonyms include "produced as", "resulting from", "received from", "obtained from", "a product of", "consequence of", and "modified from" For example, a human variable region of a heavy chain can be derived from recombination of human VH, D and JH gene segments and this reflects the in vivo recombination of these gene segments in, for example, a transgenic heavy chain locus according to the invention with any accompanying mutation (eg, junctional mutation). A constant region or gene segment sequence is derived from a human individual if, for example it is an identical nucleotide copy of that region or segment as found in the genome of that individual (or found in a ethnic or geographical population of humans of which the individual is a member). Populations and genomic variant immunoglobulin gene sequences can be found, eg, in the 1000 Genomes database or by sampling DNA from humans and sequencing.

In one embodiment in any configuration of the invention, the genome of a or each vertebrate or cell has been modified to prevent or reduce the expression of fully-endogenous antibody or heavy chains. Examples of suitable techniques for doing this can be found in WO2011004192, U.S. Pat. Nos. 7,501,552, 6,673,986, 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus. For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the or each vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

The term "immunoglobulin" (Ig) is used interchangeably with "antibody" herein.

An "isolated" antibody or heavy chain is one that has been identified, separated and/or recovered from a component of its production environment (e.g., naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide, chain or antibody will be prepared by at least one purification step.

An "antibody fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

An antibody that "specifically binds to" or is "specific for" a particular polypeptide, antigen, or epitope is one that binds to that particular polypeptide, antigen, or epitope without substantially binding to other polypeptides, antigens or epitopes. For example, binding to the antigen or epitope is specific when the antibody binds with a $K_D$ of 100 µM or less, 10 µM or less, 1 µM or less, 100 nM or less, eg, 10 nM or less, 1 nM or less, 500 pM or less, 100 pM or less, or 10 pM or less. The binding affinity ($K_D$) can be determined using standard procedures as will be known by the skilled person, eg, binding in ELISA and/or affinity determination using surface plasmon resonance (eg, Biacore™ or KinExA™ solution phase affinity measurement which can detect down to fM affinities (Sapidyne Instruments, Idaho)).

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

In one embodiment of any configuration of the vertebrate or cell of the invention the genome comprises an antibody light chain locus which comprises all or part of the human Igλ locus including at least one human Jλ region and at least one human Cλ region, optionally $C_\lambda 6$ and/or $C_\lambda 7$. Optionally, the light chain locus comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. The human lambda immunoglobulin locus comprises a unique gene architecture composed of serial J-C clusters. In order to take advantage of this feature, the invention in optional aspects employs one or more such human J-C clusters. Thus, optionally the light chain locus comprises at least one human $J_\lambda$-$C_\lambda$ cluster, optionally at least $J_\lambda 7$-$C_\lambda 7$. The construction of such transgenes is facilitated by being able to use all or part of the human lambda locus such that the transgene comprises one or more J-C clusters in germline configuration, advantageously also including intervening sequences between clusters and/or between adjacent J and C regions in the human locus. This preserves any regulatory elements within the intervening sequences which may be involved in VJ and/or JC recombination and which may be recognised by endogenous AID (activation-induced deaminase).

An aspect provides a nucleotide sequence encoding the antibody or heavy chain of the invention, optionally wherein the nucleotide sequence is part of a vector. Suitable vectors will be readily apparent to the skilled person, eg, a conventional antibody expression vector comprising the nucleotide sequence together in operable linkage with one or more expression control elements.

An aspect provides a pharmaceutical composition comprising the antibody or heavy chain of the invention and a diluent, excipient or carrier, optionally wherein the composition is contained in an IV container (eg, and IV bag) or a container connected to an IV syringe.

An aspect provides the use of the antibody or heavy chain of the invention in the manufacture of a medicament for the treatment and/or prophylaxis of a disease or condition in a human patient.

The skilled person will generally be familiar with standard cloning techniques and recombinant DNA technology—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody heavy chains produced according to the present invention, and use of said antibodies in human medicine. The invention also relates to a pharmaceutical composition comprising such an antibody or heavy chain and a pharmaceutically acceptable carrier or other excipient.

Methods for the generation of both monoclonal and polyclonal antibodies are well known in the art, and the present invention relates to both polyclonal and monoclonal antibodies of fully humanised antibodies and heavy chains produced in response to antigen challenge in a vertebrate, cell or population of non-human vertebrates according to the present invention.

In a further aspect, the invention relates to use of a population of non-human vertebrates of the present invention in the analysis of the likely effects of drugs and vaccines in the context of a human antibody heavy chain repertoire.

The invention also relates to a method for identification or validation of a drug or vaccine, the method comprising delivering the vaccine or drug to a population of vertebrates of the invention and monitoring one or more of: the immune response, the safety profile; the effect on disease.

The invention also relates to a kit comprising an antibody, heavy chain or antibody derivative as disclosed herein and either instructions for use of such antibody, derivative or chain or a suitable laboratory reagent, such as a buffer, antibody detection reagent.

The invention also relates to a method for making an antibody, or part thereof, the method comprising providing:
(i) a nucleic acid encoding an antibody or heavy chain, obtained using the vertebrate, cell or population of the present invention; or (ii) sequence information from which a nucleic acid encoding an antibody or heavy chain, obtained using the vertebrate, cell or population of the present invention can be expressed to allow an antibody or heavy chain to be produced.

In an embodiment, each vertebrate is a non-human vertebrate, mouse or rat, whose genome comprises
(a) said gene locus, wherein the gene locus is a transgenic heavy chain locus (ie, at the endogenous heavy chain locus position); and
(b) an antibody kappa light chain locus transgene and/or an antibody lambda chain locus transgene;
wherein all of the V, D and J in said transgenes are human V, D and J;
wherein endogenous antibody heavy and light chain expression has been inactivated; and optionally wherein said genome is homozygous for said heavy and light chain loci. This is useful for generating, predictably, only human antibodies and chains in the vertebrate (and population comprising such vertebrates) when all light chain constant regions are human.

In an embodiment, the kappa chain transgenic loci comprises a substantially complete human functional Vκ and Jκ repertoire; and the lambda chain transgene comprises a substantially complete human functional Vλ and Jλ repertoire. "Functional" here acknowledges that Ig gene segment pseudogenes and non-functional human Ig gene segments can be excluded.

In one example the gene locus of the invention is a heavy chain locus which comprises a S-mu switch (eg, endogenous S-mu) 5' of the endogenous mu constant region and a human gamma constant region 3' of the endogenous mu constant region, with a S-gamma switch (eg, a human or endogenous S-gamma) between the Cmu and Cgamma regions. For example, the C-mu region and switches are mouse 129 C-mu region and switches; or the C-mu region and switches are mouse Black 6 C-mu region and switches. In another embodiment (where the non-human vertebrate species is mouse or rat), S-mu is a rat Smu and the C-mu region is mouse and optionally there is a mouse S-gamma 3' of the C-mu region.

In one aspect each vertebrate is a mouse whose genetic background is selected from mouse strains C57BL/6, M129 such as 129/SV, BALB/c, and any hybrid of C57BL/6, M129 such as 129/SV, or BALB/c. In an embodiment, each of these vertebrates have the same genetic background but two or more of the vertebrates of the population differ in their human gene segment repertoires (eg, in their human C region gene segment repertoires).

In an embodiment, the J segments of each gene locus of the invention are human JH gene segments; optionally wherein each heavy chain locus comprises a substantially complete functional repertoire of human JH gene segments.

In an embodiment, each gene locus of the invention comprises at least 2, 3, 4, 5 or 6 different human JH gene segments.

In an embodiment, the D segments of each gene locus of the invention are human D gene segments; optionally wherein each heavy chain locus comprises a substantially complete functional repertoire of human D gene segments.

In an embodiment, each gene locus of the invention comprises at least 5, 10, 15, 20, 25, 26 or 27 different human D gene segments.

In an embodiment, the heavy chain loci of said vertebrates comprise identical human D and JH gene segment repertoires, but differ in their VH gene repertoires.

In an embodiment, each heavy chain locus comprises at least two human JH gene segments selected from the group consisting of J1, J2, J3, J4, J5 and J6; optionally all of the gene segments of the group.

In an embodiment, each vertebrate comprises human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3-74;
wherein the VH gene repertoire comprises a substantially complete human functional VH gene repertoire.

In an embodiment, endogenous antibody heavy chain expression has been inactivated in the vertebrate or cell of the invention. For example, less than 10, 5, 4, 3, 2, 1 or 0.5% of heavy chains are provided by endogenous heavy chains (ie, heavy chains whose variable regions are derived from recombination of non-human vertebrate V, D and J gene segments).

The VL gene segments of a repertoire can, in one embodiment, be recombined VL, ie, provided as part of a variable region sequence derived from the recombination of human VL with JL (eg, where the VI and JL are human).

In an embodiment, the J segments of each transgenic light chain locus are human JL gene segments; optionally wherein each light chain locus comprises a substantially complete functional repertoire of human Jκ or Jλ gene segments (eg, each transgenic locus comprises human Vλ gene segments and Jλ gene segments, optionally a substantially complete functional repertoire of human Jλ gene segments; or each transgenic locus comprises human Vκ gene segments and Jκ gene segments, optionally a substantially complete functional repertoire of human Jκ gene segments).

In an embodiment, the kappa chain repertoire provided by said population comprises a substantially complete repertoire of functional human Vκ gene segments; optionally providing at least 5 different human Jκ gene segments and at least at least 40 different human Vκ gene segments.

In an embodiment, the kappa chain repertoire provided by said population comprises at least 20, 25, 30, 35 or 40 different human Vκ gene segments.

In an embodiment, the lambda chain repertoire provided by said population comprises a substantially complete repertoire of functional human Vλ gene segments; optionally providing at least 5 different human Jλ gene segments and at least 40 different human Vλ gene segments.

In an embodiment, the lambda chain repertoire provided by said population comprises at least 20, 25, 30, 35 or 40 different human Vλ gene segments.

In an embodiment, each light chain locus of the vertebrate or cell comprises at least 2, 3, 4, 5 or 6 different human Jκ or Jλ gene segments.

In an embodiment, the light chain loci of said vertebrate or cell comprise identical human JL gene segment repertoires, but differ in their VL gene repertoires.

In an embodiment, endogenous antibody kappa and/or lambda light chain expression has been inactivated in the vertebrate or cell.

In an embodiment, said transgenic light chain loci of the vertebrate or cell are kappa light chain loci (at the endogenous kappa loci, ie, corresponding to the position of a kappa locus in a wild-type non-human vertebrate genome). For example, a transgenic kappa locus can comprise human Vκ gene segments and Jκ gene segments upstream of a constant region (eg, a CH, Cλ or Cκ gene segment; optionally which is an endogenous or human gene segment). For example, a transgenic kapppa locus can comprise human Vλ gene segments and Jλ gene segments upstream of a constant region (eg, a CH, Cλ or Cκ gene segment; optionally which is an endogenous or human gene segment).

In an embodiment, said transgenic light chain loci of the vertebrate or cell are lambda light chain loci (at the endogenous lambda loci, ie, corresponding to the position of a lambda locus in a wild-type non-human vertebrate genome). For example, a transgenic lambda locus can comprise human Vκ gene segments and Jκ gene segments upstream of a constant region (eg, a CH, Cλ or Cκ gene segment; optionally which is an endogenous or human gene segment). For example, a transgenic lambda locus can comprise human Vλ gene segments and Jλ gene segments upstream of a constant region (eg, a CH, Cλ or Cκ gene segment; optionally which is an endogenous or human gene segment).

For selection of antibodies and heavy chains in the methods of the invention, examples of a desirable antibody/chain characteristic are affinity for binding a predetermined antigen or epitope (eg, as determined by surface plasmon resonance), completion with a known antibody for binding to a predetermined antigen or epitope, epitopic specificity of the antibody (eg, as determined by X-ray crystallography, competition with a known antibody for antigen binding wherein the known antibody specifically binds to the antigen (eg, as determined by surface plasmon resonance, eg, Biacore™), performance in ELISA or another immunoassay, a desirable biophysical characteristic (eg, melting temperature, pI, solution state, degree of aggregation, storage profile etc). In an embodiment, affinity is determined by surface plasmon resonance.

Methods of immunisation for use in the invention are well known to the skilled person and may involve a classic prime-boost regime, RIMMS or any other protocol. An adjuvant may be administered with the antigen, as is known in the art.

The invention provides a pharmaceutical composition comprising an antibody or heavy chain selected as described above or a derivative thereof that binds said antigen, together with a pharmaceutically acceptable diluent, carrier or excipient.

Examples of derivative antibodies/chains (according to any aspect herein) are antibodies/chains that have one or more mutations compared to the isolated antibody or chain (eg, to improve antigen-binding affinity and/or to enhance or inactivate Fc function) Such mutants specifically bind the antigen. Mutation or adaptation to produce a derivative includes, eg, mutation to produce Fc enhancement or inactivation. A derivative can be an antibody following conjugation to a toxic payload or reporter or label or other active moiety.

In an embodiment of any configuration, the vertebrate is (or vertebrates of the populatio are) naïve (ie, not immunised with a predetermined antigen, as the term is understood in the art; for example, such a vertebrate that has been kept in a relatively sterile environment as provided by an animal house used for R&D). In another example, the vertebrates have been immunised with a predetermined antigen, eg, an antigen bearing a human epitope. In another example, the population comprises naïve and immunised vertebrates.

In an embodiment of the population or method, the vertebrates have been immunised with the same antigen (eg, a human antigen).

In an embodiment of the population or method, the vertebrates are naïve.

In an embodiment of the population or method, the vertebrates have a common collection of light chain loci. For example, the kappa chain loci alleles are identical in the vertebrates and/or the lambda chain loci alleles are identical in the vertebrates. This simplifies construction of vertebrate variants for producing the population and also simplifies breeding.

In an embodiment, the method comprises comprising selecting one or more antibody heavy chains (eg, as part of an antibodies) from said population or repertoire according to a desired characteristic (eg, affinity for biding an antigen).

In one example, the cell is a B-cell, hybridoma, ES cell or iPS cell. ES cells and iPS cells can be used to develop corresponding non-human vertebrates (vertebrates of the invention).

In an embodiment, the vertebrate species is selected from human, mouse, rat, rabbit, guinea pig, chicken, a fish, a bird, a reptile, a Camelid, bovine, chimpanzee, a non-human primate and a primate.

In an embodiment, the vertebrate is a mouse or rat.

Aspects of the invention are as follows:—

1. A non-human vertebrate (eg, a mouse or a rat) or a non-human vertebrate cell (eg, a mouse cell or a rat cell) whose genome comprises a gene locus for expression of antibody heavy chains, the locus comprising
   (a) an unrearranged human variable region comprising human variable region gene segments for expression of a repertoire of human variable domains;
   (b) an endogenous mu constant region for expression of IgM antibody heavy chains comprising endogenous mu heavy chain constant domains and human variable domains; and
   (c) a humanised non-mu constant region downstream of the mu constant region for expression of non-mu antibody heavy chains comprising human non-mu constant domains and human variable domains;
   Wherein the unrearranged variable region is provided as a targeted insertion of the human variable region gene segments upstream of the endogenous mu constant region in an endogenous IgH locus such that the variable region gene segments are able to recombine for expression and selection in the context of an endogenous mu constant region.

2. The vertebrate or cell of aspect 1 comprising an antibody heavy chain locus that comprises (in 5' to 3' direction) an unrearranged human variable region, a first switch, an endogenous mu constant region, a second switch and a human constant region of said non-mu isotype; wherein the heavy chain locus is capable of undergoing switching from IgM to the non-mu isotype; optionally wherein the first switch is a rodent (eg, mouse or rat) Smu or the endogenous Smu of the IgH locus.

3. The vertebrate or cell of aspect 1 or 2, wherein the genome comprises endogenous RAG-1 and RAG-2 genes.

4. The vertebrate or cell of any preceding aspect, wherein the human variable region comprises a plurality of unrearranged human VH gene segments; optionally at least 5 different human VH gene segments or a substantially complete human functional VH gene repertoire.

For example, the variable region comprises human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3-74; wherein the VH gene repertoire comprises a substantially complete human functional VH gene repertoire.

5. The vertebrate or cell of any preceding aspect, wherein the human variable region comprises a plurality of unrearranged human D gene segments; optionally at least 5 or 20 different human D gene segments or a substantially complete functional repertoire of human D gene segments.

For example, the human variable region comprises at least 10 human D gene segments selected from the group consisting of D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26, D6-25 and D7-27; optionally all of the gene segments of the group.
6. The vertebrate or cell of any preceding aspect, wherein the human variable region comprises a plurality of unrearranged human JH gene segments; at least 2 different human JH gene segments or a substantially complete functional repertoire of human D gene segments.
7. The vertebrate or cell of aspect 1 or 2, which does not express endogenous antibody heavy chains of said non-mu isotype.
8. The vertebrate or cell of any preceding aspect, wherein the non-mu constant region is a human gamma constant region.
9. The vertebrate or cell of aspect 8, wherein the gamma constant region comprises CH2 and CH3 gene segments for encoding an antibody Fc region.
10. The vertebrate or cell of aspect 9, wherein the CH2 and CH3 gene segments encode for an inactivated Fc region.
11. The vertebrate or cell of aspect 9, wherein the CH2 and CH3 gene segments encode for an activated Fc region.
12. The vertebrate or cell of any preceding aspect, wherein the genome comprises no human Cmu genes.
13. The vertebrate or cell of any preceding aspect, wherein the or all non-mu heavy chain constant regions in the genome comprise a CH1.
14. The vertebrate or cell of any preceding aspect, wherein the genome comprises a light chain locus comprising human VL and JL gene segments upstream of a constant region for expression of light chains comprising human variable regions; optionally wherein the constant region is a human light chain constant region.
15. The vertebrate or cell of aspect 14, which does not substantially express endogenous light chains.
16. The vertebrate or cell of any one of aspects 8 to 11, wherein the gamma constant region does not comprise a CH1 gene segment.
17. The vertebrate or cell of aspect 16, wherein light chain expression is inactive when the non-mu heavy chains are expressed.
18. The vertebrate or cell of any preceding aspect, wherein the locus comprises a replacement of endogenous non-mu constant region gene segments (eg, CH2 and CH3 gene segments) with corresponding human constant region gene segments (eg, CH2 and CH3 gene segments) of the same non-mu isotype; optionally wherein an endogenous switch of said non-mu isotype is retained.
19. The vertebrate or cell of any preceding aspect, wherein the locus comprises an insertion of a human gamma constant region nucleotide sequence comprising sequence from the human gamma CH2 gene segment to the human gamma CH3 gene segment, wherein the insertion replaces a corresponding sequence of an endogenous gamma constant region in the genome of the vertebrate or cell.
20. The vertebrate or cell of any preceding aspect, wherein endogenous inter-gene segment sequences have been retained so that the heavy chain locus comprises said human non-mu constant region gene segments flanked by endogenous constant region inter-gene segment sequences.
21. The vertebrate or cell of any preceding aspect, wherein the locus comprises a replacement of endogenous gamma constant region gene segments (eg, gamma CH2 and CH3 gene segments) with human gamma constant region gene segments (eg, gamma CH2 and CH3 gene segments), but endogenous sequences between gamma constant regions have been retained.
22. A population of vertebrates according to any preceding aspect, wherein the population comprises
    (i) a first vertebrate wherein the locus is an antibody heavy chain locus that comprises one or more first human non-mu C gene segment(s) (eg, a human CH1, CH2 or CH3; or an Fc) or a first human constant region;
    (ii) and a second vertebrate wherein the locus is an antibody heavy chain locus that comprises one or more second human non-mu C gene segment(s) (eg, a human CH1, CH2 or CH3; or encoding an Fc) or a second constant region; and
    wherein the first and second gene segments or regions are the same type of C gene segment(s) (eg, both CH1 gene segments or both encoding an Fc) or regions and the second gene segment(s) is a variant of the first gene segment(s).
23. The population of aspect 22, wherein the first and second constant regions are gamma constant regions of the same sub-type (eg, both gamma-2 or gamma-3).
24. The population of aspect 22 or 23, wherein the second gene segment is a synthetic mutant of the first gene segment.
25. The population of aspect 22, wherein one or both of the first and second gene segment(s) encodes an inactivated human gamma Fc.
26. The population of aspect 22, wherein one or both of the first and second gene segment(s) encodes an activated human gamma Fc.
27. A method of isolating an antibody or human heavy chain, the method comprising immunising a vertebrate or population of vertebrates according to any preceding aspect with an antigen and isolating a non-mu antibody or heavy chain from said vertebrate or a vertebrate of the population, wherein the isolated antibody or heavy chain specifically binds to the antigen and comprises (or is) a fully human heavy chain of said non-mu isotype.
28. A pharmaceutical composition comprising the isolated antibody or heavy chain recited in aspect 27 or a copy or derivative thereof.
29. A method of obtaining a humanised and affinity matured antigen-specific antibody heavy chain, the method comprising humanising the heavy chain in vivo in a non-human vertebrate (eg, a mouse or a rat) comprising functional RAG and activation induced cytidine deaminase (AID) by immunising the vertebrate with the antigen and obtaining recombination of VH,D and JH gene segments in vivo, somatic hypermutation and isotype switching in a B-cell of the vertebrate from an endogenous mu isotype to a human non-mu isotype, wherein a repertoire of affinity matured antigen-specific non-mu antibody heavy chains are produced and expressed by the vertebrate, the non-mu constant domains of the heavy chains being human constant domains, the method further comprising isolating one or more of said humanised heavy chains.
30. The method of aspect 29, wherein the variable domain of each isolated heavy chain is a human variable domain.

31. The method of aspect 29 or 30, wherein the vertebrate is according to any one of aspects 1 to 21.
32. A pharmaceutical composition comprising an isolated antibody heavy chain obtained in the method of aspect 29, 30 or 31 or a copy or derivative thereof; optionally wherein the heavy chain, copy or derivative is provided by an antibody that specifically binds the antigen.
33. The method of any one of aspects 27, 29, 30 or 31 comprising the step of isolating a B-cell from said immunised vertebrate (or an immunised vertebrate of said population), wherein the B-cell expresses a said isolated antibody or heavy chain; and optionally immortalising the B-cell.
34. The method of any one of aspects 27, 29, 30, 31 or 32, comprising isolating a nucleotide sequence from said immunised vertebrate or B-cell, wherein the nucleotide sequence encodes a said isolated antibody or a heavy chain thereof.
35. A vector (optionally in a host cell) comprising the nucleotide sequence recited in aspect 34 or a copy thereof.
36. A method of treating or preventing a medical condition or disease in a human associated or caused by said antigen, the method comprising administering to the human the antigen-specific antibody or heavy chain obtained in the method of any one of aspects 21, 23, 24, 25, 27 and 28.
37. The antigen-specific antibody or heavy chain obtained in the method of any one of aspects 27, 29, 30 or 31 for use in the treatment or prophylaxis of a medical condition or disease in a human associated or caused by said antigen.
38. Use of the antigen-specific antibody or heavy chain obtained in the method of any one of aspects 27, 29, 30 or 31 in the manufacture of a medicament for use in the treatment or prophylaxis of a medical condition or disease in a human associated or caused by said antigen.

It will be understood that particular embodiments described herein are shown by way of illustration and not as limitations of the invention and (unless the context states otherwise) embodiments can be applied to any of the configurations of the invention described herein. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions, populations, vertebrates, antibodies, repertoires and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting prophetic Examples.

EXAMPLES

Example 1

"Recombineered BAC Vectors to Add Human C Gene Segments to the Mouse Genome"

Methods of replacing endogenous antibody gene segments with corresponding human gene segments harboured by BACs are generally known in the art, eg, as disclosed in WO02066630, WO2011163311 & WO2011163314 (Regeneron). These methods use standard homologous recombination. As an alternative, recombinase mediated cassette exchange (RMCE; see WO2011004192 & WO2011158009 (Kymab Limited)) can be used with cre-lox-mediated, transposon-mediated (eg, using piggyBac) or homologous recombination-mediated deletion of endogenous non-mu constant region sequences, in order to replace endogenous non-mu with human constant region gene segments.

Modified BACs with human C gene segments, for example created using the methods described in Example 1, can be used to alter the genome of non-human mammals (eg, mice or rats). These alterations can result in an intact Ig heavy chain locus in which normal immunoglobulin gene segment recombination results in VDJ combinations which includes human VH, D and JH gene segments. An example of how to insert human V, D and J gene segments into a non-human vertebrate genome is disclosed in the Regeneron and Kymab PCT applications cited above. These methods are also useful for inserting human C region sequences.

Standard recombineering methods can be used to introduce human C gene segments and regions into BACs for use in inserting non-human vertebrate genomic DNA into the genome of a non-human vertebrate embryonic stem cell (ES cell), eg, using standard homologous recombination or RMCE. In one embodiment, as a first step a genomic fragment containing a human constant region nucleotide sequence (encoding one or more human constant domains) of a human genomic sequence is inserted into a bacterial artificial chromosome (BAC) vector by standard techniques. Preferably, such a BAC, which can range in size from 20-kb to 200-kb or more, can be isolated from commercially available libraries of BACs (eg, Caltec A, B, C or D human BAC library or RPCI-11 human BAC library, Invitrogen) by standard techniques including sequence searches or by hybridization to bacterial colonies containing BACs to identify those with a BAC of interest.

In the present example, a BAC is chosen that contains a human gamma-1 constant region nucleotide sequence comprising from the CH1 gene segment to the polyA immediately 5' of M2 of a human genomic sequence. Using conventional techniques, the endogenous gamma-1 constant region gene segments can be replaced by the corresponding human gamma-1 constant region gene segments. In this example, two steps are required. The first step replaces the C domain coding exon of an endogenous C gene segment with a positive-negative selection operon, in this example, an operon encoding an ampicillin resistance gene (Amp) and a streptomycin-sensitizing ribosomal protein (rpsL). Certain strains of bacteria can be selected for the absence of the rpsL gene by resistance to streptomycin. Short stretches of DNA homologous to sequences flanking the endogenous C gene exon are placed 5' and 3' of the rpsL-Amp operon. In the presence of appropriate recombination factors per standard recombineering techniques (eg, homologous recombination) recombination between the operon fragment and the BAC will result in replacement of the endogenous C gene exon with the operon which are selected by resistance to ampicillin. The second step uses the same homologous sequences in order to replace the inserted operon with a corresponding human C gene segment. Successful integrations of the human gene segment are selected in bacteria that become resistant to streptomycin due to the loss of the operon, specifically the rpsL portion.

In this example, the two step process as described can be repeated for each of the endogenous C gene segments until the desired endogenous non-mu constant region has been humanised by replacement of endogenous constant region gene segments with human counterparts. The method can be used similarly to replace an entire endogenous non-mu constant region (including gene segments and inter-gene segment sequences) with the corresponding human non-mu constant region sequence; or just the endogenous C gene segments of the non-mu constant region can be placed (leaving endogenous inter-gene segment sequences in place between the human C gene segments).

As is standard, genetically-manipulated stem cells can be inserted into blastocysts and implanted into foster mothers in order to give rise to live-born progeny animals bearing human C gene segments in heavy chain loci according to the invention. Standard breeding can yield progeny that are homozygous for the heavy chain locus of the invention and in which endogenous heavy chain expression (ie, chains comprising endogenous variable regions) has been inactivated using conventional techniques.

Example 2

"Adding Human C Gene Segments to A Non-Human Vertebrate Genome using SRMCE of Modified BACs"

As mentioned above, one technique to integrate modified BACs with human C gene segments into a genome is sequential recombinase mediated cassette exchange (sRMCE). The technique is described in WO2011004192 (Kymab Limited), which is incorporated here in its entirety by reference.

sRMCE provides for a locus modified with a 'landing pad' inserted at a specific location. This insertion can either be de novo via homologous recombination or as a consequence of a previous BAC insertion. In this example, the landing pad is inserted in the mouse IgH locus (in a mouse ES cell) 3' of the mouse C-mu region. In the present example, the insertion is between the mouse C-mu and mouse C-gamma regions (eg, between mouse Cmu and Cdelta or between mouse Cdelta and mouse gamma-1). Using standard sRMCE with serial BACs, a human gamma-1 constant region is built up in the genome of the ES cell (and optionally the mouse gamma-1 constant region or all mouse non-mu constant regions are deleted or replaced similarly with the corresponding human constant region sequences). In another example, serial BACs are used with sRMCE to insert the entire human sequence from the human delta or gamma-3 constant region to (and including) the human gamma A2 constant region. The mouse constant region from delta or gamma-1 to (and including) alpha is deleted (or just the mouse gamma constant regions are deleted). BAC insertion via SRMCE techniques are also used for the addition of human VH, DH and J gene segments immediately downstream of the 3'-most mouse JH gene segment. Endogenous mouse VDJ is inactivated or deleted.

An alternative embodiment is to replace the endogenous mouse C gamma-1 with a 'landing pad' via homologous recombination. Using standard sRMCE a construct containing human C gamma-1 exons 1 to 4, fused to mouse C gamma-1 transmembrane and cytoplasmic exons, replaces the endogenous C gamma-1 segments. The construct is assembled by PCR from human and mouse BACS exploiting a conserved SPGK amino acid motif at the 3' end of exon 4 in both human and mouse C gamma-1, which aids construction using PCR. The rationale for using a chimeric C gamma-1 construct is that the secretory form of IgG1 is fully human whilst the membrane-bound form of IgG1 maintains normal mouse signalling.

A further embodiment would be to use the same landing pad and a similar human-mouse C gamma-1 construct described previously, but in this example the construct lacks human C gamma-1 exon 1 and so ablates heavy and light chain pairing, thus a heavy-chain only IgG1 is expressed.

ES cell clones with correct insertions are selected from a pool of clones without insertions or with non-productive insertions by resistance to puromycin as described in WO2011004192. Resistance to puromycin results from the juxtaposition of an active promoter element, PGK, with the puroTK coding region. Correct insertions are verified by standard techniques including PCR of junctions, PCR of internal elements, Southern blotting, comparative genomic hybridization (CGH), sequencing and etc. In the example, as described in WO2011004192, correct lox2272-lox2272 and loxP-loxP recombination also results in two intact sets of piggyBac elements that did not exist prior to insertion. An intact piggyBac element is comprised of a set of inverted repeats which are depicted in the figure by "PB5'" and "PB3'". An appropriated oriented set of piggyBac elements are the substrate of piggyBac transposase which can catalyse recombination between the elements, resulting in deletion of intervening sequences as well as both elements. The DNA remaining after a piggyBac transposition is left intact and is lacking any remnant of the piggyBac element. In the example, ES cell clones with successful piggyBac transposition are selected by loss of the active puroTK element which renders the cells resistant to the drug FIAU.

In an alternative method, it is possible to use standard homologous recombination using BACs instead of RMCE (eg, see the techniques disclosed in the Regeneron and Ablexis PCT applications mentioned above). In this case, vectors would be constructed in which each vector comprises a stretch of genomic human constant region DNA flanked by homology arms. The homology arms would have the sequence of the DNA in the recipient ES cell genome that flanks the insertion site (for example, flanking a mouse constant region sequence to be replaced by insertion of the human DNA). Using serial homologous recombination steps (optionally using BACS with overlapping homology arms as described in WO2009076464) the human constant region(s) can be built up in a process that replaces mouse constant region DNA. Alternatively, insertion of human DNA can be in a separate step from deletion of mouse constant region DNA (eg, using site-specific recombination such as cre-lox or transposon-mediated deletion such as using piggyBac).

The final product is an ES cell whose genome comprises a transgenic IgH locus with a plurality of human VH, D and JH gene segments upstream of a mouse S-mu switch, mouse mu constant region, a gamma switch (optionally the mouse S-gamma is retained, or the human S-gamma can be inserted together with the other human gamma constant region sequences) and a human gamma constant region (eg, at least a human gamma-1 constant region). Expression of mouse variable regions is inactivated (eg, by inversion of the mouse V, D, J as described in WO2011004192 or by deletion of all or part (eg, the J gene segments) of the mouse IgH variable region gene segments. Using standard techniques progeny mice are developed from the transgenic ES cells (the mice being preferably homozygous for the transgenic heavy chain locus). As is well known to those skilled in the art, an ES cell clone can be used to create a line of genetically modified mice via injection of said cells into a mouse blastocyst embryo, transferring the injected embryo to a suitable recipient and breeding the chimeric offspring that result. The modified gene locus can be propagated through breeding and made either heterozygous or homozygous depending on the genetic cross.

The human variable region gene segments are positioned such that they can participate in the recombination events associated with B cell maturation yielding VDJ gene segments and mouse C-mu constant domains. Isotype switching to a human constant region (eg, C gamma-1) will yield transcripts that encode fully human, mature heavy chains comprising human variable regions (with somatic hypermutation caused by mouse AID) and human constant domains. Productive transcripts will be expressed by the progeny mice (ie, the mouse's in vivo antibody-producing machinery is harnessed to select for productive transcripts that can be expressed) and the skilled person will know at the outset that all gamma-1 type chains will be human (where the heavy chain loci have been humanised to include human gamma-1 constant region and exclude mouse gamma-1 constant region). Commercially-available antibodies can be used to select and isolated specific human IgG isotypes (eg, rabbit anti-human IgG1, Catalogue Number: AP20578PU-N from Acris Antibodies GmbH; mouse anti-human IgG2, Catalogue Number: AM08152AP-N from Acris Antibodies GmbH; mouse anti-human IgG3, Catalogue Number: MCA516P or sheep-anti human Ig3, Catalogue Number: AP05355HR-N from AbD Serotec; mouse anti-human IgG4, Catalog NumberMCA2098P from AbD Serotec). For example, progeny mice are immunised with a human target antigen or a viral or bacterial antigen and IgG1 antibodies are selected for antigen binding isolated. These will have fully human heavy chains and be specific for the target antigen. If the progeny mice are engineered (using standard techniques, eg, as disclosed in the Kymab Limited or Regeneron PCT applications disclosed above) to include humanised light chain loci (eg, kappa and/or lambda light chain loci in which the mouse constant and variable regions have been deleted or inactivated and there has been inserted human light chain variable region VL and JL gene segments and optionally also human constant regions) the isolated IgG1 antibodies will have fully human variable region and, if the light chain loci bear only human constant region genes, the IgG1 antibodies will be fully human, well expressed and selected by an in vivo system. Additionally, they will specifically bind target antigen when the mice have been immunised and IgG1 have been selected against said target. This represents a reliable and much simpler technique for obtaining fully human antibodies (or antibodies with fully human heavy chains) than as presently possible with the multi-step methods of the art which rely on in vitro manipulation and selection using antibody engineering to humanise antibodies.

In a variation, light chain expression is inactivated in progeny mice, eg, by deletion of the mouse kappa (and optionally also lambda) variable region or part thereof (eg, JL gene segments) or by deletion of kappa (and optionally also lambda) constant regions in the light chain loci. In this case, human gamma constant regions are inserted (eg, for all IgG subtypes, or at least for IgG1), in which the human CH1 gene segments (and optionally hinge regions) are omitted. In the mouse mu constant region, CH1 can be retained (eg, see WO2011072204, the disclosure of which is incorporated herein by reference). These mice produce heavy-chain only antibodies (H2 antibodies) lacking CH1 domains and devoid of light chains. These heavy-chain only antibodies are fully human (human variable and constant domains, eg human gamma-1 constant domains when the heavy chain loci in the mice have been humanised by insertion of human gamma-1 constant regions and inactivation or deletion of mouse gamma-1 constant regions). Following immmunisation with a human target antigen or a viral or bacterial antigen, heavy chain-only antibodies can be selected that are specific for the antigen of interest, fully human, well expressed and selected by an in vivo system.

The invention claimed is:

1. A mouse, whose genome comprises a gene locus for expression of antibody heavy chains, said locus comprising:
   (a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and
   (b) a non-mu heavy chain constant region comprising non-mu heavy chain constant region gene segments comprising a human CH2 gene segment and a human CH3 gene segment encoding non-mu antibody heavy chains comprising (i) non-mu heavy chain constant domains and (ii) human heavy chain variable domains; wherein said unrearranged human heavy chain variable region is upstream of and operably linked to said non-mu heavy chain constant region at an endogenous IgH locus and said human CH2 and human CH3 gene segments are in place of endogenous non-mu heavy chain constant region DNA, such that said human heavy chain variable region gene segments are able to recombine for expression of a non-mu antibody heavy chain comprising a human non-mu heavy chain antibody Fc region comprising a human CH2 and a human CH3 and a human heavy chain variable domain, wherein in said genome, human DNA is incorporated only at endogenous Ig antibody loci.

2. The mouse according to claim 1, wherein said genome comprises endogenous recombination activating gene 1 (RAG-1) and recombination activating gene 2 (RAG-2) genes.

3. The mouse according to claim 1, wherein said unrearranged human variable region of said locus comprises a plurality of unrearranged human D and/or JH gene segments.

4. The mouse according to claim 3, wherein said plurality of unrearranged human D gene segments, comprises-at least 5 different human D gene segments.

5. The mouse according to claim 4, wherein said plurality of unrearranged human JH gene segments, comprises at least 2 different human JH gene segments.

6. The mouse of claim 1, wherein said non-mu constant region of said locus comprises a human gamma constant region comprising a human gamma CH2 gene segment and a human gamma CH3 gene segment, wherein said human gamma CH2 and human gamma CH3 gene segments encode an antibody Fc region.

7. The mouse of claim 6, wherein said CH2 and CH3 gene segments encode an inactive Fc region.

8. The mouse of claim 6, wherein said CH2 and CH3 gene segments encode an active Fc region.

9. The mouse of claim 6, wherein said genome comprises no human Cmu genes.

10. The mouse of claim 6, wherein said gamma constant region does not comprise a human CH1 gene segment.

11. The mouse of claim 10, wherein light chain expression is inactive when non-mu heavy chains are expressed in the mouse.

12. The mouse of claim 11, wherein said IgH locus comprises said human CH2 and human CH3 gene segments are in place of corresponding endogenous non-mu heavy chain constant region gene segments of the same non-mu isotype.

13. The mouse of claim 6, wherein said human gamma CH2 and human gamma CH3 gene segments are in place of endogenous gamma constant region DNA in said genome of said mouse, whereby the human gamma CH2 and CH3 gene segments are functional to encode a gamma antibody Fc region.

14. The mouse of claim 6, wherein said human gamma constant region comprises a human CH1 gene segment.

15. The mouse of claim 6, wherein said human CH2 and human CH3 gene segments are human CH2 gamma-1 and human CH3 gamma-1 gene segments.

16. The mouse of claim 1, wherein said non-mu heavy chain constant region comprises a human CH1 gene segment.

17. The mouse of claim 1, wherein said human non-mu constant region comprises a human gamma-1 constant region comprising human CH1, human CH2 and human CH3.

18. The mouse of claim 17, wherein said endogenous IgH locus does not comprise a mouse gamma-1 constant region.

19. The mouse of claim 1, wherein said mouse does not express endogenous antibody heavy chains of said non-mu isotype.

20. The mouse of claim 1, wherein said non-mu heavy chain constant region does not comprise a human CH1 gene segment.

21. The mouse of claim 1, wherein said human CH2 and human CH3 gene segments are human CH2 gamma-1 and human CH3 gamma-1 gene segments.

22. The mouse of claim 1, wherein said human non-mu constant region comprises a human gamma CH1 gene segment in place of endogenous mouse gamma CH1 gene segment.

23. The mouse of claim 1, wherein said mouse is homozygous for insertion of the human DNA in first and second copies of an endogenous IgH antibody locus.

24. The mouse of claim 1, wherein said mouse is homozygous for insertion of the human DNA in first and second copies of an endogenous Ig light chain antibody locus.

25. A mouse, whose genome comprises a gene locus for expression of antibody heavy chains, said locus comprising:
(a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and
(b) a non-mu heavy chain constant region comprising non-mu heavy chain constant region gene segments comprising a human CH2 gene segment and a human CH3 gene segment encoding non-mu antibody heavy chains comprising (i) non-mu heavy chain constant domains and (ii) human heavy chain variable domains; wherein said unrearranged human heavy chain variable region is upstream of and operably linked to said non-mu heavy chain constant region at an endogenous IgH locus and said human CH2 and human CH3 gene segments are a human gamma CH2 gene segment and a human gamma CH3 gene segment that are in place of endogenous non-mu heavy chain constant region DNA, such that said human heavy chain variable region gene segments are able to recombine for expression of an antibody heavy chain comprising a human gamma heavy chain antibody Fc region comprising a human gamma CH2 and a human gamma CH3 and a human heavy chain variable domain, and
wherein said heavy chain locus comprises endogenous constant region DNA such that said human non-mu constant region comprising gamma CH2 and CH3 gene segments is flanked by endogenous intergenic constant region DNA flanking endogenous CH2 and CH3 gene segments in an endogenous IgH locus.

26. A mouse, whose genome comprises a gene locus for expression of antibody heavy chains, said locus comprising:
(a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and (b) a non-mu heavy chain constant region comprising non-mu heavy chain constant region gene segments comprising a human CH2 gene segment and a human CH3 gene segment encoding non-mu antibody heavy chains comprising (i) non-mu heavy chain constant domains and (ii) human heavy chain variable domains; wherein said unrearranged human heavy chain variable region is upstream of and operably linked to said non-mu heavy chain constant region at an endogenous IgH locus and said human CH2 and human CH3 gene segments are in place of endogenous non-mu heavy chain constant region DNA, such that said human heavy chain variable region gene segments are able to recombine for expression of a non-mu antibody heavy chain comprising a human non-mu heavy chain antibody Fc region comprising a human CH2 and a human CH3 and a human heavy chain variable domain, wherein said locus comprises endogenous heavy chain intergenic constant region DNA between said human gamma constant region CH2 and CH3 gene segments, wherein said endogenous heavy chain intergenic constant region DNA comprises endogenous DNA between endogenous CH2 and CH3 gene segments in an endogenous IgH locus.

27. A mouse, whose genome comprises a gene locus for expression of antibody heavy chains, said locus comprising:
(a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and
(b) a non-mu heavy chain constant region comprising non-mu heavy chain constant region gene segments comprising a human CH2 gene segment and a human CH3 gene segment encoding non-mu antibody heavy chains comprising (i) non-mu heavy chain constant domains and (ii) human heavy chain variable domains;
wherein said unrearranged human heavy chain variable region is upstream of and operably linked to said non-mu heavy chain constant region at an endogenous IgH locus and said human CH2 and human CH3 gene segments are in place of endogenous non-mu heavy chain constant region DNA, such that said human heavy chain variable region gene segments are able to recombine for expression of a non-mu antibody heavy chain comprising a human non-mu heavy chain antibody Fc region comprising a human CH2 and a human CH3 and a human heavy chain variable domain, wherein said locus comprises an endogenous switch of said non-mu isotype, wherein said switch is operably linked to said human CH2 and said human CH3 gene segments for isotype switching to said human CH2 and CH3 gene segments.

28. A mouse, whose genome comprises a gene locus for expression of antibody heavy chains, said locus comprising:
(a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and
(b) a heavy chain constant region comprising one or more human gamma constant regions selected from the group consisting of gamma-1, gamma-2, gamma-3 and gamma-4, wherein each of said one or more human gamma constant regions comprises CH2, CH3, M1 and M2 gene segments,
said (a) and (b) encoding gamma antibody heavy chains comprising (i) gamma heavy chain constant domains and (ii) human heavy chain variable domains;
wherein said unrearranged human heavy chain variable region is upstream of and operably linked to said gamma heavy chain constant region at an endogenous IgH locus and said human CH2 and human CH3 gene segments are in place of endogenous gamma heavy chain constant region DNA, such that said human heavy chain variable region gene segments are able to recombine for expression of a gamma antibody heavy chain comprising a human gamma heavy chain antibody Fc region comprising a human CH2 and a human CH3 and a human heavy chain variable domain.

29. The mouse of claim 28, wherein said one or more human gamma constant regions further comprise the poly-A immediately 3' of CH3 or M2.

30. A mouse, whose genome comprises a gene locus for expression of antibody heavy chains, said locus comprising:
(a) an unrearranged human heavy chain variable region comprising human heavy chain variable region gene segments comprising a plurality of unrearranged human variable gene segments (VH), one or more unrearranged human D gene segments (D) and one or more human JH gene segments (JH) for expression of a plurality of human heavy chain variable domains; and
(b) one or more human gamma heavy chain constant regions comprising gamma heavy chain constant region gene segments comprising a human CH2 gene segment and a human CH3 gene segment encoding gamma antibody heavy chains comprising (i) gamma heavy chain constant domains and (ii) human heavy chain variable domains;
wherein said unrearranged human heavy chain variable region is upstream of and operably linked to said gamma heavy chain constant region at an endogenous IgH locus and said human CH2 and human CH3 gene segments are selected from the group consisting of (i) a human IGHG1*01 CH2 gene segment and a human IGHG1*01 CH3 gene segment, (ii) a human IGHG2*01 CH2 gene segment and a human IGHG2*01 CH3 gene segment, (iii) a human IGHG3*01 CH2 gene segment and a human IGHG3*01 CH3 gene segment, (iv) a human IGHG3*03 CH2 gene segment and a human IGHG3*03 CH3 gene segment, (v) a human IGHG3*04 CH2 gene segment and a human IGHG3*04 CH3 gene segment and (vi) a human IGHG4*01 CH2 gene segment and a human IGHG4*01 CH3 gene segment, wherein the human CH2 and CH3 are in place of endogenous gamma heavy chain constant region DNA, such that said human heavy chain variable region gene segments are able to recombine for expression of an antibody heavy chain comprising a human gamma heavy chain antibody Fc region comprising a human gamma CH2 and a human gamma CH3 and a human heavy chain variable domain.

* * * * *